(12) United States Patent
Gouverneur

(10) Patent No.: US 7,572,928 B2
(45) Date of Patent: Aug. 11, 2009

(54) FLUORINATION PROCESS

(75) Inventor: Veronique Gouverneur, Oxford (GB)

(73) Assignee: Isis Innovation Limited, Oxford (GB)

( * ) Notice: Subject to any disclaimer, the term of this patent is extended or adjusted under 35 U.S.C. 154(b) by 237 days.

(21) Appl. No.: 11/292,308

(22) Filed: Dec. 2, 2005

(65) Prior Publication Data

US 2007/0142632 A1 Jun. 21, 2007

(51) Int. Cl.
C07F 7/08 (2006.01)
C07F 7/10 (2006.01)

(52) U.S. Cl. ...................... 556/441; 556/476
(58) Field of Classification Search ........... 556/441, 556/476
See application file for complete search history.

(56) References Cited

OTHER PUBLICATIONS

Differding, E.; Lang, R.W., *Tetrahedron Lett.* 1988, 29, 6087-6090.
Ma, J.-A.; Cahard, D., *Chem. Rev.* 2004, 104, 6119-6146.
Kollonitsch, J.; Marburg, S.; Perkins, L. M., *J. Org. Chem.* 1979 44, 771-777.
Gouverneur, V.; Greedy, B. *Chem. Eur. J.* 2002, 8, 766-771.
D. Cahard et al, *Org. Lett.* 2000, 2, 3699-3701.
D. Cahard et al, *Tetrahedron lett.* 2001, 42, 1867-1869.
Abstract of a talk given by N. Shibata Sep. 5, 2005.
Thibaudeau, S.; Fuller, R.; Gouverneur,V. *Org. Biomol. Chem.*, 2004, 2, 1110-1112.
Hoye, T. R.; Promo, M. A. *Tetrahedron Lett.*, 1999, 40, 1429-1432.
Burfeindt et al, *J. Am. Chem. Soc.*, 1998, 3629-3634.
Schaffrath et al, *Angew. Chem. Int. Ed.*, 2002, 41, 3913.
Dong et al, *Nature* 2004, 427, 561-565.
DeYoung, J. et al, *J. Chem. Soc. Chem. Commun.* 1992, 811.
V. Grakauskas, A. Guest, *J. Org. Chem.* 1978, 43, 3485.
M. Schlosser, G. Heinz, *Chem. Ber.* 1969, 102, 1944.
M.J. Adam, J.M. Berry, L.D. Hall, B. D. Pate, T.J. Ruth, *Can J. Chem.* 61, 1983 658-660.
A. P. Lothian, C. A. Ramsden, *Synlett* 1993, 753-755.
Takeuchi, Y. et al, *J.Org. Chem.*, 1999, 64, 5708-5711.
B. Greedy, JM Paris, T. Vidal, V. Gouverneur, *Angewandte Chemie Int. Ed.* 2003, 42, 3291-3294.
Chatani et al, *J. Org. Chem.* 1995, 60, 1834-1840.
B. Greedy, V. Gouverneur, *Chem. Commun.* 2001 233-234.
G. Mentink, J. H. van Maarseveen, H. Hiemstra, *Org. Lett.* 2002, 4, 3497.
Nishiyama, T. et al, *Tetrahedron Lett.* 1998, 43-46.
W. J. Middelton, *J. Org. Chem.* 1975, 40, 574-578.
Gree et al, *J. Org. Chem.* 1996, 61, 1918.
S. Thibaudeau, V. Gouverneur, *Org. Lett.* 2003, 4891-4893.
Davis, F.A. et al, *Tetrahedron Lett.*, vol. 32, No. 13, 1991, 1631-1634.
Van Overmeire, I. et al, *J. Med. Chem.* 1999, 42, 2697.
Van Overmeire, I. et al, *J. Med. Chem.* 2000, 43, 4189.
Usse et al, *Tetrahedron: Asymmetry* 2001, 1689.
A. G. Myers, J.K. Barbay, B. Zhong, *J. Am. Chem. Soc.* 2001, 123, 7207.
Chamberlin et al, *J. Am. Chem. Soc.* 1987, 109, 672-677.
Okada et al, *J. Fluorine Chemistry* 1997, 82, 157-161.
G. H. Posner et al, *Eur. J. Org. Chem.* 2003, 3889.
Kabat et al, *J. Org. Chem.* 2001, 66, 6141.
D. A. Evans, *J. Am. Chem. Soc.* 1993, 115, 6460.
L. Ghosez, *J. Am. Chem. Soc.* 1999, 121, 2617.
Y. Landais et al, *Curr. Org. Chem.* 2002, 6, 1369.
Shibata, N. et al, *J. Am. Chem. Soc.* 2001 123, 7001-7009.
Shibata, N. et al, *J. Org. Chem.* 2003, 68(6), 2494-2497.
Shibata, N. et al, *J. Am. Chem. Soc.* 2000, 122(43), 10728-10729.
Mohar, B. et al, *Angew. Chem. Int. Ed.*, 2001, 40(22), 4214-4216.

*Primary Examiner*—Elvis O Price
(74) *Attorney, Agent, or Firm*—Nixon & Vanderhye P.C.

(57) ABSTRACT

Compounds of formula (II), (IIIa) or (IIIb)

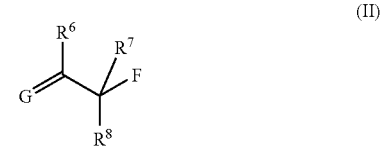

(II)

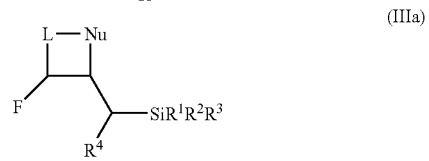

(IIIa)

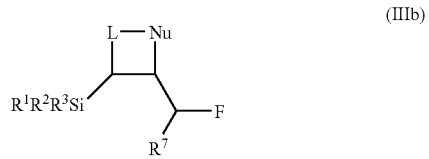

(IIIb)

(variables are described in the specification) are prepared by fluorination of β,γ-unsaturated alkyl silanes. These compounds are useful as building blocks in the pharmaceutical industry.

12 Claims, No Drawings

FLUORINATION PROCESS

FIELD OF THE INVENTION

The present invention relates to the fluorination of β,γ-unsaturated alkyl silanes. The present invention also relates to certain compounds produced by such fluorination reactions, and to further reactions involving the products of such fluorination reactions.

BACKGROUND TO THE INVENTION

Fluorinated compounds have a wide range of applications, for instance as building blocks in drug synthesis in the pharmaceutical industry. The incorporation of a fluoro substituent α- to a carbonyl group is now well established, with several reagent-based enantioselective fluorinations of enolates or silyl enol ethers having been reported; see for example Differding, E.; Lang, R. W. *Tetrahedron Lett.* 1988, 29, 6087-6090.

More recently, it has been found that transition metal complexes and small organic molecules are efficient catalysts for the formation of enantioenriched α-fluorinated carbonyl derivatives; see for example Ma, J.-A.; Cahard, D. *Chem. Rev.* 2004, 104, 6119-6146.

By way of contrast, few synthetic routes have been developed for the preparation of homochiral fluorinated building blocks other than α-fluorinated carbonyl compounds. For example, a general methodology for the preparation of enantiopure β-fluorinated γ,δ-unsaturated carboxylic acids with a stereogenic fluorinated allylic carbon has yet to be developed. Various alternative syntheses of enantioenriched β-fluorinated carboxylic acids not featuring an allylic fluoride are known, for example: Kollonitsch, J.; Marburg, S.; Perkins, L. M. *J. Org. Chem.* 1979 44, 771-777.

It has also been reported that non-aromatic organosilanes, such as vinylsilanes, allylsilanes and allenylmethylsilanes, react with 1-chloromethyl-4-fluoro-1,4-diazoniabicyclo[2.2.2]octane bis(tetrafluoro-borate) (Selectfluor™) to give structurally diverse fluorinated compounds. Using this methodology for electrophilic fluorination, fluoroalkenes, difluorinated amides, ethers or alcohols, allylic fluorides and fluorodienes have been made available; see for example Gouverneur, V.; Greedy, B. *Chem. Eur. J.* 2002, 8, 766-771.

Routes to allylic fluorides are rare and known approaches based on the use of nucleophilic sources of fluorine reacting with allylic alcohols suffer from problems of double bond transposition. The present invention provides an alternative route to allylic fluorides based on the electrophilic fluorodesilylation of allylsilanes using a source of electrophilic fluorine.

SUMMARY OF THE INVENTION

The present invention allows structurally diverse β,γ-unsaturated alkyl silanes to be fluorinated, thereby producing homochiral fluorinated compounds that are useful as synthetic building blocks in, for example, the pharmaceutical industry. Accordingly the present invention provides a process for producing a compound of formula (II), (IIIa) or (IIIb)

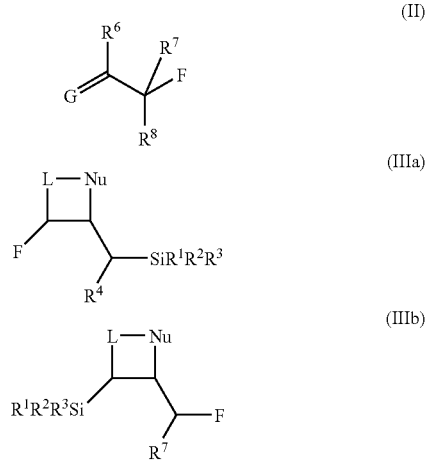

wherein $R^6$ is selected from hydrogen, aryl, -alk-aryl, $C_{1-15}$alkyl, $C_{2-15}$alkenyl and $C_{2-15}$alkynyl or $R^6$ and $R^7$, together with the carbon atoms to which they are attached, represent a 5, 6 or 7-membered carbocyclic group or a 5, 6 or 7-membered heterocyclic group containing 1, 2 or 3 heteroatoms independently selected from N, O, P and S, wherein a heteroatom is not directly attached to the ene moiety depicted in formula (I) and wherein the carbocyclic or heterocyclic group is unsubstituted or substituted by one or more groups independently selected from $C_{1-6}$alkylidene, aryl-$C_{1-6}$alkylidene, $R^{10}$, -alk-$R^{10}$, —C(O)$R^{10}$, -alk-C(O)$R^{10}$, —C(O)O$R^{10}$, -alk-C(O)O$R^{10}$, —OC(O)$R^{10}$, -alk-OC(O)$R^{10}$, —O$R^{10}$, —OTBS, -alk-OTBS, -alk-O$R^{10}$, —C(O)N$R^{11}R^{12}$ and -alk-C(O)N$R^{11}R^{12}$;

$R^7$ is selected from hydrogen, CH(NH$R^{13}$)(CH$_2$)$_m$O$R^{13}$, CH(N(C(O)OC(CH$_3$)$_3$)$R^{13}$)(CH$_2$)$_m$O$R^{13}$, $C_{1-15}$alkyl, $C_{2-15}$alkenyl and $C_{2-15}$alkynyl which alkyl, alkenyl and alkynyl groups are straight or branched and are unsubstituted or substituted by one or more groups independently selected from aryl, —C(O)O-alk-H and —C(O)—N$R^{11}R^{12}$;

$R^8$ is selected from hydrogen, aryl, $C_{1-15}$alkyl, $C_{2-15}$alkenyl and $C_{2-15}$alkynyl;

(i) G is —C($R^4$)($R^5$)—; or (ii) G is O and $R^6$ and $R^7$, together with the carbon atoms to which they are attached, represent a 5, 6 or 7-membered carbocyclic or heterocyclic group as defined above which is substituted as defined above;

$R^4$ is selected from hydrogen, -alk-H, aryl, -alk-aryl, —O-aryl, —O-alk-aryl-, -alk-O-aryl, -alk-O-alk-aryl, —O-alk-H, -alk-O-alk-H, —C(O)-aryl, —C(O)-alk-aryl, -alk-C(O)-aryl, -alk-C(O)-alk-aryl, —C(O)-alk-H, -alk-C(O)-alk-H, —C(O)N(-alk-H)C(O)O-alk-H, -alk-C(O)N(-alk-H)C(O)O-alk-H, wherein when $R^5$ is an unsubstituted or substituted hydrocarbon group with two or more carbon atoms it is saturated between C1 and C2;

$R^5$ is selected from hydrogen, -alk-H, aryl, -alk-aryl, —O-aryl, —O-alk-aryl-, -alk-O-aryl, -alk-O-alk-aryl, —O-alk-H, -alk-O-alk-H, —C(O)-aryl, —C(O)-alk-aryl, -alk-C(O)-aryl, -alk-C(O)-alk-aryl, —C(O)-alk-H, -alk-C(O)-alk-H, —C(O)N(-alk-H)C(O)O-alk-H, -alk-C(O)N(-alk-H)C(O)O-alk-H, wherein when $R^5$ is an unsubstituted or substituted hydrocarbon group with two or more carbon atoms it is saturated between C1 and C2, or $R^5$ and $R^8$, together with the $C_3$ moiety that links $R^5$ and $R^8$, represents a 5, 6 or 7-membered carbocyclic group or a 5, 6 or 7-membered heterocyclic group containing 1, 2 or 3 heteroatoms independently selected from N, O, P and S, wherein a heteroatom is not directly attached to the ene moiety depicted in formula (I) and wherein the carbocyclic or heterocyclic group is unsubstituted or substituted by one or more groups independently selected from $C_{1-6}$alkylidene, aryl-$C_{1-6}$alkylidene, $R^{10}$, -alk-$R^{10}$, —C(O)$R^{10}$, -alk-C(O)$R^{10}$, —C(O)O$R^{10}$, -alk-C(O)O$R^{10}$, —OC(O)$R^{10}$, -alk-OC(O)$R^{10}$, —O$R^{10}$, —OTBS, -alk-OTBS, -alk-O$R^{10}$, —C(O)N$R^{11}R^{12}$ and -alk-C(O)N$R^{11}R^{12}$;

$R^{10}$ is selected from $C_{1-6}$alkyl, $C_{2-6}$alkenyl, $C_{2-6}$alkynyl and phenyl, or, when two $R^{10}$ groups are attached directly to two adjacent carbon atoms on (i) the carbocyclic or heterocyclic group that can be represented by $R^6$ and $R^7$, together with the carbon atoms to which they are attached, or (ii) the heterocyclic group that can be represented by $R^5$, $R^8$ and the $C_3$ moiety that links $R^5$ and $R^8$, then those two $R^{10}$ groups can, together, represent a group —C(O)—O—C(O)—, a group —O—C($R^{14}$)$_2$—O— or a group —O-alk-O—, or, when two $R^{10}$ groups are attached directly to two adjacent carbon atoms on the carbocyclic group that can be represented by $R^5$, $R^8$ and the $C_3$ moiety that links $R^5$ and $R^8$, then those two $R^{10}$ groups can, together, represent a group —C(O)—O—C(O)—;

$R^{11}$ and $R^{12}$, together with the nitrogen atom to which they are attached, represent an N-oxazolidinyl group which is substituted by $R^{10}$ or -alk-$R^{10}$;

the two groups $R^{13}$ in a given substituent together represent a divalent $C_{1-6}$alkylene group, which alkylene group completes a ring when taken together with the atoms to which it is attached;

the two groups $R^{14}$ in a given substituent together represent a divalent $C_{4-6}$alkylene group, which alkylene group completes a ring when taken together with the atom to which it is attached;

-alk- is a straight or branched $C_{1-6}$alkylene, $C_{2-6}$alkenylene or $C_{2-6}$alkynylene group which is unsubstituted or substituted by halogen;

m is an integer selected from 1, 2 and 3;

$R^1$, $R^2$ and $R^3$ are independently selected from $C_{1-6}$alkyl and phenyl, wherein at least one of $R^1$, $R^2$ and $R^3$ is not methyl;

L is a $C_{1-3}$alkylene group which is unsubstituted or substituted by one or more groups independently selected from $R^{10}$, aryl, -alk-aryl, —C(O)O-alk-H and —C(O)—N$R^{11}R^{12}$; and Nu is —C(O)O—; or L is a $C_{2-4}$alkylene group which is unsubstituted or substituted by one or more groups independently selected from $R^{10}$, aryl, -alk-aryl, —C(O)O-alk-H and —C(O)—N$R^{11}R^{12}$; and Nu is —O—;

by attaching a fluoro group gamma to a silane group, which process comprises contacting a source of electrophilic fluorine with a compound of formula (I):

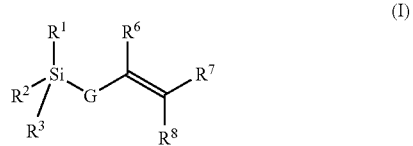

wherein either (a) $R^1$, $R^2$ and $R^3$ are each independently selected from hydrogen, $C_{1-6}$alkyl and phenyl; G, $R^4$, $R^5$, $R^6$, $R^7$ and $R^8$ are as defined above; and the compound produced is of formula (II) as defined above;

(b) $R^1$, $R^2$ and $R^3$ are independently selected from $C_{1-6}$alkyl and phenyl and at least one of $R^1$, $R^2$ and $R^3$ is not methyl; G is —C($R^4$)($R^5$)—, $R^4$ is as defined above, $R^5$, $R^6$ and $R^8$ are hydrogen; $R^7$ is -L-NuH; L and Nu are as defined above; and the compound produced is of formula (IIIa) as defined above; or (c) $R^1$, $R^2$ and $R^3$ are independently selected from $C_{1-6}$alkyl and phenyl and at least one of $R^1$, $R^2$ and $R^3$ is not methyl; G is —C($R^4$)($R^5$)—, $R^4$ is -L-NuH; $R^5$, $R^6$ and $R^8$ are hydrogen; $R^7$ is as defined above; L and Nu are as defined above; and the compound produced is of formula (IIIb) as defined above.

DETAILED DESCRIPTION OF THE INVENTION

An alkyl group is an unsubstituted or substituted, straight or branched chain saturated hydrocarbon radical. Unless otherwise specified it contains from 1 to 15 carbon atoms. Typically it is $C_{1-10}$alkyl. More typically it is $C_{1-8}$alkyl, for instance $C_{1-6}$ alkyl. Preferably it is $C_{1-4}$ alkyl, for example methyl, ethyl, i-propyl, n-propyl, t-butyl, s-butyl or n-butyl. It may also be pentyl, hexyl, heptyl, octyl and the various branched chain isomers thereof.

An alkenyl group, unless otherwise specified, is an unsubstituted or substituted, straight or branched chain $C_{2-15}$ hydrocarbon radical having one or more double bonds. Typically it is $C_{2-8}$ alkenyl, for instance $C_{2-6}$ alkenyl, such as allyl, butenyl, butadienyl, pentenyl or hexenyl. When the alkenyl group is substituted it typically bears one or more achiral alkyl groups, for instance one or two achiral alkyl groups, such as $C_{1-4}$ alkyl, for example methyl, ethyl, i-propyl, n-propyl, t-butyl, s-butyl or n-butyl.

An alkynyl group, unless otherwise specified, is an unsubstituted or substituted, straight or branched chain $C_{2-15}$ hydrocarbon radical having one or more triple bonds. Typically it is $C_{2-8}$ alkynyl, for instance $C_{2-6}$ alkynyl, such as ethynyl, propynyl or butynyl. When the alkynyl group is substituted it typically bears one or more achiral alkyl groups such as unsubstituted $C_{1-4}$ alkyl, for example methyl, ethyl, i-propyl, n-propyl, t-butyl, s-butyl or n-butyl.

In one embodiment, where there are two free bonding sites at the atom, which atom is typically a carbon atom, that may be substituted by an alkylidene group. Typically, the alkylidene group is an ethylidene group. More typically, it is an ethylidene group, which is substituted. Typically said substituent is a phenyl group. In one embodiment the alkylidene group is attached to the rest of the molecule such that the double bond by which it is attached is conjugated to the alkene group that is β,γ- to the silane group.

An alkylene group, unless otherwise specified, is an unsubstituted or substituted, straight or branched chain saturated divalent hydrocarbon group. Typically it is $C_{1-8}$alkylene, for instance $C_{1-6}$ alkylene. Preferably it is $C_{1-4}$alkylene, for example methylene, ethylene, i-propylene, n-propylene, t-butylene, s-butylene or n-butylene. It may also be pentylene, hexylene, heptylene, octylene and the various branched chain isomers thereof.

An alkenylene group, unless otherwise specified, is an unsubstituted or substituted, straight or branched chain divalent hydrocarbon group containing one or more double bonds. Typically it is $C_{2-8}$ alkenylene, for instance $C_{2-6}$ alkenylene, such as allylene, butenylene, butadienylene, pentenylene or hexenylene.

An alkynylene group, unless otherwise specified, is an unsubstituted or substituted, straight or branched chain divalent hydrocarbon group having one or more triple bonds. Typically it is $C_2$-$C_8$ alkynylene, for instance $C_2$-$C_6$ alkynylene, such as ethynylene, propynylene or butynylene.

When a given substituent can be an alkyl, alkenyl or alkynyl group, typically it is an alkyl group.

A heterocyclic group is a non-aromatic group. Typically it is a 5- or 6-membered group. More typically it is a 6 membered group. Typically the heterocyclic group contains 1, 2 or 3 heteroatoms. More typically, it contains 1 or 2. Most typically it contains 1. The heteroatoms in the heterocyclic group are typically selected from N, O and S. More typically the heteroatom is N or O. Most typically it is O. The heterocyclic group typically contains no or one further double bond in addition to the alkene moiety depicted in formula (I). Typical examples of suitable heterocyclic groups include dihydropyran, pyran, tetrahydropyridine and dihydropyridine. The heterocyclic group is unsubstituted or substituted with one or two substituents. Typically it is substituted by one group. Typical substituents for a heterocyclic group include nitro, halogen, trifluoromethyl, methyl and methoxy.

In one embodiment, when $R^6$ and $R^7$, together with the carbon atoms to which they are attached, represents a heterocyclic group or $R^5$ and $R^8$, together with the $C_3$ moiety that links $R^5$ and $R^8$, represents a heterocyclic group, there is no heteroatom alpha to the alkene moiety depicted in formula (I).

A carbocyclic group is a non-aromatic group. Typically it is a 5- or 6-membered group. More typically it is a 6 membered group. The carbocyclic group typically contains no or one further double bond in addition to the alkene moiety depicted in formula (I). Typical examples of suitable carbocyclic groups include cyclohexene, cyclopentene, cycloheptene and 1,4cyclohexadiene. The carbocyclic group is unsubstituted or substituted with one or two substituents. Typically, it is substituted by one group. Typical substituents for a carbocyclic group include nitro, halogen, trifluoromethyl, methyl and methoxy.

An aryl group typically contains from 6 to 10 carbon atoms. An aryl group can be a monocyclic ring, for example phenyl, or, unless otherwise specified, may consist of two or more fused rings, for example naphthyl. An aryl group is typically unsubstituted or substituted with one or two substituents. Typical substituents for an aryl group include nitro, halo, $C_{1-6}$alkyl and $C_{1-6}$alkoxy groups, for instance chloro, methyl and methoxy groups.

A halogen is typically fluorine, chlorine or bromine.

In variants (b) of the process of the invention as defined above, L is typically a $C_1$alkylene or $C_2$alkylene group. More typically it is a $C_1$alkylene group. Typically L is unsubstituted. Typical examples of L include methylene and ethylene groups. In one embodiment of process variant (b) of the process of the invention as defined above, L is an unsubstituted methylene or ethylene group. In one embodiment of variants (b) and (c) of the process of the invention as defined above, L is a $C_1$alkylene or $C_2$alkylene group, typically a $C_1$alkylene group and Nu is —C(O)O—. In another embodiment of variants (b) and (c) of the process of the invention as defined above, L is a $C_2$alkylene or $C_3$alkylene group, typically a $C_2$alkylene group and Nu is —O—.

In one embodiment the present invention provides a process according to variant (b) or (c) as defined above, wherein $R^4$ is H or -alk-H; and (i) L is an ethylene group which is unsubstituted or substituted by one or more of $R^{10}$, aryl and -alk-aryl and Nu is —O—; or (ii) L is a methylene group which is unsubstituted or substituted by one or more of $R^{10}$, aryl and -alk-aryl and Nu is —C(O)O—. Typically in this embodiment $R^4$ is H. More typically, either (i) L is an ethylene group substituted by a phenylethyl group alpha to Nu and Nu is —O—, or (ii) L is an unsubstituted methylene or ethylene group and Nu is —C(O)O—. Typically in this embodiment of the process of the present invention, $SiR^1R^2R^3$ is an $Si^iPr_3$ group.

The source of electrophilic fluorine may be any such source which is known in organic chemistry. Examples include $FClO_3$, $CF_3OF$, $CF_3CF_2OF$, $CF_3C(O)OF$, $CH_3C(O)OF$, $XeF_2$, $CsSO_4F$. Other options include reagents where the F is bonded to N such as NFSi, NFOBS (N-fluoro-O-benzenedisulfonimide) and N—F ammonium salts and derivatives and N-fluoropyridinium salts thereof. Typically, the N—F ammonium salts are used. In one embodiment, the source of electrophilic fluorine is chiral. Typically in this embodiment, a substantially enantiomerically pure form of the chiral source of electrophilic fluorine is used. NF-DHQB.$BF_4$ is an examples of a suitable source of electrophilic fluorine. Further examples are also possible based on the following alkaloids DHQB (dihydroquinine-4-chlorobenzoate), $(DHQ)_2$PYR (hydroquinine-2,5-diphenyl-4,6-pyrimidinediyl diether), DHQDB (dihydroquinidine-4-chlorobenzoate), DHQMQE (dihydroquinine 4-methyl-2-quinoyl ether) and DHQPE (dihydroquinine 9-phenanthyl ether). A preferred source of electrophilic fluorine for use in the process of the invention as defined above is [1-(chloromethyl)-4-fluoro-1,4-diazoniabicyclo[2.2.2]octane bis(tetrafluoroborate)], also known as Selectfluor™. In another embodiment a N-fluoroammonium salt derived from a cinchona alkaloid can be used as the fluorination reagent in the process of the invention. Suitable examples are described by D. Cahard et al in *Org. Lett.* 2000, 2, 3699-3701 and *Tetrahedron Lett.* 2001, 42, 1867-1869

The skilled person will appreciate that various methods known in the art can be employed for preparing the starting compound of formula (I) as defined above. For example, it may be prepared by submitting a compound of formula (IV):

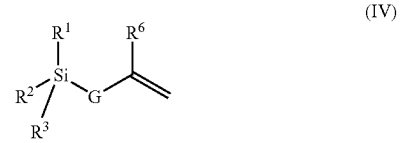

(IV)

wherein each of $R^1$ to $R^3$, G and $R^6$ is as defined above, to cross metathesis coupling with a compound of formula (V):

wherein $R^7$ and $R^8$ are as defined above. This reaction is carried out in the presence of a metal catalyst. Typically the metal catalyst is a Ruthenium catalyst such as a second generation Grubbs catalyst. In another embodiment the catalyst is a Hoveyda catalyst or a Schrock catalyst. The reaction is carried out in a solvent. Suitable solvents include organic solvents such as dichloromethane. Typically the reaction requires heating. In one embodiment the reaction may be carried out under reflux.

Typically more of the E isomer is formed in the above reaction than the Z isomer. The E/Z ratio can be increased by heating the reaction to reflux.

The compound of formula (V) may be readily available, or can be prepared from precursor compounds. For instance, it may be prepared by the reaction of an aldehyde with a Grignard reagent. For example, a compound of formula (V) wherein $R^7$ is $Ph(CH_2)_2CCH(OH)CH_2$— can be prepared by reaction of $Ph\text{-}(CH_2)_2CHO$ with $(BrMgCH_2C(R^8)\!=\!CH_2$. Alternatively, it may be prepared by a similar reaction involving an organozinc reagent in place of the Grignard reagent. The present inventors have found that the given ratio of E/Z compound in the starting material of formula (I) can correlate with the syn/anti ratio in the product. Accordingly, in one embodiment the present invention provides a process of the invention as defined above which is diastereoselective.

In one embodiment of the process of the present invention as defined above, the group $R^7$ in the compound of formula (I) may be a group based on Garner's aldehyde. Example 46 which follows describes one way this group may be attached. Garner's aldehyde is commercially available, or may be prepared according to the following scheme:

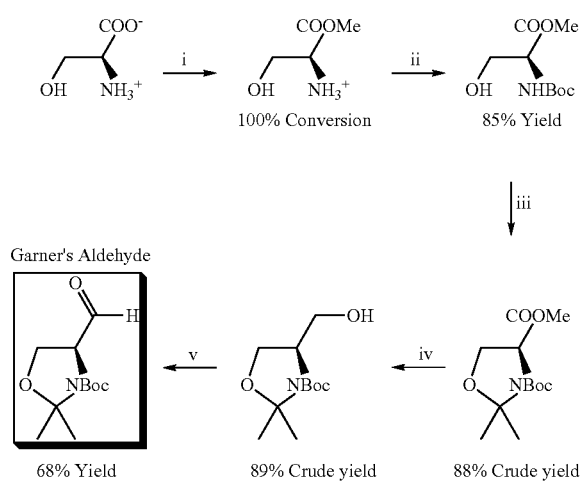

In the above scheme the reagents and conditions are as follows:(i) Acetyl chloride, MeOH, 2 h, reflux; (ii) $(Boc)_2O$, $Et_3N$, $CH_2Cl_2$, 15 h, room temperature;(iii) dimethoxypropane, $TsOH.H_2O$, toluene, 2 h, reflux; (iv) $LiAlH_4$, THF, 1 h and room temperature; and (v) DMSO, $(COCl)_2$, $CH_2Cl_2$, $NEt(^iPr)_2$, $-78°$ C.-$0°$ C.

In one embodiment of the process of the present invention as defined above, the group $R^6$ in the compound of formula (I) may be an arylalkenyl group, such as a Ph-CH=CH— group. Such compounds may, for example, be prepared according to the following scheme:

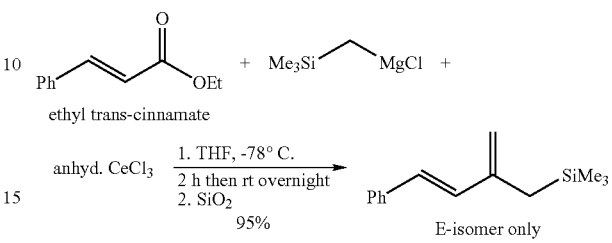

Alternatively, such compounds may be reacted further with a suitable alkene or alkyne group in a Diels Alder reaction to produce a compound of formula (I) wherein $R^6$ and $R^7$, together with the carbon atoms to which they are attached, represent a 6 membered carbocyclic group. Example 50 which follows provides typical illustrations of such reactions.

Thus, compounds of formula (I) wherein $R^6$ and $R^7$, together with the carbon atoms to which they are attached, represent a 6 membered carbocyclic group may be prepared by a Diels-Alder or hetero Diels-Alder reaction of a silylated diene, according to the following scheme

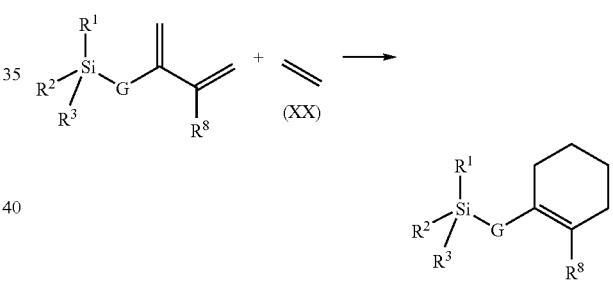

wherein $R^1$ to $R^3$, G and $R^8$ are as defined above. Either of the starting compounds in this scheme may be substituted (in the case of the diene at the terminal carbon atoms of the diene groups) to provide substitution of the carbocyclic ring in the product.

When $R^5$ and $R^8$ represent a 6-membered carbocyclic group which is substituted by one or more groups, various methods can be employed for preparing the starting compound of formula (I). Different methods may be used to produce the desired stereochemistry at the carbon centres to which the said one or more substituents are attached relative to the silane group. For example, anti, syn cyclic allyl silanes may be prepared by the desymmetrisation of silylated cyclohexadienes and syn, syn cyclic allylsilane may be prepared by Diels-Alder chemistry.

Another method that may be used for preparing the compounds of formula (I) involves reaction of a Grignard reagent of formula $R^1R^2R^3Si$-G-MgBr with an alkene of formula Br—C($R^6$)=C$R^7R^8$. Examples of this process are described by Hauser et al (C. R. Hauser, C. R. Hance, *J. Am. Chem. Soc.*, 1952, 5091, 74) and include:

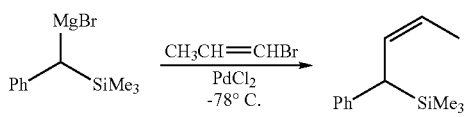

Another method that may be used for preparing the compounds of formula (I) is described by Fleming et al (I. Fleming, A. P. Thomas, *J. Chem. Soc. Chem. Commun.* 1986, 1456-1457), and involves the following scheme:

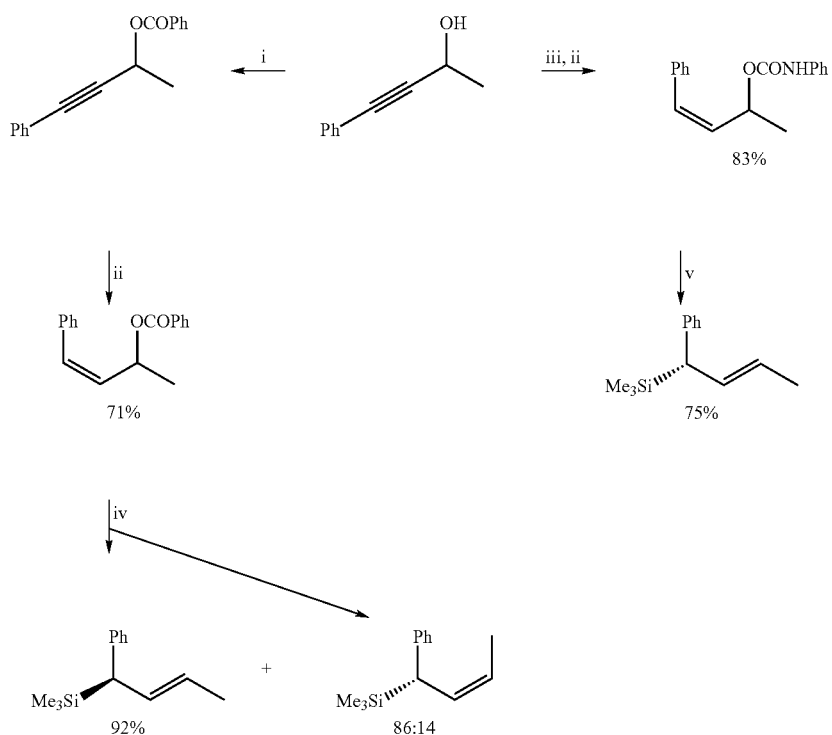

In the above scheme the reagents and conditions are as follows: i, (PhCO)$_2$, Et$_3$N, 4-N,N-dimethylaminopyridine; ii, H$_2$/Pd/BaSO$_4$/quinoline; iii, PhNCO,Et$_3$N; iv, (PhMe$_2$Si)$_2$CuLi.CuCN, 2PPh$_3$; v, (1): nBuLi, −78° C., (2): CuI, 2PPh$_3$, and (3): PhMe$_2$SiLi; vi, H$_2$, Pd/C; vii, BF$_3$.2AcOH; viii, m-chloroperbenzoic acid (MCPBA), Et$_3$N.

Typically the compound of formula (I) is present in a substantially enantiomerically pure form.

In one embodiment the present invention provides a process as defined above wherein G is —C(R$^4$)(R$^5$)—. When one of R$^4$ and R$^5$ are is not H, the substituent which is not H may be introduced by the methods described by Chan et al (T. H. Chan, D. Wang, *Chem. Rev.*, 1995, vol 95, no. 5; K. Koumaglo, T. H. Chan, *Tet. Lett.*, 1984, Vol. 25, No. 7, 712-720), for example, by a reaction along the following lines:

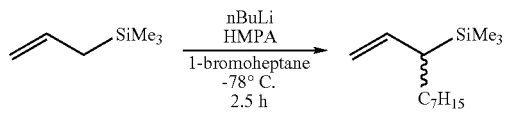

In one embodiment the present invention provides a process according to variant (a) as defined above, wherein either:

(i) G is —C(R$^4$)(R$^5$)— and the carbocyclic or heterocyclic group that can be represented by R$^5$ and R$^8$, together with the C$_3$ moiety that links R$^5$ and R$^8$, is substituted at a carbon atom such that said carbon atom is a stereocentre; or (ii) the group R$^7$, or the carbocyclic or heterocyclic group that can be formed by R$^6$ and R$^7$ together with the carbon atoms to which they are attached, is substituted at a carbon atom such that said carbon atom is a stereocentre.

In another embodiment of process variant (a) as defined above, R$^1$, R$^2$, and R$^3$ each represent C$_{1-6}$alkyl; G is —C(R$^4$)(R$^5$)—, R$^4$, R$^5$ and R$^8$ represent hydrogen; and R$^6$ and R$^7$, together with the carbon atoms to which they are attached, represent a 6-membered carbocyclic group which is substituted by one or more groups selected from C$_{1-6}$alkylidene, aryl-C$_{1-6}$alkylidene, R$^{10}$, -alk-R$^{10}$, —C(O)R$^{10}$, -alk-C(O)R$^{10}$, —C(O)OR$^{10}$, -alk-C(O)OR$^{10}$, —OC(O)R$^{10}$, -alk-OC(O)R$^{10}$, —OR$^{10}$, -alk-OR$^{10}$, —C(O)NR$^{11}$R$^{12}$ and -alk-C(O)NR$^{11}$R$^{12}$. Typically in this embodiment C$_{1-6}$alkyl is methyl and the 6-membered carbocyclic group is a cyclohexene or a 1,4-cyclohexadiene group which is substituted by one, two or three groups selected from R$^{10}$, -alk-R$^{10}$, —C(O)R$^{10}$, —C(O)OR$^{10}$, —OTBS and —C(O)NR$^{11}$R$^{12}$.

In a further embodiment of process variant (a) as defined above, R$^1$, R$^2$, and R$^3$ each represent C$_{1-6}$alkyl; G is —C(R$^4$)(R$^5$)—, R$^4$, R$^5$ and R$^8$ each represent hydrogen; R$^6$ represents hydrogen, phenyl, p-nitrophenyl or decyl; and R$^7$ is selected from hydrogen, CH(NHR$^{13}$)(CH$_2$)$_m$OR$^{13}$, CH(N(C(O)OC(CH$_3$)$_3$)R$^{13}$)(CH$_2$)$_m$OR$^{13}$ and a C$_{1-15}$alkyl group which is straight or branched and is unsubstituted or substituted by one or more groups selected from aryl, —C(O)O-alk-H and —C(O)—NR$^{11}$R$^{12}$. In a typical aspect of this embodiment $C_{1-6}$alkyl is methyl, $R^6$ represents phenyl, p-nitrophenyl or decyl and $R^7$ represents hydrogen. In another aspect of this embodiment $R^6$ represents hydrogen and $R^7$ represents $CH(NHR^{13})(CH_2)_mOR^{13}$, $CH(N(C(O)OC(CH_3)_3)R^{13})(CH_2)_mOR^{13}$ or a $C_{1-15}$alkyl group which is straight or branched and is unsubstituted or substituted by one or more groups selected from aryl, —C(O)O-alk-H and —C(O)—$NR^{11}R^{12}$. More typically $R^7$ represents $CH(NHR^{13})(CH_2)_mOR^{13}$, $CH(N(C(O)OC(CH_3)_3)R^{13})(CH_2)_mOR^{13}$, a $C_{1-15}$alkyl group which is straight or branched and is unsubstituted or an ethyl group which is 1,2-substituted by two groups selected from aryl, —C(O)O-alk-H and —C(O)—$NR^{11}R^{12}$. Yet more typically still $R^7$ represents $CH(NHR^{13})(CH_2)_mOR^{13}$, $CH(N(C(O)OC(CH_3)_3)R^{13})(CH_2)_mOR^{13}$ or an ethyl group which is substituted in the 1-position by hydrogen and one group selected from —C(O)O-alk-H and —C(O)—$NR^{11}R^{12}$ and in the 2-position by two hydrogen atoms and one aryl group, and wherein m is 1. More typically still in this aspect the ethyl group represented by $R^7$ the C-1 position is a chiral centre and the starting compound of formula (I) is present in a substantially enantiomerically pure form.

Yet more typically in the above aspect $R^1$, $R^2$, and $R^3$ in formula (I) represent methyl; $R^4$, $R^5$, $R^6$, and $R^8$ represent hydrogen; and $R^7$ represents a group of formula (VI):

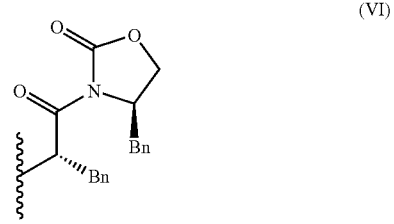

(VI)

wherein Bn is benzyl, and the process gives rise to a compound of formula (II) wherein $R^4$, $R^5$, $R^6$, and $R^8$ represent hydrogen and $R^7$ represents a group of formula (VI).

In one embodiment the present invention provides a process which further comprises functional manipulation of the allylic fluorides resulting from the process of variant (a) as defined above, such as cross-metathesis coupling with various olefinic partners and iodolactonisation. For example, in the aspect the process of the invention wherein $R^1$, $R^2$, and $R^3$ in formula (I) represent methyl; $R^4$, $R^5$, $R^6$, and $R^8$ represent hydrogen; and $R^7$ represents a group of formula (VI), the process may further comprise hydrolytic cleavage of the compound of formula (II) as defined above to produce a compound of formula (VII):

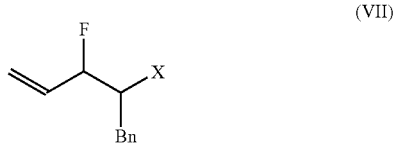

(VII)

wherein X represents —COOH and Bn is benzyl.

Any suitable reagent may be used for this reaction. For example, the reactant mixture can comprise $H_2O_2$ and LiOH in a suitable solvent such as THF—$H_2O$ (THF=tetrahydrofuran). Typically in these instances the compound of formula (II) is present in a substantially enantiomerically pure form.

The compound of formula (VII) as defined above can be treated with a reducing agent to produce a compound of formula (VII'):

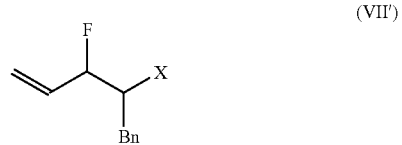

(VII')

wherein X represents $CH_2OH$.

Any suitable reducing agent may be used for this reaction. For example, the reactant mixture can comprise $LiAlH_4$ in a suitable solvent such as THF.

The compounds of formulae (VII) and (VII') are new. Accordingly, the present invention provides a compound of formula (VII"):

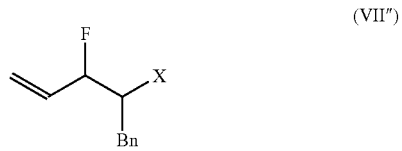

(VII")

wherein X represents —$CH_2OH$ or —C(O)OH and Bn is benzyl. The compound of formula (VII") is typically present in a substantially enantiomerically pure form.

The present invention also provides a process as defined above, which process further comprises subjecting a compound of formula (VII) as defined above to dimerisation by cross metathesis in the presence of a metal catalyst to produce a compound of formula (VIII):

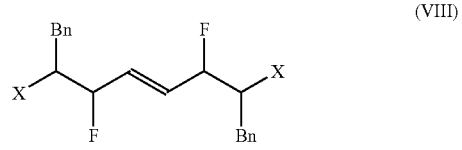

(VIII)

wherein Bn is benzyl. In one aspect of this embodiment X is —C(O)OH. In another aspect X is $CH_2OH$.

Any suitable metal catalyst can be used for this cross metathesis reaction. Typically the metal catalyst is a Ruthenium catalyst such as a second generation Grubbs catalyst. In another embodiment the catalyst is a Hoveyda catalyst or a Schrock catalyst. The X groups in the two starting compounds of formula (VII) that are to be dimerised can be linked to a common species, such that the cross metathesis step is intramolecular. Typically the common species used is an alkyl-substituted silicon moiety. The alkyl substituents are typically $C_{1-6}$alkyl groups, such as isopropyl groups. For example, the moiety can be such that when linked to the two X groups it is an $^iPr_2Si$ moiety wherein the two X groups are bonded to the Si atom.

The compound of formula (VII) as defined above may be submitted to iodolactonisation. Accordingly, the present invention further provides a process as defined above which further comprises treating a compound of formula (VII) as defined above wherein X is —C(O)OH with iodine in the presence of a base in a solvent, to produce a compound of formula (IX)

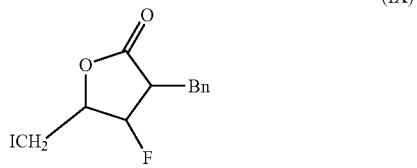

wherein Bn is benzyl.

Any suitable base and any suitable solvent may be used in this reaction. For example, the reactant mixture can comprise NaHCO$_3$ and I$_2$ in a solvent, for instance dichloromethane.

The compound of formula (VII) can be used as a synthetic building block. It is particularly useful as a building block in the synthesis of pharmaceutical agents. In one embodiment it is used as a synthetic building block in the production of Indinavir (also known as Crixivan) or a derivative or analogue thereof. Indinavir is 1-[2-hydroxy-4-[(2-hydroxy-2,3-dihydro-1H-inden-1-yl)carbamoyl]-5-phenyl-pentyl]-4-(pyridin-3-ylmethyl)-N-tert-butyl-piperazine-2-carboxamide).

In another embodiment of process variant (a) of the present invention as defined above, $R^1$, $R^2$, and $R^3$ each represent $C_{1-6}$alkyl; G is —C($R^4$)($R^5$)—, $R^4$, $R^5$ and $R^8$ represent hydrogen; and $R^6$ and $R^7$, together with the carbon atoms to which they are attached, represent a 6-membered carbocyclic group which contains only one alkene moiety (that which is depicted in formula (I)) and is substituted by two adjacent —O$R^{10}$ (such as —OH) or $R^{10}$ groups wherein the two $R^{10}$ groups together represent a group —C(O)—O—C(O)—, a group —O—C($R^{14}$)$_2$—O— or a group —O-alk-O—. Typically these two substituents are positioned opposite the alkene moiety in the ring. Typically in this embodiment of the process of the present invention, SiR$^1$R$^2$R$^3$ is a Si$^t$BuMe$_2$ or SiMe$_3$ group.

In another embodiment of process variant (a) of the present invention as defined above, $R^1$, $R^2$, and $R^3$ each represent $C_{1-6}$alkyl; G is —C($R^4$)($R^5$)—, $R^4$, $R^5$ and R represent hydrogen; and $R^6$ and $R^7$, together with the carbon atoms to which they are attached, represent a 6-membered carbocyclic group which contains only one alkene moiety (that which is depicted in formula (I)) or two alkene moieties on opposite sides of the ring (such that they are not directly conjugated) and is substituted by one or more groups independently selected from aryl, $R^{10}$, —C(O)O$R^{10}$ and —C(O)$R^{10}$. More typically the carbocyclic group is substituted by one or more groups independently selected from phenyl, —C(O)OMe and —C(O)Me and/or two adjacent $R^{10}$ groups which, together, represent a group —C(O)—O—C(O)—, a group —O—C($R^{14}$)$_2$—O— or a group —O-alk-O—. Typically in this embodiment the carbocyclic group is substituted at two or three different positions on the ring.

In the fluorination process of the present invention as defined above, the starting compound of formula (I) typically has one or more chiral centres, such as one, two or three chiral centres. The compound may accordingly have two, four or six stereoisomeric forms, respectively. More typically the compound has one or two chiral centres, in which case the compound has two or four stereoisomeric forms respectively. Most typically the compound has one chiral centre and thus two stereoisomeric forms. A chiral centre may be at a carbon atom or silicon atom. Typically, the chiral centre is at a carbon atom.

In variant (b) of the process of the invention as defined above and in variant (c) when $R^7$ is not hydrogen, an additional stereocentre is created in the product at the carbon atom to which the fluoro group becomes attached. In variant (a) of the process of the invention as defined above, the groups $R^7$ and $R^8$ are typically such that an additional stereocentre is created in the product at the carbon atom to which the fluoro group becomes attached.

Chirality in the starting material can be used to influence the stereochemistry at the carbon centre in the product bearing the fluoro group. In particular, chirality in the starting material can influence the stereochemistry of the latter carbon centre relative to the stereochemistry at the chiral centre already present. Further, chirality in the source of electrophilic fluorine can also be used to influence the stereochemistry of the carbon centre to which the fluoro group becomes attached. In one embodiment of the process of the present invention, both of these features are used in combination to control the absolute stereochemistry of the product.

The optical purity of the starting compound of formula (I) may vary. For example, at one extreme the starting compound may be present as a racemic mixture. At the other extreme the starting compound may be present in a substantially enantiomerically pure form. The process of the present invention is applicable to starting compounds having any level of optical purity.

Depending on the optical isomerism of the starting material and/or the source of electrophilic fluorine, in one embodiment the process of the present invention as defined above allows the relative stereochemistry of the carbon atom at which the fluoro group becomes attached to be controlled. In another embodiment the process of the present invention as defined above allows the absolute stereochemistry of the carbon atom at which the fluoro group becomes attached to be controlled.

In one embodiment of the process of the present invention, the starting compound of formula (I) comprises a chiral centre and is racemic, and is treated with a substantially enantiomerically pure source of electrophilic fluorine. In this case one stereoisomeric form of the product of formulae (II) or (III) is formed preferentially over another.

In another embodiment of the process of the present invention, the starting compound of formula (I) comprises a chiral centre and is present in a substantially enantiomerically pure form, and is treated with a substantially enantiomerically pure source of electrophilic fluorine. In this case one specific stereoisomeric form of the product of formulae (II) or (III) is formed in preference to all others. This approach allows absolute control over the stereochemistry of the product.

Where a compound or product is referred to having two or more stereoisomeric forms as including two or more stereoisomers, the stereoisomerism may take the form of geometric isomerism and/or optical isomerism. In one embodiment, both types of isomerism are evident: geometric isomerism arises from the presence of the alkene group in the starting compounds of formula (I) while optical isomerism results from a chiral carbon centre in one of the substituents. When $R^5$ and $R^8$, together with the $C_3$ moiety that links $R^5$ and $R^8$, represents a carbocyclic or heterocyclic group, and/or when $R^6$ and $R^7$, together with the carbon atoms to which they are attached, represents a carbocyclic or heterocyclic group, then geometrical isomerism is not possible. In one of these instances it is typical for there to be optical isomerism resulting from a chiral carbon centre in a substituent of the carbocyclic or heterocyclic group, and/or resulting from a chiral centre at a carbon atom within the carbocyclic or heterocyclic group at which one or more substituents is or are attached.

In variant (a) of the process of the invention as defined above, depending on the identity of $R^1$, $R^2$ and $R^3$ the silane moiety can be a primary, secondary or tertiary alkyl silane. Typically it is a tertiary or secondary alkyl silane. More typically it is a tertiary alkyl silane.

In variant (a) of the process of the invention as defined above, $R^1$, $R^2$ and $R^3$ are typically each selected from $C_{1-6}$alkyl and phenyl, such as methyl, ethyl, t-butyl, i-propyl or phenyl. Examples of suitable groups represented by $SiR^1R^2R^3$ include $SiMe_3$, $SiEt_3$, $SiMe_2{}^tBu$, $Si^iPr_3$, $Si^tBuPh_2$, $SiMe_2Ph$ and $SiPh_3$. Typically, $SiR^1R^2R^3$ is $SiMe_3$ or $SiEt_3$. More typically, $SiR^1R^2R^3$ is $SiMe_3$.

In variants (b) and (c) of the process of the invention as defined above, $R^1$, $R^2$ and $R^3$ are typically each selected from methyl, ethyl, t-butyl, i-propyl and phenyl. Examples of suitable groups represented by $SiR^1R^2R^3$ include $SiMe_2{}^tBu$, $Si^iPr_3$, $SiPh^iPr_2$, $Si^tBuPh_2$ and $SiPh_3$. Typically, $SiR^1R^2R^3$ is $Si^iPr_3$ or $SiPh^iPr_2$. When $SiR^1R^2R^3$ represents $SiPh^iPr_2$, the reagent from which the $SiPh^iPr_2$ group is at first introduced is typically prepared from the corresponding $Si^iPr_3$ reagent. In one embodiment of variant (a) the process of the present invention as defined above G is —$C(R^4)(R^5)$—. In another embodiment of variant (a) the process of the present invention as defined above G is O. When G is O then $R^6$ and $R^7$, together with the carbon atoms to which they are attached, represent a 5, 6 or 7-membered carbocyclic or 5, 6 or 7-membered heterocyclic group, which group is substituted as defined above. For the avoidance of doubt, in this embodiment the 5, 6 or 7 membered carbocyclic or heterocyclic group is not fused to a further cyclic moiety (with the exception that it may be so fused in the instance that $R^5$ and $R^8$, together with the $C_3$ moiety that links $R^5$ and $R^8$, represents a 5, 6 or 7-membered carbocyclic group or a 5, 6 or 7-membered heterocyclic group).

In variant (a) of the process of the invention as defined above, $R^4$ is typically hydrogen. In variant (b) of the process of the invention as defined above, $R^4$ is typically selected from hydrogen and $C_{1-6}$alkyl; more typically it is hydrogen.

In variant (a) of the process of the invention as defined above, $R^4$ and $R^5$ are each independently typically selected from hydrogen, -alk-H, aryl, -alk-aryl, —O-aryl, —O-alk-aryl-, -alk-O-aryl, -alk-O-alk-aryl, —O-alk-H, -alk-O-alk-H, —C(O)-aryl, —C(O)-alk-aryl, -alk-C(O)-aryl, -alk-C(O)-alk-aryl, —C(O)-alk-H, -alk-C(O)-alk-H, —C(O)N(-alk-H)C(O)O-alk-H, and -alk-C(O)N(-alk-H)C(O)O-alk-H, wherein when $R^4$ or $R^5$ is an alkyl group it is saturated between C1 and C2. More typically $R^4$ and $R^5$ are each independently selected from hydrogen, aryl, -alk-H, -alk-aryl, -alk-O-alk-aryl, —C(O)-alk-H and —C(O)N(-alk-H)C(O)O-alk-H. Yet more typically $R^5$ is selected from hydrogen, ethenyl, phenyl, p-trifluoromethylphenyl, benzyloxymethyl, propanoyl, —C(O)N(CH_3)C(O)O-${}^tBu$ and 2-bromoethyl. Most typically $R^4$ and $R^5$ are both hydrogen. In one embodiment, $R^4$ and $R^5$ are each independently selected from hydrogen, -alk-H, aryl, -alk-aryl, —O-aryl, —O-alk-aryl-, -alk-O-aryl, -alk-O-alk-aryl, —O-alk-H, -alk-O-alk-H, -alk-C(O)-aryl, -alk-C(O)-alk-aryl, -alk-C(O)-alk-H and -alk-C(O)N(-alk-H)C(O)O-alk-H, wherein when $R^4$ or $R^5$ is an alkyl group it is saturated between C1 and C2.

In variant (a) of the process of the invention as defined above, $R^6$ is typically selected from hydrogen, aryl and $C_{1-15}$alkyl, or $R^6$ and $R^7$, together with the carbon atoms to which they are attached, represents a 6-membered carbocyclic group, which is substituted by one or more groups independently selected from aryl-$C_{1-6}$alkylidene, $R^{10}$, —C(O)$R^{10}$, —C(O)OR$^{10}$, —OTBS and —C(O)NR$^{11}R^{12}$. More typically $R^6$ is selected from hydrogen, phenyl, p-nitrophenyl, and decyl, or $R^6$ and $R^7$, together with the carbon atoms to which they are attached, represents a 6-membered carbocyclic group, which is unsaturated or has an alkene moiety which is not conjugated to the alkene moiety depicted in formula (I), and which is substituted by one or more groups independently selected from phenylmethylidene, phenyl, methyl, $R^{10}$, —C(O)CH$_3$, —C(O)OCH$_3$, —OTBS and —C(O)NR$^{11}R^{12}$ wherein $R^{11}$ and $R^{12}$, together with the nitrogen atom to which they are attached, represent an N-oxazolidinyl group which is substituted by benzyl at the non-carbonyl carbon atom attached to the nitrogen atom. Typically, there is not more than one substituent on the 6-membered carbocyclic ring per ring member. More typically, there are 1, 2 or 3 substituents on the 6-membered carbocyclic ring. In one embodiment, the or one or more of the said one or more substituents attached to the 6-membered carbocyclic group create one or more chiral centres at the carbon atoms to which they are attached. Typically in this embodiment the process of the present invention as defined above is carried out with the compound of formula (I) present in a substantially enantiomerically pure form.

In variant (a) of the process of the invention as defined above, when $R^7$ does not form a cyclic moiety together with $R^6$ and the carbon atoms to which they are attached, $R^7$ is typically selected from hydrogen, CH(NHR$^{13}$)(CH$_2$)$_m$OR$^{13}$, CH(N(C(O)OC(CH$_3$)$_3$)R$^{13}$)(CH$_2$)$_m$OR$^{13}$, a $C_{1-15}$alkyl group which is straight or branched and is unsubstituted and a $C_{1-4}$alkyl group which is straight or branched and is substituted by one or more groups independently selected from aryl, —C(O)O-alk-H and —C(O)—NR$^{11}R^{12}$. More typically, $R^7$ is selected from hydrogen, CH(NHR$^{13}$)CH$_2$OR$^{13}$, CH(N(C(O)OC(CH$_3$)$_3$)R$^{13}$)CH$_2$OR$^{13}$, decyl, and an ethyl group which is substituted in the 1 and 2 positions by two groups independently selected from phenyl, —C(O)O—CH$_2$CH$_3$ and —C(O)NR$^{11}R^{12}$ wherein $R^{11}$ and $R^{12}$, together with the nitrogen atom to which they are attached, represent an N-oxazolidinyl group which is substituted by benzyl at the non-carbonyl carbon atom attached to the nitrogen atom.

When $R^8$ is an alkenyl or alkynyl group in variant (a) of the process of the invention as defined above it is typically saturated between C1 and C2. Typically, $R^8$ is hydrogen.

In variant (a) of the process of the invention as defined above, when two $R^{10}$ groups represent a group —O-alk-O—, typically the -alk-group therein is a straight or branched $C_{1-6}$alkylene group. More typically it is a $C_{1-4}$alkylene group, such as a group —O—C(CH$_3$)$_2$—O—. Most typically, the group -alk- is such that both O atoms to which it is attached are bonded to the same carbon atom. When a group is substituted by $R^{10}$ or -alk-$R^{10}$, typically benzyl substitutes that group. In one embodiment, the carbon atom to which benzyl is attached is a chiral centre. Typically, in this embodiment the process of the present invention as defined above is carried out with the compound of formula (I) present in a substantially enantiomerically pure form.

In variant (a) of the process of the invention as defined above, when two $R^{13}$ groups together represent a single divalent $C_{1-6}$alkylene group, typically this is a divalent $C_{1-4}$alkylene group. More typically, both points of attachment of the single divalent alkylene group are at one and the same carbon atom. For example, the alkylene group is typically —C(CH$_3$)$_2$—.

In variant (a) of the process of the invention as defined above, m is typically 1 or 2. More typically it is 1.

In variant (a) of the process of the invention as defined above, -alk- is typically a $C_{1-6}$alkylene group.

In variant (a) of the process of the invention as defined above, $R^{14}$ is typically a straight chain alkylene group, such as a $(CH_2)_4$, $(CH_2)_5$, or $(CH_2)_6$ group. More typically it is a $(CH_2)_5$ group.

In variant (a) of the process of the invention as defined above, typically at least one of $R^4$, $R^5$, $R^6$, $R^7$, and $R^8$, is other than hydrogen, aryl or unsubstituted alkyl.

In the process of the invention as defined above, the compounds described in variant (a) are typically not compounds wherein $R^5$ and $R^8$, together with the $C_3$ moiety that links $R^5$ and $R^8$, represents a 5, 6 or 7-membered carbocyclic group or a 5, 6 or 7-membered heterocyclic group and $R^6$ and $R^7$, together with the carbon atoms to which they are attached, represents a 5, 6 or 7-membered carbocyclic group or a 5, 6 or 7-membered heterocyclic group.

As used herein, Bn represents a benzyl group, $^i$Pr represents an isopropyl group, d.e. stands for diastereomeric excess and TBS represents a tert-butyldimethylsilyl group. Also, in the diagram below, (a) represents a bond above the plane of the page and (b) represents a bond below the plane of the page.

Also, the following terms are used herein: $^t$Bu (tertiary butyl), Boc (t-butoxycarbonyl), COSY (Correlation Spectroscopy (NMR)), DEE (Diethyl ether), DCM (Dichloromethane), DMAD (dimethyl Acetylenedicarboxylate), DMP (dimethoxypropane) (MVK (Methyl Vinyl Ketone (3-Butene-2-one)), NMO (N-Methylmorpholine-N-oxide), NOE(SY) (Nuclear Overhauser Effect (Spectroscopy)), PCC (Pyridinium chlorochromate), THF (Tetrahydrofuran), TBDMS (t-Butyldimethylsilyl), TMEDA (N,N,N',N'-Tetramethylethylenediamine), Ts (tosyl), p-Ts (para-tosyl), Where it is desired to obtain a particular enantiomer or a compound present in a substantially enantiomerically pure form, this may be achieved by starting from the corresponding mixture of enantiomers using a suitable conventional procedure for resolving enantiomers. Thus for example, diastereomeric derivatives may be produced by reaction of a mixture of enantiomers, for instance a racemate, with an appropriate chiral compound. The derivatives may be, for instance, salts. The chiral compound may be, for instance, a chiral base. The diastereomers may then be separated by any convenient means, for example by crystallisation, and the desired enantiomer recovered. Recovery may be, for example, by treatment with an acid where the diastereomer is a salt.

In another resolution process a racemate may be separated using chiral High Performance Liquid Chromatography. Alternatively, if desired, a particular enantiomer may be obtained by using an appropriate chiral intermediate in one of the processes described above. Where a compound is said to be present in a substantially enantiomerically pure form, this typically means that the compound possesses a percentage optical purity of at least 80%. More typically the optical purity is at least 85%, for instance 90%, or 95%, typically 98% or 99%.

Fluorine atoms possess various properties that can affect the properties of any molecule to which they are attached. For example, fluoro is a strongly electronegative group but it has a small Van der Waals Radius. When an organic molecule comprises a fluorine atom, therefore, the fluorine atom induces a dipole moment without making the molecule polar. Also, while one fluorine atom is hydrophilic the presence of multiple fluorine atoms, for example in a —$CF_3$, —$OCF_3$ or —$SCF_3$ group, can produce a group that is strongly lipophilic. Fluoro groups are capable of forming hydrogen bonds although these hydrogen bonds are weaker than hydrogen bonds to hydroxy groups. It is also of note that the strength of the C—F bond exceeds that of the C—H bond.

The properties of a fluoro group mean that its presence in a chemical product, for example a biologically active molecule, can offer various advantages. In a biologically active molecule fluorination can affect lipophilicity log $\pi$, resulting in an increase in the rate of absorption and transport of the molecule in vivo. Fluorination can also influence the acidity or basicity of neighbouring sites on a molecule (Hammett constant $\sigma$). Further, fluorination can increase oxidative stability against enzymatic attack; the presence of fluorine can reduce toxicity by metabolic stabilisation and enable drugs to exhibit a broader range of in vivo activity. It can also enable a special mode of action to a species, for example, producing a suicide substrate. The process of the present invention as defined above allows one to introduce a fluoro group into a molecule to control one or more of these properties of a biologically active compound.

Fluorination of biologically active compounds is now common in the pharmaceutical industry. Indeed, from 20-30% of all drugs currently on the market are fluorinated. Fluoro groups also appear in artificial blood substitutes, respiratory fluids and for compositions for use in clinical imaging. However, the use of fluorinated products is not by any means confined to the pharmaceutical industry. For example, fluorinated products are also used in the agrochemical industry and the electronics industry. In electronics products, for instance, fluoro groups influence molecular conformation in products used in liquid crystal displays and fluorinated fluororesists are used in connection with integrated electronic circuits.

The process of the present invention as defined above provides compounds that can be transformed further into useful chemical products. In one embodiment, such chemical products are biologically active molecules.

When producing a chemical product with a fluoro group in it, it is generally preferable either to introduce the fluoro group in the molecule at a late stage or to incorporate it via reaction with a building block in which the fluoro group has already been introduced. Thus, in one embodiment the present invention provides a process for producing a compound that can serve as a building block in the synthesis of a desired chemical product.

In another embodiment the present invention provides a process which is the final step in producing a desired chemical product, or which produces a synthetic intermediate from which the final desired chemical product can be prepared quickly and/or easily. In this embodiment the late introduction of the fluoro group makes possible certain applications for the resulting products. For example, final products which are suitable for administration to a human or animal body may be useful as imaging agents or molecular probes. Such compounds may have applications in, for instance, positron emission tomogrophy (PET). In this case the fluorine atom introduced in the process of the invention is an $^{18}F$ atom, which decays by positron emission and serves as a label. This embodiment is particularly useful when applied to biologically active molecules that have been designed to target specific biological sites.

When the label is $^{18}$F, the short half-life of $^{18}$F (110 minutes) means that the fluorinated derivative must be prepared on the day of its clinical use and the reaction steps used to produce it should be optimised for speed, with yield as a secondary consideration. Sources of "$^{18}$F$^+$" are rare, but may be used as a source of electrophilic $^{18}$F in a process of the present invention as defined above to add an $^{18}$F label to a compound of formula (I). $^{18}$F-Selectfluor is an example of a source of electrophilic $^{18}$F.

PET images may be acquired from about 5 minutes after administration until about 8 hours after administration. The maximum period in which images may be acquired is determined by 3 factors: the physical half-life of $^{18}$F (110 minutes); the sensitivity of the detectors and the size of the dose administered. Those of skill in the art can adjust these factors to permit the acquisition of images at an appropriate time. Details of imaging procedures are well known.

The process of the present invention as defined above can be used to prepare compounds that can serve as valuable synthetic intermediates and which provide numerous opportunities for subsequent functional manipulation of, for example, the double bond that appears in the product, or at any of the other functional groups that may be present. The reactivity of allylic fluorides is described, for example, by Thibaudeau, S.; Fuller, R.; Gouverneur, V. in *Org. Biomol. Chem.* 2004, 2, 1110-1112.

For example, in one embodiment the present invention provides a process for the fluorolactonisation of allylsilanes featuring a carboxylic acid group to produce silylated fluorolactones (variants (b) and (c) wherein Nu is —C(O)O—) which are advanced precursors of fluorinated analogues of various carbohydrates.

In another embodiment formula (I) is substituted such that it contains a group —C(O)X, wherein X is a group that can be subsequently replaced with a hydroxy group to create the corresponding carboxylic acid. This group comprising X typically appears in the group $R^7$, in a substituent of the carbocyclic or heterocyclic group that can be represented by $R^6$ and $R^7$, together with the carbon atoms to which they are attached, or in a substituent of the carbocyclic or heterocyclic group that can be represented by $R^5$ and $R^8$, together with the $C_3$ moiety that links $R^5$ and $R^8$. More typically, this group comprising X appears in the group $R^7$.

In a typical embodiment of the present invention as defined above, the allyl silane of formula (I) as defined above is a chiral allyl silane, which is present in a substantially enantiomerically pure form, and R7 in formula (I) features a carboxylic acid group. The enantiopure chiral allylsilanes can be generated by a cross-metathesis coupling of allyltrimethylsilane with the corresponding enantiopure deconjugated carboxylic acid derivative. To prepare these enantiopure α-functionalized building blocks one can use Evans-type oxazolidinones as the chiral auxiliaries.

In a further embodiment, the present invention provides a process of preparing more elaborated second-generation difluorinated building blocks in a cross metathesis reaction of a product of the process of the invention as defined above. When carried out on homochiral compounds produced by the process of the present invention as defined above such a reaction can be used to produce compounds with double the number of stereogenic centres. Thus, for example a di-fluorinated compound with four chiral centres can be prepared from a product of the process of the invention as defined above containing two chiral centres. In one embodiment the cross metathesis coupling step can be made intermolecular by the temporary attachment of the two molecules of the compound that are to be reacted together to a divalent tethering group. For example, when the compound that is to be reacted has an —OH group, or has a group that can be easily converted into an —OH group (such as a —C(O)OH group), a silicon-tethered approach can be used. Silicon-tethered ring closing metathesis coupling reactions are described in, for example Hoye, T. R.; Promo, M. A. *Tetrahedron Lett.* 1999, 40, 1429-1432.

The use of this approach is not, however, confined to cross metathesis reactions in which the two molecules being coupled are the same. Accordingly, the present invention also provides a cross metathesis coupling reaction of the same type as described in the previous paragraph, except that the moiety to which the compound in question is to be tethered already has attached to it another derivative of different structure, before it is introduced to the compound in question. Typically this other derivative also features stereocentres and is homochiral. This other derivative may, for instance, be an alternative product that has been produced by the process of the present invention as defined above.

Typically, the cross metathesis coupling reaction of the compounds produced by the process of the invention as defined above are carried out on homochiral starting compounds. This can enable control of the E/Z geometric stereoisomerism in the product.

In one embodiment the fluorination reagent used in the process of the present invention as defined above can also advantageously react with a separate part of the compound in formula (I). For example, when $R^7$ is CH(N(C(O)OC (CH$_3$)$_3$)R$^{13}$)CH$_2$OR$^{13}$ wherein the two $R^{13}$ groups together represent a group —C(CH$_3$)$_2$—, then that group $R^7$ reacts with the fluorination reagent to produce the corresponding group CH(NH(C(O)OC(CH$_3$)$_3$))CH$_2$OH. Typically this reaction is carried out wherein the starting compound is present in a substantially enantiomerically pure form. It is typical for this reaction to be carried out on starting compounds wherein $R^1$, $R^2$ and $R^3$ are methyl, $R^4$, $R^5$, $R^6$ and $R^8$ are hydrogen. Such a reaction offers the advantage of a product with functional groups that may also serve as useful sites for subsequent manipulation of the product as a building block, without the need for an additional reaction to yield those groups in a separate step.

The process of the present invention, and suitable methods for producing the starting materials for use in the process of the present invention, will be further described in the Examples which follow:

EXAMPLES

General Information $^1$H NMR spectra were recorded in deuterated solvents using Bruker DPX200, DPX400, AMX500, AV400 and AVC500 spectrometers, calibrated using residual undeuterated solvent as an internal reference. NOESY spectra were recorded in deuterated chloroform (unless otherwise stated) on a Bruker AV500 or a Bruker DRX500 spectrometer. $^{13}$C NMR spectra were recorded in deuterated solvents using Bruker DPX200, DPX400, AV400, AV500 and AVC500 spectrometers. $^{19}$F spectra were recorded on a AV400 spectrometer. Chemical shifts (δ) are quoted in parts per million (ppm) and coupling constants (J) are measured in hertz (Hz). The following abbreviations are used to describe multiplicities s=singlet, d=doublet, t=triplet, q=quartet, b=broad, m=multiplet. NMR were processed in either MestRe-C or ACD/SpecManager. IUPAC names were obtained using the ACD/I-lab service.

Mass spectra were recorded on Micromass GCT (CI), V.G. Masslab 20-250 (wherein direct chemical ionisation (CI+) was used, with ammonia being the ionising species as the internal reference or a Micromass GCT in Chemical Ionisation ($NH_3$, $CI^+$) or Electron Impact (EI)).Autospec-oaT of instruments or Micromass LCT.

Optical rotations were determined on a Perkin Elmer 241 polarimeter in a 1 dm cell. $[\alpha]_D$ values are given in $10^{-1}$ deg $cm^2$ $g^{-1}$. IR spectra were recorded as thin films on KBr discs or NaCl plates in solution in $CHCl_3$ on a Bruker Tensor 27 FT-IR spectrometer or a Paragon 1000 FT-IR spectrometer. Absorptions are measured in wavenumbers and only peaks of interest are reported.

All reactions requiring anhydrous conditions were conducted in dried apparatus under an inert atmosphere of argon or nitrogen. Solvents were dried and purified before use according to standard procedures. All reactions were monitored by TLC using Merck Kiesegel 60 $F_{254}$ plates. Visualisation of the reaction components was achieved using U.V fluorescence (254 nm) and $KMnO_4$ stain. Column chromatography was carried out over Merck silica gel C60 (40-60 μm).

Flash column chromatographies were performed on silica gel using the method of Still (Still, W.; Kahn, M.; Mitra, A., *J. Org. Chem.* 1978, 43). Thin-layer chromatographies were performed on 1 mm×4 cm×6 cm silica gel plates.

Melting Points were recorded on a Reichert-Koffler block and are uncorrected.

Example 1

(4R)-3-((E)-2-butenoyl)-4-(phenylmethyl)-2-oxazolidinone

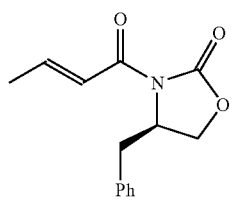

To a stirred solution of (R)-4-benzyl-2-oxazolidinone (5 g, 28.2 mmol) in THF (94 mL) at −78° C. was added 1 eq of n-BuLi (2.3 M, 12.26 mL). After 15 min 1.1 eq of crotonyl chloride (31 mmol, 2.97 mL) was added directly to the solution. The solution was allowed to stir for 30 min at −78° C., then 15 min at 0° C. The reaction was quenched with saturated $NH_4Cl$ solution then extracted with ether. The solvents were removed in vacuo and the crude product recrystallised from hexane:ethylacetate to yield a white solid (10.6 g, 77%); $^1$H NMR (400 MHz, $CDCl_3$): δ=7.18-7.36 (m, 7H), 4.74 (m, 1H), 4.1-4.14 (m, 2H), 3.34 (dd, J=3.3, 13.4, 1H), 2.80 (dd, J=9.6, 13.4, 1H), 1.99 (d, J=5.3); $^{13}$C NMR (100 MHz, $CDCl_3$): δ=164.9, 153.4, 146.9, 135.4, 129.4, 128.9, 127.3, 121.9, 66.1, 55.3, 37.9, 18.5; IR ($CHCl_3$): v 1780 $cm^{-1}$; MS (CI($NH_3$)): m/z 246 (M+H$^+$); $[\alpha]_D^{23}$ =−70.6° (c 0.5, $CHCl_3$).

Known compound: Evans, D. A.; Chapman, K. T.; Bisaha, J. *J. Am. Chem. Soc.* 1984,106, 4261-4263.

Example 2

(4R)-4-benzyl-3-[(2R)-2-benzylbut-3-enoyl]-1,3-oxazolidin-2-one

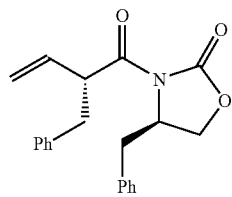

To a stirred solution of diisopropylamine (20.46 mmol, 2.85 mL) in THF (73 mL) at −78° C. was added n-BuLi (2.3 M, 8.89 mL). After 10 minutes HMPA (20.46 mmol, 3.5 mL) was added and the mixture stirred for 30 minutes at −78° C. (4R)-3-((E)-2-butenoyl)-4-(phenylmethyl)-2-oxazolidinone (18.6 mmol, 4.56 g) in THF (36 mL) was added at −78° C. followed 15 minutes later by benzyl bromide (55.8 mmol, 6.6 mL). After 20 minutes the reaction was allowed to warm to −10° C. and stirred at this temperature for 90 minutes. Dilute HCl was added and the aqueous layer extracted with ether. The combined organic phases were washed with saturated NaCl solution, dried ($MgSO_4$), filtered and the solvent removed in vacuo to yield an orange oil. The crude product was purified by column chromatography to yield a white solid (3.5 g, 56%); $^1$H NMR (400 MHz, $CDCl_3$): δ=7.0-7.34 (m, 10H), 5.91-6.1 (m, 1H), 5.15-5.25 (m, 2H), 4.92 (q, 1H), 4.65 (m, 1H), 4.11-4.17 (m, 1H), 4.06-4.10 (dd, J=2.7, 9.1, 1H), 3.27 (dd, J=8.6, 13.4, 1H), 3.02 (dd, J=3.3, 13.4), 2.92 (dd, J=6.8, 13.6, 1H), 2.57 (dd, J=9.1, 13.6, 1H); $^{13}$C NMR (100 MHz, $CDCl_3$): δ=173.4, 152.9, 138.6, 135.4, 135.0, 129.5, 129.4, 128.9, 128.3, 127.3, 126.5, 118.4, 65.8, 55.1, 49.1, 38.6, 37.6; IR ($CHCl_3$): v 3424, 2255, 1779, 1696, 1636, 1497, 1455, 1386, 1212, 1104 $cm^{-1}$; MS (CI($NH_3$)): m/z 336 (M+H$^+$); HMRS required for $C_{21}H_{22}NO_3$ ([M]$^+$) 336.1604 found 336.1599; $[\alpha]_D^{23}$=−67.8° (c, 1 $CHCl_3$); Mp 86-88° C.

Single-crystal X-ray diffraction report for (4R)-4-benzyl-3-[(2R)-2-benzylbut-3-enoyl]-1,3-oxazolidin-2-one, $C_{21}H_{21}NO_3$:

Crystals of (4R)-4-benzyl-3-[(2R)-2-benzylbut-3-enoyl]-1,3-oxazolidin-2-one were grown by recrystallisation from ethyl acetate. A large single crystal was cut to give a fragment having dimensions approximately 0.30×0.36×0.36 mm. This was mounted on a glass fibre using perfluoropolyether oil and cooled rapidly to 150K in a stream of cold N2 using an Oxford Cryosystems CRYOSTREAM unit. Diffraction data were measured using an Enraf-Nonius KappaCCD diffractometer (graphite-monochromated MoKαxradiation, λ=0.71073 Å). Intensity data were processed using the DENZO-SMN package (Z. Otwinowski and W. Minor, *Processing of X-ray Diffraction Data Collected in Oscillation Mode, Methods Enzymol.,* 1997, 276, Eds C. W. Carter and R. M. Sweet, Academic Press). Examination of the systematic absences of the intensity data showed the space group to be either P 21 or P 21/m. The structure was solved in the space group P 21 using the direct-methods program SIR92 (A. Altomare, G. Cascarano, G. Giacovazzo, A. Guagliardi , M. C. Burla, G. Polidori and M. Camalli, *J. Appl. Cryst.* 1994, 27, 435.), which located all non-hydrogen atoms. Subsequent full-matrix least-squares refinement was carried out using the CRYSTALS program suite (CRYSTALS Issue 12, P. W. Betteridge, J. R. Cooper, R. I. Cooper, K. Prout and D. J. Watkin, *J. Appl. Cryst.*, 2003, 36, 1487). Coordinates and anisotropic thermal parameters of all non-hydrogen atoms were refined. Hydrogen atoms were positioned geometrically after each cycle of refinement. A 3-term Chebychev polynomial weighting scheme was applied. Refinement converged satisfactorily to give R=0.0305, wR=0.0303. A thermal ellipsoid plot (ORTEP-3 (ORTEP-3 v. 1.0.2, C. K. Johnson and M. K. Burnett, 1998.)) at 40% probability was produced.

A summary of crystallographic data now follows: Crystal identification: ARC851; Chemical formula $C_{21}H_{21}NO_3$; Formula weight: 335.40; Temperature (K): 150; Wavelength (Å): 0.71073; Crystal system: Monoclinic; Space group: P $2_1$; a (Å): 9.5701(3); b (Å): 10.0377(3); c (Å): 9.7704(3); α(°): 90; β(°): 111.8904(15); λ(°): 90; Cell volume (Å$^3$): 870.89(5); Z: 2; Calculated density (Mg/m$^3$): 1.279; Absorption coefficient (mm$^-$): 0.085; $F_{000}$: 356; Crystal size (mm): 0.30×0.36×0.36; Description of crystal: Colourless fragment; Absorption correction: Semi-empirical from equivalent reflections; Transmission coefficients (min,max): 0.96, 0.97; θ range for data collection (°): $5.0 \leq \theta \leq 27.5$; Index ranges: $-12 \leq h \leq 11$, $0 \leq k \leq 12$, $0 \leq l \leq 12$; Reflections measured: 8985; Unique reflections 2078; $R_{int}$: 0.050; Observed reflections: (I>3σ(I)) 1540; Refinement method: Full-matrix least-squares on F; Parameters refined: 226; Weighting scheme: Chebychev 3-term polynomial; Goodness of fit: 1.1786; R: 0.0305; wR: 0.0303; Residual electron density (min,max) (e Å$^{-3}$) −0.16, 0.14.

Example 3

(4R)-4-benzyl-3-[(2R,3E)-2-benzyl-5-(trimethylsilyl)pent-3-enoyl]-1,3-oxazolidin-2-one

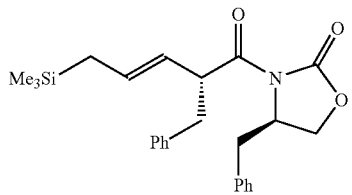

To a solution of (4R)-4-benzyl-3-[(2R)-2-benzylbut-3-enoyl]-1,3-oxazolidin-2-one (3.42 mmol, 1.10 g) and allyltrimethylsilane (10.26 mmol, 1.63 mL) in DCM (50 mL) at reflux was added 5 mol % of Grubbs' second generation catalyst (145 mg). After 68 hrs the solvent was removed in vacuo. The crude product was purified by column chromatography to yield a white solid. (1.37 g, 95%); $^1$H NMR (400 MHz, CDCl$_3$): δ=7.0-7.32 (m, 10H), 5.62 (dt, J=8.1, 15.2, 1H), 5.29-5.36 (m, 1H), 4.82 (m, 1H), 4.61 (m, 1H), 4.01-4.15 (m, 2H), 3.22 (dd, J=8.3, 13.4, 1H), 3.02 (dd, J=3.3, 13.3, 1H), 2.85 (dd, J=6.1, 13.4, 1H), 2.57 (dd, J=9.1, 13.4, 1H) 1.42 (d, J=8.1, 1H) −0.08 (s, 9H); $^{13}$C NMR (100 MHz, CDCl$_3$): δ=174.2, 138.9, 135.1, 131.6, 129.4, 128.9, 128.3, 127.2, 126.3, 124.9, 65.7, 55.2, 48.2, 38.9, 37.6, 23.1, −2.1; IR (CHCl$_3$): v 3444, 2955, 1767, 1694, 1454, 1393, 1248, 1182 cm$^{-1}$; MS (CI(NH$_3$)): m/z 422 (M+H$^+$); HMRS required for $C_{25}H_{32}NO_3Si$ ([M]$^+$) 422.2158 found 422.2151; $[\alpha]_D^{23}$=117.8° (c, 0.5 CHCl3); Mp 132-135° C.

Example 4

(2R)-2-benzyl-5-(trimethylsilyl)pent-3-enoic acid

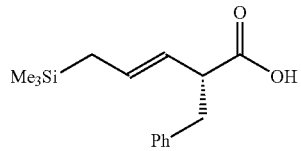

To a solution of (2R)-2-benzylbut-3-enoic acid (1.4 mmol, 250 mg) and allyltrimethylsilane (4.2 mmol, 0.67 mL) in DCM (3 mL) at reflux was added Hoveyda-Grubbs second generation catalyst (5 mol %, 44 mg). The reaction was allowed to stir at reflux for 50 hrs. The solvent was removed in vacuo. The crude product was purified by column chromatography (184 mg, 50%). $^1$H NMR (400 MHz, CDCl$_3$): δ=7.15-7.30 (m, 5H), 5.48-5.56 (m, 1H), 5.26 (dd, J=8.8, 15.2, 1H), 3.30 (m, 1H), 3.10 (dd, J=7.1, 13.9, 1H), 2.80 (dd, J=7.8, 13.6, 1H), 1.43 (d, J=8.3, 2H), −0.08 (s, 9H); $^{13}$C NMR (125 MHz, CDCl$_3$): δ=179.5, 138.7, 131.4, 130.1, 129.1, 129.0, 128.3, 126.4, 126.3, 124.3, 123.7, 50.8, 38.5, 22.9, 18.9, −2.08; IR (CHCl$_3$): v 2955, 1797; HMRS required for $C_{15}H_{21}O_2Si$ ([M−H]$^-$) 261.1311 found 261.1318; $[\alpha]_D^{21}$=−39.4 (c, 0.5, CHCl$_3$).

Example 5

(4R)-4-benzyl-3-[(2S,3R)-2-benzyl-3-fluoropent-4-enoyl]-1,3-oxazolidin-2-one

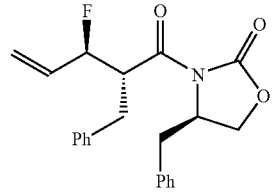

To a solution of (4R)-4-benzyl-3-[(2R,3E)-2-benzyl-5-(trimethylsilyl)pent-3-enoyl]-1,3-oxazolidin-2-one (0.88 mmol, 370 mg) in CH$_3$CN (8 mL) was added [1-(chloromethyl)-4-fluoro-1,4-diazoniabicyclo[2.2.2]octane bis(tetrafluoroborate)] (referred to hereafter as Selectfluor) (0.88 mmol, 310 mg). The reaction was allowed to stir at RT for 48 hr. The solvent was removed in vacuo. The crude product was purified by column chromatography to yield a mixture of diastereoisomers de=10% (250 mg, 95%). $^1$H NMR (400 MHz, CDCl$_3$): δ=6.98-7.3 (m, 10H), 6.0 (m, 1H), 5.5 (dm, J=17, 1H), 5.42 (d, J=10.6, 1H), 5.1 (ddd, J=7.1, 8.1, 47.2, 1H), 4.85 (m, 1H), 4.64 (m, 1H), 3.98-4.12 (m, 2H), 2.84-3.0 (m, 3H), 2.2 (m, 1H); $^{13}$C NMR (100 MHz, CDCl3): δ=172.5, 152.9, 137.2, 135.1, 133.7, 133.6, 129.5, 129.3, 128.9, 128.5, 127.2, 126.8, 120.6, 120.5, 94.4 (d, J=175), 65.6, 55.1, 48.1 (d, J=21), 37.3 34.8 (d, J=6); $^{19}$F {$^1$H} NMR (376.5 MHz, CDCl3): δ=−175.7; IR (CHCl3): v 3444, 2957, 1645, 1367, 1235, 1205 cm$^{-1}$; $[\alpha]_D^{20}$=−18.4° (c, 0.5 CHCl$_3$); HMRS required for $C_{22}H_{23}NO_3F$ 368.1662 ([M+H$^+$]) found 368.1669.

Example 6

(4R)-4-benzyl-3-[(2S,3S)-2-benzyl-3-fluoropent-4-enoyl]-1,3-oxazolidin-2-one

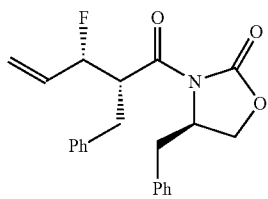

$^1$H NMR (400 MHz, CDCl$_3$): δ=6.92-7.31 (m, 10H), 6.05 (dddd, J=6.5, 10.6, 14.0, 17.2, 1H), 5.41-5.46 (m, 1H), 5.35-5.38 (m, 1H), 5.15 (dt, J=6.4, 47.7, 1H), 4.75-4.84 (m, 1H), 4.59-4.64 (m, 1H), 4.11 (m, 1H), 4.03 (dd, J=2.7, 9.1, 1H), 3.18-3.15 (m, 2H), 2.90 (dd, J=3.3, 13.5, 1H), 2.33 (dd, J=9.2, 13.5, 1H); $^{13}$C NMR (100 MHz, CDCl$_3$): δ=171.6 (d, J=6.7), 153.0, 138.0, 134.9, 134.2 (d, J=20.2), 129.3, 129.2, 128.9, 128.4, 127.2, 126.5, 119.4 (d, J=12.1), 94.5 (d, J=175.2), 65.7, 55.0, 49.0 (d, J=23.3), 37.2, 33.6 (d, J=4.6); $^{19}$F NMR (376.5 MHz, CDCl$_3$): δ –184.3 (dtd, J$_{HF}$=2.8, 14.7, 47.7). MS ESI m/z 368 [M+H]$^+$ HR-MS Calc for C$_{22}$H$_{22}$NO$_3$F 368.1662, Found 368.1656, [α]$_D^{20}$=−7.8 (c=1, CHCl$_3$).

Single-crystal X-ray diffraction report for (4R)-4-benzyl-3-[(2S,3R)-2-benzyl-3-fluoropent-4-enoyl]-1,3-oxazolidin-2-one, C$_{22}$H$_{22}$FNO$_3$:

Crystals of (4R)-4-benzyl-3-[(2S, 3R)-2-benzyl-3-fluoropent-4-enoyl]-1,3-oxazolidin-2-one were grown by recrystallisation from ethyl acetate. A single crystal having dimensions approximately 0.06×0.08×0.40 mm was mounted on a glass fibre using perfluoropolyether oil and cooled rapidly to 150K in a stream of cold N$_2$ using an Oxford Cryosystems CRYOSTREAM unit. Diffraction data were measured using an Enraf-Nonius KappaCCD diffractometer (graphite-monochromated MoKr$_\alpha$diation, λ=0.71073 Å). Intensity data were processed using the DENZO-SMN package (Z. Otwinowski and W. Minor, *Processing of X-ray Diffraction Data Collected in Oscillation Mode, Methods Enzymol.*, 1997, 276, Eds C. W. Carter and R. M. Sweet, Academic Press.). Examination of the systematic absences of the intensity data showed the space group to be P 2$_1$ 2$_1$ 2$_1$. The structure was solved using the direct-methods program SIR92 (A. Altomare, G. Cascarano, G. Giacovazzo, A. Guagliardi, M. C. Burla, G. Polidori and M. Camalli, *J. Appl. Cryst.* 1994, 27, 435.), which located all non-hydrogen atoms. Subsequent full-matrix leastsquares refinement was carried out using the CRYSTALS program suite (CRYSTALS Issue 12, P. W. Betteridge, J. R. Cooper, R. I. Cooper, K. Prout and D. J. Watkin, *J. Appl. Cryst.*, 2003, 36, 1487.). Coordinates and anisotropic thermal parameters of all non-hydrogen atoms were refined. Hydrogen atoms were positioned geometrically after each cycle of refinement. A 3-term Chebychev polynomial weighting scheme was applied. Refinement converged satisfactorily to give R=0.0330, wR=0.0372. A thermal ellipsoid plot (ORTEP-3 (ORTEP-3 v. 1.0.2, C. K. Johnson and M. K. Burnett, 1998.)) at 40% probability was produced.

A summary of crystallographic data now follows: Crystal identification: ARC986; Chemical formula: C$_{22}$H$_{22}$FNO$_3$; Formula weight: 367.42; Temperature (K): 150; Wavelength (Å): 0.71073; Crystal system: Orthorhombic; Space group: P 2$_1$ 2$_1$ 2$_1$; a (Å): 6.3654(2); b (Å): 17.2322(5); c (Å): 17.8046 (7); α(°): 90; β(°): 90; γ(°) 90; Cell volume (Å$^3$): 1952.98 (11); Z: 4; Calculated density (Mg/m$^3$) 1.250; Absorption coefficient (mm$^{-1}$): 0.089; F$_{000}$ 776; Crystal size (mm): 0.06× 0.08×0.40; Description of crystal: Colourless needle; Absorption correction: Semi-empirical from equivalent reflections; Transmission coefficients (min,max): 0.97, 0.99; θ range for data collection (°): 5.0≦θ≦27.5; Index ranges: −8≦h≦8, −22≦k≦22, −23≦l≦23; Reflections measured: 12113; Unique reflections: 2562; R$_{int}$: 0.051; Observed reflections (I>3σ(I)): 1658; Refinement method: Full-matrix least-squares on F; Parameters refined: 244; Weighting scheme: Chebychev 3-term polynomial; Goodness of fit: 1.1252; R: 0.0330; wR: 0.0372; Residual electron density (min,max) (e Å$^{-3}$): −0.14, 0.17.

Example 7

(2S,3R)-2-benzyl-3-fluoropent-4-enoic acid

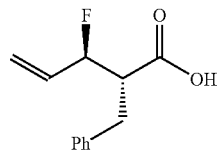

To a solution of anti-(4R)-4-benzyl-3-[2-benzyl-3-fluoropent-4-enoyl]-1,3-oxazolidin-2-one (1.22 mmol, 450 mg) in THF (22 mL) and H$_2$O (7.2 mL) at 0° C. was added H$_2$O$_2$ (50% in water, 9.79 mmol, 0.28 mL) followed by LiOH.H$_2$O (2.45 mmol, 103 mg). The mixture was allowed to warm to room temperature and stirred until no starting material was present (2 hr). The solution is cooled to 0° C. and quenched with excess saturated Na$_2$SO$_3$ solution. After evaporation of the THF, the basic solution is extracted with DCM. The solution is then treated with 1M HCl until ~pH2 and then extracted with ethyl acetate. The crude oil is purified by column chromatography to yield a colourless oil (95%, 240 mg); $^1$H NMR (400 MHz, CDCl$_3$): δ=7.14-7.34 (m, 5H), 5.89-6.03 (m, 2H), 5.10 (dt, J=6.8, 47.0, 1H), 2.85-3.08 (m, 3H); $^{13}$C NMR (100 MHz, CDCl$_3$): δ=177.9, 137.6, 133.2 (d, J=19), 128.9, 128.6, 126.8, 120.3 (d, J=12), 93.6 (d, J=175), 52.7 (d, J=22), 33.5 (d, J=5); $^{19}$F {$^1$H} NMR (376.5 MHz, CDCl$_3$): δ=−175.7; IR (CDCl$_3$): v 3418, 1714, 1496, 1429, 1224, 988, 699; HMRS required for C$_{12}$H$_{12}$O$_2$F ([M–H]$^-$) 207.0821 found 207.0817; [α]$_D^{21}$=+60.0 (c, 0.5, CHCl$_3$).

Example 8

(2S, 3S)-2-benzyl-3-fluoropent-4-enoic acid

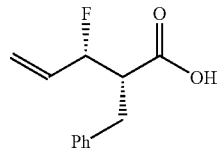

To a solution of syn-(4R)-4-benzyl-3-[2-benzyl-3-fluoropent-4-enoyl]-1,3-oxazolidin-2-one (0.26 mmol, 94 mg) in THF (6 mL) and H$_2$O (2 mL) at 0° C. was added H$_2$O$_2$ (50% in water, 2.05 mmol, 0.6 mL) followed by LiOH.H$_2$O (0.51 mmol, 22 mg). The mixture was allowed to warm to room temperature and stirred until no starting material was present (2 hr). The solution is cooled to 0° C. and quenched with excess saturated Na$_2$SO$_3$ solution. After evaporation of the THF, the basic solution is extracted with DCM. The solution is then treated with 1 M HCl until ~pH 2 and then extracted with ethyl acetate. The crude oil was purified by column chromatography to yield a colourless oil (90%, 53 mg); $^1$H NMR (400 MHz, CDCl$_3$): δ=7.19-7.31 (m, 5H), 5.97 (dddd, J=6.3, 10.6, 14.4, 17.1, 1H), 5.42-5.47 (m, 1H), 5.36-5.39 (m, 1H), 5.02-5.17 (m, 1H), 3.00-3.06 (m, 3H); $^{13}$C NMR (100 MHz, CDCl$_3$): δ=176.1, 138.0, 133.3 (d, J=19.6), 128.9, 128.5, 126.7, 119.6 (d, J=11.8), 92.6 (d, J=175.3), 52.3 (d, J=23.3), 33.27; $^{19}$F NMR (376.5 MHz, CDCl3) δ −178.3 to −178.5 (m); MS m/z 207.07 ([M−H]$^−$); [α]$_D^{21}$=+20.0 (c, 0.15, CHCl$_3$).

Example 9

Synthesis of (2S, 3R)-2-benzyl-3-fluoropent-4-enoic acid and (2S, 3S)-2-benzyl-3-fluoropent-4-enoic acid (Examples 7 & 8) from the allylsilane of Example 3

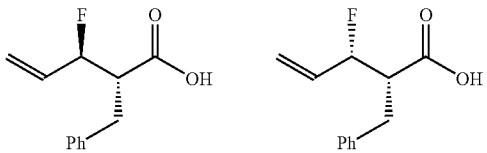

To a solution of (2R)-2-benzyl-5-(trimethylsilyl)pent-3-enoic acid in (0.62 mmol, 163 mg) in CH$_3$CN (3 mL) was added Selectfluor (0.68 mmol, 242 mg). The reaction was allowed to stir at RT for 48 hrs. After column chromatography an inseparable mixture of diastereoisomers was obtained (61%, 79 mg), anti/syn 1:1.

Example 10

(4R)-4-benzyl-3-[(2R)-2-methylbut-3-enoyl]-1,3-oxazolidin-2-one

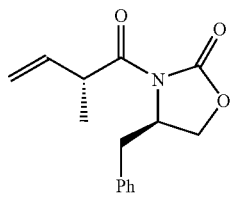

To a stirred solution of diisopropylamine (4.48 mmol, 0.63 mL) in THF (16 mL) at −78° C. was added n-BuLi (1 M, 4.48 mL). After 10 minutes HMPA (4.48 mmol, 0.78 mL) was added and the mixture stirred for 30 minutes at −78° C. (4R)-3-((E)-2-butenoyl)-4-(phenylmethyl)-2-oxazolidinone (4.08 mmol, 1 g) in THF (8 mL) was added at −78° C. followed 15 minutes later by methyl iodide (12.24 mmol, 0.76 mL). After 20 minutes the reaction was allowed to warm to −10° C. and stirred at this temperature for 90 minutes. Dilute HCl was added and the aqueous layer extracted with ether. The combined organic phases were washed with saturated NaCl solution, dried (MgSO$_4$), filtered and the solvent removed in vacuo to yield an orange oil (de crude=42%). The two diastereoisomers were separated by column chromatography. The major diastereoisomer was obtained as a colourless oil (476 mg, 45%). Major diastereoisomer (4R)-4-benzyl-3-[(2R)-2-methylbut-3-enoyl]-1,3-oxazolidin-2-one: $^1$H NMR (400 MHz, CDCl$_3$): δ=7.19-7.37 (m, 5H), 5.99 (ddd, J=7.6, 10.1, 17.2), 5.18-5.23 (m, 1H), 5.13-5.16 (m, 1H), 4.63-4.7 (m, 1H), 4.43-4.5 (m, 1H), 4.16-4.23 (m, 2H), 3.29 (dd, J=3.3, 13.4, 1H), 2.79 (dd, J=9.6, 13.4, 1H), 1.35 (d, J=7.6, 3H); $^{13}$C NMR (100 MHz, CDCl$_3$): δ=174.8, 152.9, 136.9, 135.2, 129.4, 128.9, 127.3, 116.6, 66.0, 55.4, 41.7, 37.9, 17.2; IR (CHCl$_3$): ν 1781, 1217, 756; HMRS required for C$_{15}$H$_{18}$NO$_3$ ([M+H]$^+$) 260.1287 found 260.1273; [α]$_D^{21}$=−87.3 (c, 0.5, CHCl3). Minor diastereoisomer (4R)-4-benzyl-3-[(2S)-2-methylbut-3-enoyl]-1,3-oxazolidin-2-one: $^1$H NMR (400 MHz, CDCl$_3$): δ=7.18-7.37 (m, 5H), 6.0 (ddd, J=7.6, 10.4, 17.9, 1H), 5.25-5.3 (m, 1H), 5.18-5.22 (m, 1H), 4.67-4.73 (m, 1H), 4.45-4.54 (m, 1H), 4.15-4.24 (m, 2H), 3.26 (dd, J=3.0, 13.1, 1H), 2.76 (dd, J=9.3, 13.4, 1H), 1.32 (d, J=7.6, 3H); $^{13}$C NMR (100 MHz, CDCl$_3$): δ=174.6, 152.9, 136.9, 135.1, 129.4, 128.9, 127.3, 116.7, 65.9, 55.2, 41.4, 37.7, 16.6; TOF MS CI$^+$m/z 260.121 [M+H]$^+$; [α]$_D^{21}$=−28.9 (c, 0.65, CHCl3); Mp 72-74° C. Relative stereochemistry assigned by analogy with (4R)-4-benzyl-3-[2-benzyl-3-fluoropent-4-enoyl]-1,3-oxazolidin-2-one and literature ref: A. Dobarro, D. Velasco, *Tetrahedron* 1996, 52, 13525-13530.

Example 11

(4R)-4-benzyl-3-[(2R,3E)-2-methyl-5-(trimethylsilyl)pent-3-enoyl]-1,3-oxazolidin-2-one

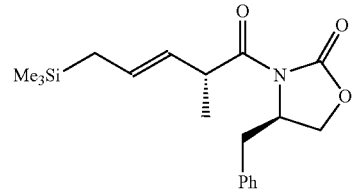

To a solution of (4R)-4-benzyl-3-[(2R)-2-methylbut-3-enoyl]-1,3-oxazolidin-2-one (0.65 mmol, 170 mg) and allyltrimethyl silane (1.9 mmol, 0.31 mL) in DCM (2 mL) at reflux was added 5 mol % of Grubbs' second generation catalyst (28 mg). After 72 hrs the solvent was removed in vacuo. The crude product was purified by column chromatography to a colourless oil. (83 mg, 77%) E/Z 3:1. NMR data of the mixture of E/Z isomers. $^1$H NMR (400 MHz, CDCl$_3$): δ=7.21-7.36 (m, 5H), 5.64 (dt, J=8.1, 15.4, 1H), 5.41-5.58, (m, 2 HZ) 5.32-5.39 (m, 1H), 4.68-4.78 (m, 1 HZ) 4.59-4.68 (m, 1H), 4.38-4.48 (m, 1H), 4.14-4.19 (m, 2H), 3.30 (dd, J=3.28, 13.14, 1H), 2.78 (dd, J=9.6, 13.14, 1H), 1.48-1.63 (m, 2 HZ), 1.46 (d, J=8.1, 2H), 1.31 (d, J=6.8, 3 HZ), 1.30 (d, J=6.8, 3H), 0.0 (s, 9 HZ), −0.02 (s, 9H); $^{13}$C NMR (100 MHz, CDCl$_3$): δ=175.5, 152.3, 135.4$_{Z\ or\ E}$, 135.3$_{Z\ or\ E}$, 129.7$_{Z\ or\ E}$, 129.5$_{Z\ or\ E}$, 128.9$_{Z\ or\ E}$, 128.1$_Z$, 127.3, 126.9, 126.1$_Z$, 66.03, 66.0$_Z$, 55.6, 55.5$_Z$, 40.9, 37.9, 37.8$_Z$, 35.8$_Z$, 22.9, 19.0$_Z$, 17.9, −1.8$_Z$, −1.9; IR (CHCl$_3$): ν 2955, 1783, 1699, 1454, 1381, 853; HMRS required for C$_{19}$H$_{27}$NO$_3$Si ([M+H]$^+$) 346.1838 found 346.1847; [α]$_D^{23}$=−131.6 (c, 2, CHCl$_3$).

Example 12

(4R)-4-benzyl-3-[(2S),(3R)-fluoro-2-methylpent-4-enoyl]-1,3-oxazolidin-2-one and (4R)-4-benzyl-3-[(2S),(3S)-fluoro-2-methylpent-4-enoyl]-1,3-oxazolidin-2-one

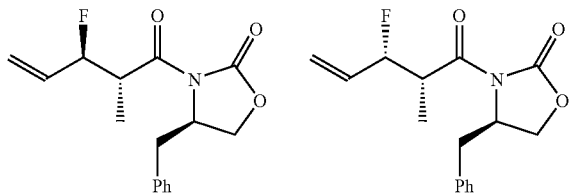

To a solution of (4R)-4-benzyl-3-[(2R,3E)-2-methyl-5-(trimethylsilyl)pent-3-enoyl]-1,3-oxazolidin-2-one (0.24 mmol, 84 mg) in $CH_3CN$ (2 mL) was added Selectfluor (0.26 mmol, 93 mg). The reaction was allowed to stir at RT for 48 hr. The solvent was removed in vacuo. The crude product was purified by column chromatography to yield a mixture of diastereoisomers anti/syn 1:1 (58 mg, 82%). Anti diastereoisomer $^1$H NMR (400 MHz, $CDCl_3$): δ=7.16-7.42 (m, 5H), 5.88-6.02 (m, 1H), 5.37-5.46 (m, 1H), 5.29-5.34 (m, 1H), 5.15 (dt, J=5.8, 47.0, 1H), 4.69 (m, 1H), 4.2 (m, 2H), 4.1 (m, 1H), 3.29 (dd, J=3.3, 13.4, 1H), 2.79 (dd, J=9.6, 13.4, 1H), 1.33 (d, J=7.1, 3H); $^{13}$C NMR (125 MHz, $CDCl^3$): δ=173.2, 153.1, 135.0, 133.9 (d, J=20), 129.4, 128.9, 127.4, 118.6 (d, J=12), 93.1 (d, J=174), 66.2, 55.4, 50.9, 42.6 (d, J=24), 37.7, 11.9 (d, J=6); $^{19}$F {$^1$H} NMR (376.5 MHz, $CDCl_3$): δ=−188.9; IR ($CHCl_3$): v 2950, 1779, 1700; HMRS required for $C_{16}H_{19}NO_3F$ ([M+H]$^+$) 292.1349 found 292.1360; $[α]_D^{23}$=−38.4 (c, 0.25, CHCl3). Syn diastereoisomer $^1$H NMR (400 MHz, $CDCl_3$): δ=7.18-7.4 (m, 5H), 5.8-6.0 (m, 1H), 5.39-5.51 (m, 2H), 5.14 (dt, J=7.8, 47.5, 1H), 4.74 (m, 1H), 4.23 (m, 2H), 4.12 (m, 1H), 3.28 (dd, J=3.3, 13.4, 1H), 2.82 (dd, J=9.6, 13.4, 1H), 1.18 (d, J=7.1, 3H); $^{13}$C NMR (125 MHz, $CDCl_3$): δ=173.9, 153.1, 135.1, 133.5 (d, J=24), 129.4, 128.9, 127.4, 120.8 (d, J=15), 94.8 (d, J=211), 66.3, 55.4, 42.1 (d, J=29), 37.8, 13.5 (d, J=9); $^{19}$F {$^1$H} NMR (376.5 MHz, $CDCl_3$): δ=−171.9; HMRS required for $C_{16}H_{19}NO_3F$ ([M+H]$^+$) 292.1349 found 292.1342; $[α]_D^{23}$=−45.7 (c, 1, $CHCl_3$); Mp 68-71° C. Relative stereochemistry of products assigned by analogy with the benzyl substituted allylic fluorides based on the $^{19}$F {$^1$H} NMR chemical shifts.

Example 13

(2S,3S)-2-benzyl-3-fluoropent-4-en-1-ol

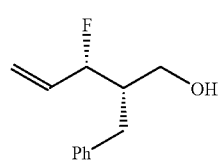

To a stirred suspension of $LiAlH_4$ (0.25 mmol, 10 mg) in THF (1 mL) at RT was added syn-2-benzyl-3-fluoropent-4-enoic acid (0.25 mmol, 52 mg) in THF (1 mL) dropwise. The reaction was allowed to stir for 14 hr at RT. After cooling to 0° C., water was added dropwise, followed by 5% NaOH. After stirring for 30 min the mixture was filtered through celite. The solution was then extracted with ethyl acetate. The combined organic extracts were washed then dried over $MgSO_4$ to yield a colourless oil (62%, 30 mg); $^1$H NMR (400 MHz, $CDCl_3$): δ=7.18-7.34 (m, 5H), 5.93-6.07 (m, 1H), 5.34-5.48 (m, 2H), 5.14 (dt, J=5.3, 47, 1H), 3.61-3.67 (m, 2H), 2.88 (dd, J=5.1, 13.9, 1H), 2.64 (dd, J=9.6, 13.9, 1H), 2.06-2.21 (m, 1H); $^{13}$C NMR (125 MHz, $CDCl_3$): δ=139.7, 134.7 (d, J=19), 129.1, 128.5, 126.2, 118.0 (d, J=13), 93.7 (d, J=170), 61.3 (d, J=3), 47.1 (d, J=20), 31.8 (d, J=6); $^{19}$F {$^1$H} NMR (376.5 MHz, $CDCl_3$): δ=−188.9; IR ($CHCl_3$): v 3383, 2930; HMRS required for $C_{12}H_{19}NOF$ ([M+NH4]$^+$) 212.1451 found 212.1448.

Example 14

1-Phenylhex-5-en-3-ol

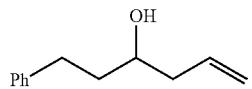

To a mixture of 3-phenylpropionaldehyde (1.06 mL, 8 mmol, 1 eq) and activated zinc (628 mg, 9.6 mmol, 1.2 eq) in THF (3.2 mL) at 0° C. was added one drop of allyl bromide. After the reaction was initiated, the remaining allyl bromide (total 0.831 mL, 9.6 mmol, 1.2 eq) was added slowly. The contents were stirred overnight at room temperature. After 20 hours the reaction was quenched with saturated aq. $NH_4Cl$ solution (15 mL), extracted with ether (3×20 mL) and the combined organic phases washed with brine (15 mL). The organic layer was dried over $MgSO_4$ and the solvent was removed under reduced pressure to give crude 1-phenyl-hex-5-en-3-ol as a yellow oil. Column chromatography (hexane:ether, 85:15, 80:20, 75:25) gave a colourless oil, (966 mg, 69% yield). $^1$H NMR (400 MHz, $CDCl_3$) δ 1.80-1.85 (m, 3H, $CC\underline{H}_2CH_2$, +$CO\underline{H}$), 2.19-2.26 (m, 1H, $CHOHC\underline{H}_2CH$), 2.33-2.39 (m, 1H, $CHOHC\underline{H}_2CH$) 2.69-2.76 (m, 1H, $PhC\underline{H}_2CH_2$), 2.82-2.89 (m, 1H, $PhC\underline{H}_2CH_2$), 3.69-3.74 (m, 1H, $C\underline{H}OH$), 5.16-5.19 (s, 1H, $CHC\underline{H}_2$ (cisH)), 5.19-5.20 (d, 1H, $CHC\underline{H}_2$ (trans H)), 7.21-7.26 (m, 3H, $\underline{Ph}CH_2$), 7.30-7.34 (m, 2H, $\underline{Ph}CH_2$); $^{13}$C NMR (100 MHz, $CDCl_3$) δ 32.0 ($PhC\underline{H}_2CH_2$), 38.4 ($CH_2C\underline{H}_2CH$), 42.0 ($CHOHC\underline{H}_2CH$), 69.9 ($\underline{C}HOH$), 118.1 ($CH\underline{C}H_2$), 125.7 (Ph), 128.4 (Ph), 128.5 (Ph), 134.6 ($\underline{C}HCH_2$), 142.0 (Ph); IR (v, cm$^{-1}$) 3385 (OH), 3027 (Ar), 2932 ($CH_2$), 1641 (CH=$CH_2$), 1496 (Ph), 916 (CH=$CH_2$); MS (GCT, Cl$^+$) m/z 194.2 [M+$NH_4$]$^+$ HRMS required for $C_{12}H_{20}NO$: 194.1545, found 194.1543.

Example 15

1-Phenyl-7-(trimethylsilyl)-hept-5-en-3-ol

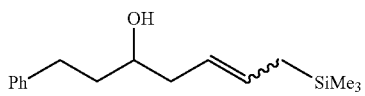

To a round-bottomed flask containing 1-phenyl-hex-5-en-3-ol (495 mg, 2.8 mmol, 1 eq) in DCM (12 mL) was added allyltrimethylsilane (1.79 mL, 11.2 mmol, 4 eq). Hoveyda-Grubbs' Catalyst (44 mg, 0.07 mmol, 0.025 eq) was subsequently added as a solid and left to stir at room temperature under an atmosphere of argon. After 72 hours a further equivalent of allyltrimethylsilane was added (0.445 mL, 2.78 mmol). After 7 days the reaction mixture was concentrated under reduced pressure to a dark brown oil. Column chromatography (hexane:ether, 100:0, 9:1, 85:15) gave 1-phenyl-7-(trimethylsilyl)-hept-5-en-3-ol as a colourless oil (445 mg, 61% yield). For major isomer E: $^1$H NMR (400 MHz, CDCl$_3$) δ 0.006 (s, 9H, SiMe$_3$), 1.47-1.49 (d, 2H, CH$_2$SiMe$_3$, J=8 Hz), 1.74-1.84 (mn, 2H, CH$_2$CH$_2$CHOH), 2.06-2.14 (m, 1H, CHOHCH$_2$CH), 2.20-2.31 (m, 1H, CHOHCH$_2$CH), 2.66-2.74 (m, 1H, PhCH$_2$), 2.79-2.86 (m, 1H, PhCH$_2$), 3.57-3.63 (m, 1H, CHOH), 5.21-5.28 (dt, 1H, CH$_2$CHCH, J=15.2 Hz, 8 Hz), 5.50-5.58 (dt, 1H, CH$_2$CHCH, J=15.2 Hz, 8 Hz), 7.18-7.24 (m, 3H, Ph), 7.27-7.31 (m, 2H, Ph); $^{13}$C NMR (100 MHz, CDCl$_3$) δ −2.0 (SiMe$_3$), 23.0 (CH$_2$SiMe$_3$), 32.1 (PhCH$_2$), 38.3 (PhCH$_2$CH$_2$), 41.0 (CHOHCH$_2$), 70.2 (CHOH), 123.8 (CHCH), 125.7 (Ph), 128.4 (Ph), 130.9 (CHCH), 142.2 (Ph). For minor isomer Z: $^1$H NMR (400 MHz, CDCl$_3$) δ 0.012 (s, 9H, SiMe$_3$), 1.47-1.49 (d, 2H, CH$_2$SiMe$_3$, J=8 Hz), 1.74-1.84 (m, 2H, CH$_2$CH$_2$CHOH), 2.06-2.14 (m, 1H, CHOHCH$_2$CH), 2.20-2.31 (m, 1H, CHOHCH$_2$CH), 2.66-2.74 (m, 1H, PhCH$_2$), 2.79-2.86 (m, 1H, PhCH$_2$), 3.64-3.69 (m, 1H, CHOH), 5.30-5.35 (dt, 1H, CH$_2$CHCH, J=10.4 Hz, 8 Hz), 5.61-5.66 (dt, 1H, CH$_2$CHCH, J=10.4 Hz, 8 Hz), 7.18-7.24 (m, 3H, Ph), 7.27-7.31 (m, 2H, Ph); $^{13}$C NMR (100 MHz, CDCl$_3$) δ −1.82 (SiMe$_3$), 18.7 (CH$_2$SiMe$_3$), 32.1 (PhCH$_2$), 31.5 (CHOHCH$_2$), 38.4 (PhCH$_2$CH$_2$), 70.8 (CHOH), 122.4 (CHCH), 125.7 (Ph), 128.3 (Ph), 129.3 (CHCH), 142.1 (Ph); IR (v, cm$^{-1}$) 3383 (OH), 3063 (ArH), 1667 (C=C), 1604 (Ar), 1496 (Ar), 850 (Si—C). MS (GCT, CI$^+$) m/z 280.2101 [M+NH$_4$]$^+$ HRMS required for C$_{16}$H$_{26}$OSiNH$_4$: 280.2097, found 280.2101.

Example 16

5-fluoro-1-phenylhept-6-en-3-ol

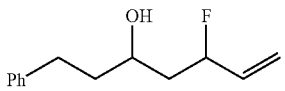

A solution of 1-phenyl-7-trimethylsilanyl-hept-5-en-3-ol (776 mg, 2.96 mmol, 1 eq) in acetonitrile (30 mL), with sodium bicarbonate (497 mg, 5.92 mmol, 2 eq), was treated with Selectflour™ (2.097 g, 5.92 mmol, 2 eq) and stirred at room temperature under an atmosphere of argon for 18 h. The reaction was then concentrated under reduced pressure and water (10 mL) was added and then extracted with ether (3×15 mL). The combined organic phases were dried over MgSO$_4$, filtered and the solvent removed under reduced pressure. Column chromatography (hexane:ether, 95:5, 9:1, 85:15) gave 5-fluoro-1-phenylhept-6-en-3-ol as a colourless oil (397 mg, 64% yield). For major diastereomer: $^1$H NMR (400 MHz, CDCl$_3$) δ 1.63-2.04 (m, 4H, CH$_2$CHF, CH$_2$CHOH), 2.67-2.74 (m, 1H, PhCH$_2$), 2.78-2.86 (m, 1H, PhCH$_2$), 3.92-3.98 major (m, 1H, CHOH), 5.05-5.20 (m, 1H, CHF), 5.22-5.27 (m, 2H, CHCH$_2$), 5.86-5.99 (m, 1H, CHCH$_2$), 7.19-7.33 (m, 5H, Ph); $^{13}$C NMR (100 MHz, CDCl$_3$) δ 31.8 (PhCH$_2$), 39.1 (PhCH$_2$CH$_2$), 42.4 (CHOHCH$_2$), 67.2 (CHOH), 90.0-91.7 (d, CHF, J=165 Hz), 116.7 (CHCH$_2$), 125.9 (Ph), 128.4 (Ph), 136.0 (CHCH$_2$), 141.7 (Ph); $^{19}$F NMR (376.5 MHz, CDCl$_3$) δ −177. For minor diastereomer: $^1$H NMR (400 MHz, CDCl$_3$) δ 1.63-2.04 (m, 4H, CH$_2$CHF, CH$_2$CHOH), 2.67-2.74 (m, 1H, PhCH$_2$), 2.78-2.86 (m, 1H, PhCH$_2$), 3.85-3.91 (m, 1H, CHOH), 5.05-5.20 (m, 1H, CHF), 5.22-5.27 (m, 2H, CHCH$_2$), 5.33-5.39 (m, 1H, CHCH$_2$), 7.19-7.33 (m, 5H, Ph); $^{13}$C NMR (100 MHz, CDCl$_3$) δ 31.8 (PhCH$_2$), 39.1 (PhCH$_2$CH$_2$), 42.4 (CHOHCH$_2$), 68.9 (CHOH), 92.3-93.9 (d, CHF, J=164 Hz), 116.7(CHCH$_2$), 125.9 (Ph), 128.4 (Ph), 136.0 (CHCH$_2$), 141.7 (Ph); $^{19}$F NMR (376.5 MHz, CDCl$_3$) δ −180. IR (v, cm$^{-1}$) 3418 (OH), 1651 (C=C), 1496 (Ar), 1455 (Ar); MS (GCT, CI$^+$) m/z 226.2 [M+NH$_4$]$^+$ HRMS required for C$_{13}$H$_{21}$FON: 226.1607, found 226.1611.

Example 17

1-phenyl-7-(triisopropylsilyl)hept-5-en-3-ol

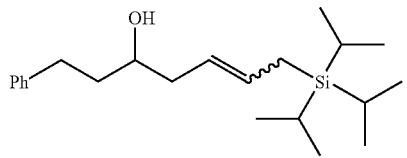

To a round-bottomed flask containing 1-phenyl-hex-5-en-3-ol (43 mg, 0.24 mmol, 1 eq)) in DCM (2 mL) was added allyltriisopropylsilane (0.173 mL, 0.72 mmol, 3 eq). Hoveyda-Grubbs' Catalyst (4 mg, 0.006 mmol, 0.025 eq) was subsequently added as a solid and the reaction was left to stir under an atmosphere of argon. After 6 days the reaction was concentrated under reduced pressure to a dark brown oil. Column chromatography (hexane:ether, 100:0, 90:10, 85:15) gave 1-phenyl-7-(triisopropylsilyl)hept-5-en-3-ol as a colourless oil (51 mg, 61% yield). For major isomer E: $^1$H NMR (400 MHz, CDCl$_3$) δ 1.05 (s, 21H, Si(i-Pr)$_3$), 1.60-1.62 (d, 2H, CH$_2$ Si(i-Pr)$_3$, J=8 Hz), 1.72-1.85 (m, 2H, CH$_2$CH$_2$CHOH), 2.06-2.14 (m, 1H, CHOHCH$_2$CH), 2.22-2.34 (m, 1H, CHOHCH$_2$CH), 2.64-2.74 (m, 1H, PhCH$_2$), 2.78-2.87 (m, 1H, PhCH$_2$), 3.58-3.64 (m, 1H, CHOH), 5.24-5.34 (m, 1H, CH$_2$CHCH), 5.58-5.66 (dt, 1H, CH$_2$CHCH, J=16, 8 Hz), 7.17-7.23 (m, 4H, Ph), 7.27-7.31 (m, 1H, Ph); $^{13}$C NMR (100 MHz, CDCl$_3$) δ 11.0 (Si(i-Pr)$_3$), 15.6 (CH$_2$ Si(i-Pr)$_3$), 18.7 (Si(i-Pr)$_3$), 32.1 (PhCH$_2$), 38.4 (PhCH$_2$CH$_2$), 41.1 (CHOHCH$_2$), 70.4 (CHOH), 123.9 (CH$_2$CHCH), 125.7 (Ph), 128.3 (Ph), 128.4 (Ph), 131.9 (CH$_2$CHCH), 142.2 (Ph). For minor isomer Z: $^1$H NMR (400 MHz, CDCl$_3$) δ 1.05 (s, 21H, Si(i-Pr)$_3$), 1.60-1.62 (d, 2H, CH2 Si(i-Pr)$_3$, J=8 Hz), 1.72-1.85 (m, 2H, CH$_2$CH$_2$CHOH), 2.06-2.14 (m, 1H, CHOHCH$_2$CH), 2.22-2.34 (m, 1H, CHOHCH$_2$CH), 2.64-2.74 (m, 1H, PhCH$_2$), 2.78-2.87 (m, 1H, PhCH$_2$), 3.65-3.71 (m, 1H, CHOH), 5.24-5.34 (m, 1H, CH$_2$CHCH), 5.68-5.75 (dt, 1H, CH$_2$CHCH, J=12, 8 Hz), 7.17-7.23 (m, 4H, Ph), 7.27-7.31 (m, 1H, Ph); $^{13}$C NMR (100 MHz, CDCl$_3$) δ 11.0 (Si(i-Pr)$_3$), 15.6 (CH$_2$ Si(i-Pr)$_3$), 18.7 (Si(i-Pr)$_3$), 32.1 (PhCH$_2$), 35.3 (CHOHCH$_2$), 38.4 (PhCH$_2$CH$_2$), 70.9 (CHOH), 122.3 (CH$_2$CHCH), 125.7 (Ph), 128.3 (Ph), 128.4 (Ph), 130.3 (CH$_2$CHCH), 142.2 (Ph); IR (v, cm$^{-1}$) 3362 (OH), 3026 (Ar—H), 1604 (C=C), 1496 (Ar), 1462 (Ar), 699 (Si—C); HRMS required for C$_{22}$H$_{38}$OSi: 346.2692, found 346.2683.

Example 18

{[3-fluoro-5-(2-phenylethyl)tetrahydrofuran-2-yl]methyl}(triisopropyl)silane

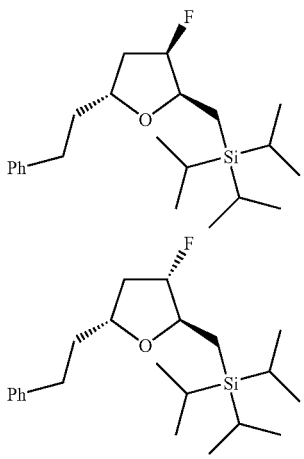

A solution of 1-phenyl-7-(triisopropylsilyl)hept-5-en-3-ol (149 mg, 0.43 mmol, 1 eq) in acetonitrile (5 mL) was treated with Selectfluor (152 mg, 0.43 mmol, 1 eq) and stirred at room temperature under an atmosphere of argon for 18 h. The acetonitrile was removed under reduced pressure and the reaction was quenched with saturated aqueous sodium hydrogen carbonate (5 mL). It was then extracted with ether (3×10 mL), dried over MgSO$_4$, filtered and the solvent removed under reduced pressure to give a pale yellow oil. Column chromatography (hexane:ether, 9:1) gave {[3-fluoro-5-(2-phenylethyl)tetrahydrofuran-2-yl]methyl}(triisopropyl)silane as a colourless oil (157 mg, 66% yield). For the major diastereomer depicted on the left hand side in the pair of formulae above: $^1$H NMR (400 MHz, CDCl$_3$) δ 0.92-1.00 (dd, 1H, CH$_2$Si, J=14.4, 5.6 Hz), 1.08-1.10 (m, 21H, SiCHCH$_3$), 1.19-1.26 (m, 1H, CH$_2$Si) 1.66-1.89 (m, 2H, PhCH$_2$CH$_2$), 1.93-2.02 (m, 1H, CH$_2$CHF), 2.26-2.43 (m, 1H, CH$_2$CHF), 2.60-2.83 (m, 2H, PhCH$_2$), 3.70-3.81 (m, 1H, PhCH$_2$CH$_2$CHO), 4.06-4.17 (dddd, 1H, OCHCHF, J=27.6, 8.4, 5.6, 2.8 Hz), 4.83-4.98 (m, 1H, CHF); $^{13}$C NMR (100 MHz, CDCl$_3$) δ 8.21-8.26 (CH$_2$Si), 11.4 (Si(CH(CH$_3$)$_2$)$_3$), 18.9 (Si(CH(CH$_3$)$_2$)$_3$), 32.5 (PhCH$_2$), 38.0 (PhCH$_2$CH$_2$), 39.2-39.4 (d, CH$_2$CHF, J=21 Hz), 76.1 (PhCH$_2$CH$_2$CHO), 78.6-78.8 (d, CHFCHO, J=20 Hz), 94.6-96.5 (d, CHF, J=182), 125.7 (Ph), 125.8 (Ph), 128.3 (Ph), 128.4 (Ph), 142.1 (Ph); $^{19}$F NMR (376.5 MHz, CDCl$_3$) δ −191.5 For the major diastereomer depicted on the right hand side in the pair of formulae above: $^1$H NMR (400 MHz, CDCl$_3$) δ 0.92-1.00 (dd, 1H, CH$_2$Si, J=14.4, 5.6 Hz), 1.08-1.10 (m, 21H, SiCHCH$_3$ ), 1.19-1.26 (m, 1H, CH$_2$Si) 1.66-1.89 (m, 2H, PhCH$_2$CH$_2$), 1.93-2.02 (m, 1H, CH$_2$CHF), 2.26-2.43 (m, 1H, CH$_2$CHF), 2.60-2.83 (m, 2H, PhCH$_2$), 3.70-3.81 (m, 1H, PhCH$_2$CH$_2$CHO), 4.20-4.27 (m, 1H, OCHCHF), 4.78-4.93 (m, 1H, CHF); $^{13}$C NMR (100 MHz, CDCl$_3$) δ 8.75-8.82 (CH$_2$Si), 11.4 (Si(CH(CH$_3$)$_2$)$_3$), 18.9 (Si(CH(CH$_3$)$_2$)$_3$), 32.7 (PhCH$_2$), 38.2 (PhCH$_2$CH$_2$), 39.6-39.9 (d, CH$_2$CHF, J=21 Hz), 77.2 (PhCH$_2$CH$_2$CHO), 80.1-80.3 (d, CHFCHO, J=21 Hz), 94.0-94.5 (d, CHF, J=183), 125.8 (Ph), 128.3 (Ph), 128.4 (Ph), 128.5 (Ph), 142.1 (Ph); $^{19}$F NMR (376.5 MHz, CDCl$_3$) δ −185.5; IR (v, cm$^{-1}$) 3027 (Ar—H), 1496 (Ar), 1464 (Ar), 1384 (Ar), 1096 (C—O—C), 699 (Si—C); MS (GCT, CI$^+$) m/z 226.2 [M+NH$_4$]$^+$ HRMS required for C$_{22}$H$_{41}$FNOSi: 382.2941, found 382.2935.

Example 19

5-(Triisopropylsilyl)-pent-3-enoic acid

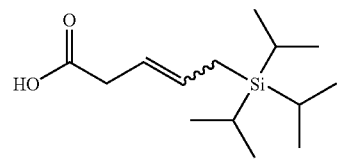

A flame dried round-bottomed flask was charged with allyltriisopropylsilane (0.722 mL, 3 mmol, 3 eq), 3-butenoic acid (0.084 mL, 1 mmol, 1 eq) and DCM (3 mL). Hoveyda-Grubbs' Catalyst (31 mg, 0.05 mmol, 0.05 eq) was subsequently added as a solid and the reaction was heated to reflux (40° C.) under an atmosphere of argon. After 3 days the reaction was concentrated under reduced pressure to give a dark brown oil. Column chromatography (hexane:ether, 85:15, to remove excess silane, then 50:50) gave 5-(triisopropylsilyl)-pent-3-enoic acid as a colourless oil (223 mg, 87% yield). For major isomer E: $^1$H NMR (400 MHz, CDCl$_3$) δ 1.05-1.06 (m, 21H, Si(i-Pr)$_3$), 1.61-1.63 (d, 2H, CH$_2$Si(i-Pr)$_3$, J=8.0 Hz), 3.04-3.06 (d, 2H, HOOCCH$_2$, J=7 Hz), 5.37-5.45 (m, 1H, CH$_2$CHCH), 5.62-5.70 (dt, CH$_2$CHCH, J=15.1, 8.2 Hz), 11.41 (s, 1H, COOH); $^{13}$C NMR (50 MHz, CDCl$_3$) δ 10.9 (Si(CH(CH$_3$)$_2$)$_3$), 15.6 (CH$_2$Si(i-Pr)$_3$), 18.6 (Si(CH(CH$_3$)$_2$)$_3$), 38.0 (HOOCCH$_2$), 118.8 (CH$_2$CHCH), 132.6 (CH$_2$CHCH), 178.7 (HOOC). For minor isomer Z: $^1$H NMR (400 MHz, CDCl$_3$) δ 1.05-1.06 (m, 21H, Si(i-Pr)$_3$), 1.56-1.58 (d, 2H, CH$_2$Si(i-Pr)$_3$, J=8.6 Hz), 3.17-3.19 (d, 2H, HOOCCH$_2$, J=7.8 Hz), 5.37-5.45 (m, 1H, CH$_2$CHCH), 5.71-5.78 (m, CH$_2$CHCH), 11.41 (s, 1H, COOH); $^{13}$C NMR (50 MHz, CDCl$_3$) δ 11.0 (CH$_2$Si(i-Pr)$_3$), 11.1 (Si(CH(CH$_3$)$_2$)$_3$), 18.6 (Si(CH(CH$_3$)$_2$)$_3$), 32.5 (HOOCCH$_2$), 117.5 (CH$_2$CHCH), 130.7 (CH$_2$CHCH), 178.6 (HOOC); IR (v, cm$^{-1}$) 2867 (COO—H), 1713 (HOC=O), 660 (C—Si); HRMS required for C$_{14}$H$_{28}$O$_2$Si: 256.1859, found 256.1866.

Example 20

6-(Triisopropylsilyl)-hex-4-enoic-acid

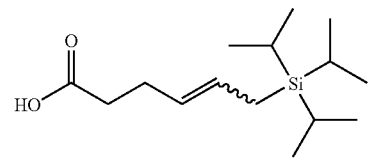

A flame dried round-bottomed flask was charged with allyltriisopropylsilane (0.722 mL, 3 mmol, 3 eq), 4-pentenoic acid (0.102 mL, 1 mmol, 1 eq) and dichloromethane (3 nmL). Hoveyda-Grubbs' catalyst (5 mol %, 31 mg) was subsequently added as a solid and the reaction was heated to reflux (40° C.) and left to stir under an atmosphere of argon. After 3 days the reaction was concentrated under reduced pressure to give a dark brown oil. Column chromatography (100% hexane to remove remaining silane, then hexane:ether, 75:25) gave 6-(triisopropylsilyl)-hex-4-enoic acid as a colourless oil (258 mg, 95% yield). For major isomer E: $^1$H NMR (400 MHz, CDCl$_3$) δ 1.04-1.06 (m, 21H, Si(i–Pr)$_3$), 1.54-1.56 (d, 2H, C$\underline{H}_2$Si(i–Pr)$_3$, J=8.0 Hz), 2.29-2.35 (m, 2H, HOOCCH$_2$C$\underline{H}_2$), 2.37-2.42 (m, 2H, HOOCC$\underline{H}_2$), 5.28-5.35 (m, 1H, CH$_2$CHCH), 5.52-5.60 (m, 1H, CH$_2$CHCH); $^{13}$C NMR (100 MHz, CDCl$_3$) δ 11.0 (Si(C$\underline{H}$(CH$_3$)$_2$)$_3$), 15.3 (C$\underline{H}_2$Si(i–Pr)$_3$), 18.7 (Si(CH(C$\underline{H}_3$)$_2$)$_3$), 27.8 (HOOCCH$_2$C$\underline{H}$2), 34.3 (HOOCC$\underline{H}_2$CH2), 125.9 (CH$_2$C$\underline{H}$CH), 129.0 (CH$_2$CH$\underline{C}$H), 179.5 (HOO$\underline{C}$). For minor isomer Z: $^1$H NMR (400 MHz, CDCl$_3$) δ 1.04-1.06 (m, 21H, Si(i–Pr)$_3$), 1.62-1.64 (d, 2H, C$\underline{H}_2$Si(i–Pr)$_3$, J=8.0 Hz), 2.29-2.35 (m, 2H, HOOCCH$_2$C$\underline{H}_2$), 2.37-2.42 (m, 2H, HOOCC$\underline{H}_2$), 5.38-5.50 (m, 1H, CH$_2$CHCH), 5.63-5.75 (m, 1H, CH$_2$CHCH); $^{13}$C NMR (100 MHz, CDCl$_3$) δ 10.9 (C$\underline{H}_2$Si(i–Pr)$_3$), 11.1 (Si(C$\underline{H}$(CH$_3$)$_2$)$_3$), 18.7 (Si(CH(C$\underline{H}_3$)$_2$)$_3$), 24.7 (HOOCCH$_2$C$\underline{H}_2$), 30.9 (HOOCC$\underline{H}_2$CH$_2$), 124.6 (CH$_2$C$\underline{H}$CH), 128.2 (CH$_2$CH$\underline{C}$H), 176.9 (HOO$\underline{C}$); IR (v, cm$^{-1}$) 2867 (COO—H), 1713 (HOC=O), 660 (C—Si); HRMS required for C$_{15}$H$_{30}$O$_2$Si [M–H]$^-$: 269.1937, found 269.1937.

Example 21

(4R, 5S)-4-fluoro-5-[(triisopropylsilyl)methyl]dihydrofuran-2(3H)-one

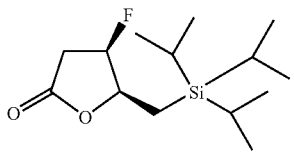

A solution of 5-triisopropylsilanyl-pent-3-enoic-acid (135 mg, 0.52 mmol, 1 e) in dichloromethane (5 mL) with sodium bicarbonate (87 mg, 1 mmol, 2 eq), was treated with Selectfluor (187 mg, 0.52 mmol, 1 eq) and stirred at room temperature under an atmosphere of argon. After 7 days the dichloromethane was removed under reduced pressure and the product filtered through silica with ether. The solvent was then removed under reduced pressure. Column chromatography (hexane:ether, 90:10, 85:15) gave (4R,5S)-4-fluoro-5-[triisopropylsilyl)methyl]dihydrofuran-2(3H)-one as a white solid (92 mg, 64% yield). $^1$H NMR (400 MHz, CDCl$_3$) δ 1.06-1.09 (m, 22H, C$\underline{H}_2$Si, Si(i–Pr)$_3$), 1.32-1.39 (m, 1H, CH$_2$Si), 2.78-2.87 (m, 2H, C$\underline{H}_2$CHF), 4.62-4.73 (dddd, 1H, CHFC$\underline{H}$O, J=24.8, 9.0, 6.2, 3.1 Hz), 5.03-5.18 (m, 1H, C$\underline{H}$F); $^{13}$C NMR (100 MHz, CDCl$_3$) δ 8.4 (C$\underline{H}_2$Si(i–Pr)$_3$), 11.2 (Si(C$\underline{H}$(CH$_3$)$_2$)$_3$), 18.7 (Si(CH(C$\underline{H}_3$)$_2$)$_3$), 37.4-37.7 (d, C$\underline{H}_2$CHF, J=26 Hz), 82.2-82.4 (d, CHFC$\underline{H}$, J=22 Hz), 89.5-91.3 (d, C$\underline{H}$F, J=185 Hz), 173.7 (C=O); $^{19}$F NMR (376.5 MHz, CDCl$_3$) δ –192.5; IR (v, cm$^{-1}$) 1775 (C=O), 711 (Si—C); HRMS required for C$_{14}$H$_{27}$FO$_2$SiNH$_4$: 292.2108, found 292.2096. MP 52-55° C.

Example 22

(4R, 5R)-4-fluoro-5-[(triisopropylsilyl)methyl]dihydrofuran-2(3H)-one

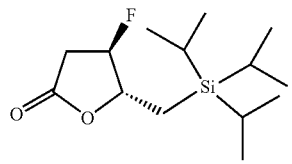

A solution of 5-triisopropylsilanyl-pent-3-enoic-acid (135 mg, 0.52 mmol, 1 eq) in dichloromethane (5 mL) with sodium bicarbonate (87 mg, 1 mmol, 2 eq), was treated with Selectfluor (187 mg, 0.52 mmol, 1 eq) and stirred at room temperature under an atmosphere of argon. After 7 days the dichloromethane was removed under reduced pressure and the product filtered through silica with ether. The solvent was then removed under reduced pressure. Column chromatography (hexane:ether, 90:10, 85:15) gave (4R,5R)-4-fluoro-5-[triisopropylsilyl)methyl]dihydrofuran-2(3H)-one as a white solid (18 mg, 13% yield). $^1$H NMR (400 MHz, CDCl$_3$) δ 0.95-0.97 (d, 2H, C$\underline{H}_2$Si, J=8 Hz), 1.06-1.09 (m, 21H, Si(i–Pr)$_3$), 2.68-2.79 (dd, 1H, C$\underline{H}_2$CHF, J=24, 20 Hz), 2.86-3.01 (ddd, 1H, C$\underline{H}_2$CHF, J=35.2, 18.7, 5.4 Hz), 4.83-4.92 (dt, 1H, CHFC$\underline{H}$O, J=21.7, 7.9 Hz), 4.94-5.08 (dd, 1H, C$\underline{H}$F, J=53.5, 5.4 Hz); $^{13}$C NMR (100 MHz, CDCl$_3$) δ 8.5 (C$\underline{H}_2$Si(i–Pr)$_3$), 11.1 (Si(C$\underline{H}$(CH$_3$)$_2$)$_3$), 18.7 (s, Si(CH(C$\underline{H}_3$)$_2$)$_3$), 34.6-34.8 (d, C$\underline{H}_2$CHF, J=24 Hz), 84.2-84.0 (d, CHFC$\underline{H}$, J=24 Hz), 89.5-91.3 (d, C$\underline{H}$F, J=185 Hz), 173.8 (C=O).; $^{19}$F NMR (376.5 MHz, CDCl$_3$) δ –170.7; IR (v, cm$^{-1}$) 1774 (C=O), 747 (Si—C); MS (GCT, CI$^+$) m/z 275.18 [M+H]$^+$. MP 47-50° C.

Example 23

(5R, 6S)-5-fluoro-6-[(triisopropylsilyl)methyl]tetrahydro-2H-pyran-2-one

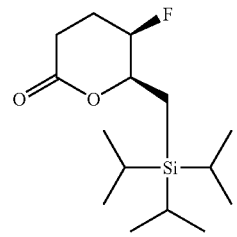

A solution of 6-(triisopropylsilyl)-hex-4-enoic-acid in acetone with sodium bicarbonate was treated with Selectfluor™ and stirred at room temperature under an atmosphere of argon. After 7 days the acetone was removed under reduced pressure and the crude mixture was washed with ether and filtered through silica. The ether was then removed under reduced pressure to give a pale yellow oil. Column chromatography (hexane:ether 9:1) gave the major diastereomer (5R, 6S)-5-fluoro-6-[(triisopropylsilyl)methyl]tetrahydro-2H-pyran-2-one as a white solid (90 mg, 45% yield). $^1$H NMR (400 MHz, CDCl$_3$) δ 1.06-1.17 (m, 22H, C$\underline{H}_2$Si, Si(i–Pr)$_3$), 1.36-1.42 (dd, 1H, CH$_2$Si, J=12, 8 Hz), 2.01-2.20 (m, 1H, C H₂CHF, J=38.3, 14.8, 10.5, 7.4, 3.2 Hz), 2.22-2.33 (m, 1H, CH₂CHF, J=21.6, 10.9, 7.3, 3.9 Hz), 2.47-2.55 (ddd, 1H, CH₂CH₂CHF, J=17.8, 7.6, 4.1 Hz), 2.61-2.70 (ddd, 1H, CH₂CH₂CHF, J=17.8, 10.4, 7.3 Hz), 4.44-4.55 (m, 1H, CHFCHO, J=28.0, 9.1, 6.2, 1.4 Hz), 4.66-4.80 (m, 1H, CHF, J=47.8, 3.4, 3.4, 1.4 Hz); ¹³C NMR (100 MHz, CDCl₃) δ 11.34 (Si(CH(CH₃)₂)₃), 12.3 (CH₂Si(i–Pr)₃), 18.7-18.8 (Si(CH(CH₃)₂)₃), 24.49-24.53 (d, CH₂CH₂CHF, J=4 Hz), 25.2-25.4 (d, CH₂CHF, J=22 Hz), 79.3-79.5 (d, CHFCH, J=20 Hz), 85.68-87.47 (d, CHF, J=179 Hz), 169.7 (C=O); ¹⁹F NMR (376.5 MHz, CDCl₃) δ −201.7; IR (v, cm⁻¹) 1736 (C=O), 803 (Si—C); HRMS required for C₁₅H₂₉FO₂SiNH₄: 306.2265, found 306.2272. MP 62-65° C.

Example 24

(5R, 6R)-5-fluoro-6-[(triisopropylsilyl)methyl]tetrahydro-2H-pyran-2-one

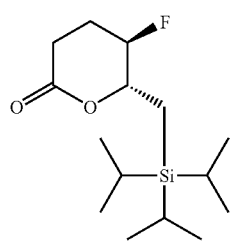

A solution of 6-(triisopropylsilyl)-hex-4-enoic-acid in acetone with sodium bicarbonate was treated with Selectfluor™ and stirred at room temperature under an atmosphere of argon. After 7 days the acetone was removed under reduced pressure and the crude mixture was washed with ether and filtered through silica. The ether was then removed under reduced pressure to give a pale yellow oil. Column chromatography (hexane:ether 9:1) gave the diastereomer (5R,6R)-5-fluoro-6-[(triisopropylsilyl)methyl]tetrahydro-2H-pyran-2-one as a white solid (9 mg, 6% yield). ¹H NMR (400 MHz, C₆D₆) δ 0.74-0.81 (m, 2H, CH₂Si), 1.02-1.06 (m, 21H, Si(i–Pr)₃), 1.3-1.4 (m, 2H, CH₂CHF), 1.91-1.98 (ddd, 1H, CH₂CH₂CHF, J=17.6, 5.5, 5.4 Hz), 2.14-2.23 (m, 1H, CH₂CH₂CHF), 3.83-3.99 (ddd, 1H, CHF, J=49.2, 9.8, 4.9 Hz), 4.34-4.42 (ddd, 1H, CHFCHO, J=17.96, 10.0, 4.8 Hz); ¹³C NMR (125 MHz, C₆D₆) δ 11.76 (Si(CH(CH₃)₂)₃), 15.00-15.03 (d, CH₂Si(i–Pr)₃, J=3.8 Hz), 19.3 (Si(CH(CH₃)₂)₃), 23.6-23.8 (d, CH₂CHF, J=22.5 Hz), 26.10-26.14 (d, CH₂CH₂CHF, J=5 Hz), 78.9-79.1 (d, CHFCH, J=25 Hz), 89.5-90.9 (d, CHF, J=175 Hz), 168.4 (C=O); ¹⁹F NMR (376.5 MHz, CDCl₃) δ −180.8; IR (v, cm⁻¹) 1743 (C=O), 839 (Si—C); HRMS required for C₁₅H₂₉FO₂SiNH₄: 306.2265, found 306.2256. MP 40-45° C.

Example 25

Cyclohexa-2,5-dien-1-yl(trimethyl)silane

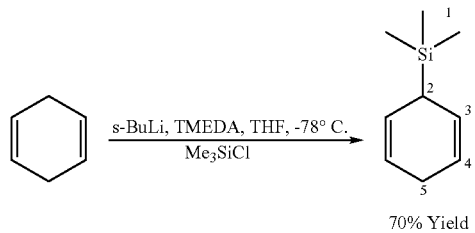

70% Yield 1,4-Cyclohexadiene (0.47 mL, 5 mmol, 1 eq.) was dissolved in TBF (8 mL), cooled to −78° C. and s-BuLi (4.5 mL, 1.2 M, 5.5 mmol, 1.1 eq.) was added slowly. The resulting solution was treated with TMEDA (0.77 mL, 5 mmol, 1 eq.) and the reaction was allowed to warm to −45° C. over 2 hours. Me₃SiCl (0.7 mL, 5.5 mmol, 1.1 eq.) was added, the reaction mixture was stirred for 1 hour at room temperature and then quenched with H₂O and Et₂O. The organic layer was separated and washed with H₂O (2×30 mL), (aq) sat. NH₄Cl (30 mL), brine (30 mL) and dried over MgSO₄. Removal of the solvent in vacuo and distillation using Kugelrohr apparatus (30 mbar, 70° C.) afforded the product as colourless oil (0.53 g, 3.47 mmol, 70% yield): ¹H NMR (400 MHz, CDCl₃), δ 5.56 (2H, m, H-3), 5.55 (2H, m, H-4), 2.69 (2H, m, H-5), 2.22 (1H, m, H-2), 0.03 (9H, s, H-1); ¹³C NMR (100 MHz, CDCl₃) δ 126.31 (C-3), 121.33 (C-4), 31.52 (C-5), 26.40 (C-2), −3.55 (C-1); IR (CDCl₃, cm⁻¹) 3027 (m, C—H), 2959 (m, C—H), 1622 (w, C=C), 743, (m, C—H); MS (FI+, m/z), 152.10 [M].

Example 26 tert-butyl(cyclohexa-2,5-dien-1-yl)dimethylsilane

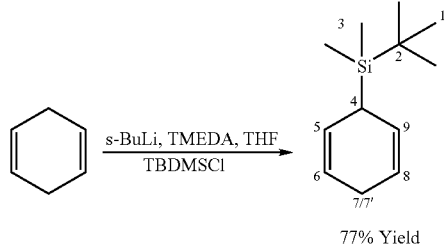

77% Yield 1,4,-Cyclohexadiene (3.76 mL, 40 mmol, 1 eq.) was dissolved in THF (64 mL) and cooled to −78° C. s-BuLi (40 mL, 44 mmol, 1.1 eq.) was added dropwise and the resulting suspension was treated with TMEDA (6.12 mL, 40 mmol, 1 eq.). The reaction mixture was allowed to warm to −45° C. over 2 hours, TBDMSCl (6.6 g, 44 mmol, 1.1 eq.) in THF (20 mL) was added dropwise and the reaction stirred at room temperature for 1 hour. The reaction was quenched with Et₂O and H₂O and then extracted with Et₂O (3×100 mL). The combined organic layers were washed with sat. NH₄Cl (aq.) (100 mL) and brine (100 mL), dried over MgSO₄ and the solvent removed in vacuo. Distillation using Kugelrohr apparatus (125° C., 43 mbar) afforded the product as a colourless oil (5.9 g, 31 mmol, 77% yield). $^1$H NMR (CDCl$_3$) δ 5.74 (2H, m, H-5), 5.55 (2H, m, H-6), 2.70 (2H, m, H-7), 2.41 (1H, m, H-4), 0.95 (9H, s, H-1), 0.01 (6H, s, H-3); C$^{13}$ NMR (100 MHz, CDCl$_3$) δ 134.5 (C-4), 121.2 (C-5), 29.3 (C-4), 27.2 (C-7), 26.2 (C-1), 17.7 (C-2), −6.2 (C-3); IR (neat, cm$^{-1}$) 3029 (m, C—H), 2956 (m, C—H), 1667 (w, C═C); MS (CI, m/z) 195.16 [M+H$^+$].

Example 27

(1S, 2S, 3S)-3-(Trimethylsilyl)cyclohexane-4-ene-1,2,diol

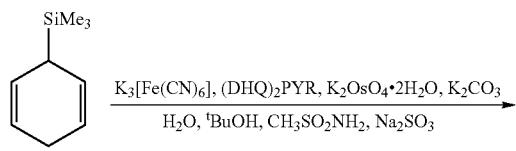

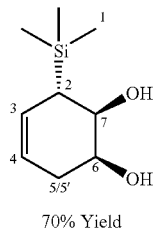

70% Yield

K$_3$[Fe(CN)$_6$] (0.98 g, 3 mmol, 3 eq), K$_2$CO$_3$ (0.412 g, 3 mmol, 3 eq), (DHQ)$_2$PYR (0.0078 g, 0.01 mmol, 0.01 eq), K$_2$OsO$_4$.2H$_2$O (0.0037 g, 0.01 mmol, 0.01 eq), H$_2$O, (5 mL) and $^t$BuOH, (5 mL) were added to a round bottomed flask and stirred until the solution went clear. Methansulfonamide (0.095 g, 1 mmol, 1 eq) was added, the mixture cooled to 0° C. and the diene of Example 25 (0.152 g, 1 mmol, 1 eq) was introduced with vigorous stirring. The mixture was then stirred at room temperature for 48 hours, before sodium sulfite (1 g) was added and stirred for 45 minutes. The reaction mixture was extracted with EtOAc (3×20 mL) and the combined extracts washed with 10% NaOH (20 mL) and brine (20 mL), then dried over MgSO$_4$ and the solvent removed in vacuo. Column chromatography (cyclohexane: EtOAc, 60:40, R$_f$=0.2) furnished the product as a colourless oil (0.13 g, 0.7 mmol, 70% yield): [α]$_D^{298}$=+106.15° (c=0.13, CHCl$_3$); $^1$H NMR (400 MHz, CDCl$_3$) 5.56 (1H, m, H-3), 5.50 (1H, m, H-4), 3.94 (1H, m, H-7), 3.81 (1H, m, H-6), 2.35 (1H, m, H-5), 1.86 (1H, m, H-5'), 1.86 (1H, m, H-2), 0.07 (9H, s, H-1); $^{13}$C NMR (100 MHz, CDCl$_3$) δ 125.19 (C-4), 120.82 (C-3), 70.39 (C-6), 68.30 (C-7), 35.73 (C-2), 30.16 (C-5), −2.42 (C-1); IR (neat, cm$^{-1}$) 3425 (b, OH) 1641 (b, C═C); MS (ESI-, m/z) 185.25 [M−H$^+$].

Example 28

(Trimethylsilyl)cyclohexane-4-ene-1,2,diol

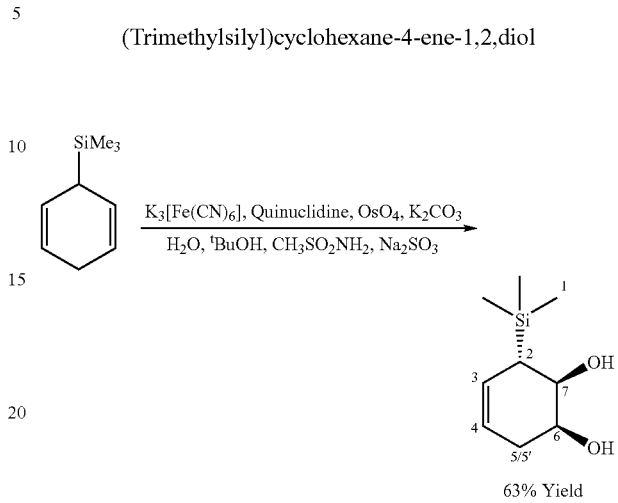

63% Yield

K$_3$[Fe(CN)$_6$] (0.98 g, 3 mmol, 3 eq), K$_2$CO$_3$ (0.412 g, 3 mmol, 3 eq), quinuclidine (0.004 g, 0.01 mmol, 0.01 eq), OSO$_4$ (0.003 mL, 0.01 mmol, 0.01 eq), H$_2$O, (5 mL) and $^t$BuOH, (5 mL) were added to a round bottomed flask and stirred until the solution went clear. Methansulfonamide (0.095 g, 1 mmol, 1 eq) was added, the mixture cooled to 0° C. and the diene of Example 25 (0.152 g, 1 mmol, 1 eq) was introduced with vigorous stirring. The mixture was then stirred at room temperature for 48 hours, before sodium sulfite (1 g) was added and stirred for 45 minutes. The reaction mixture was extracted with EtOAc (3×20 mL) and the combined extracts washed with 10% NaOH (20 mL) and brine (20 mL), then dried over MgSO$_4$ and the solvent removed in vacuo. Column chromatography (cyclohexane: EtOAc, 60:40, R$_f$=0.25) furnished the product as a colourless oil (0.118 g, 0.63 mmol, 63% yield); $^1$H NMR (400 MHz, CDCl$_3$) 5.56 (1H, m, H-3), 5.50 (1H, m, H-4), 3.94 (1H, m, H-7), 3.81 (1H, m, H-6), 2.35 (1H, m, H-5), 1.86 (1H, m, H-5'), 1.86 (1H, m, H-2), 0.07 (9H, s, H-1); $^{13}$C NMR (100 MHz, CDCl$_3$) δ 125.19 (C-4), 120.82 (C-3), 70.39 (C-6), 68.30 (C-7), 35.73 (C-2), 30.16 (C-5), −2.42 (C-1); IR (neat, cm$^{-1}$) 3423 (b, OH) 1640 (b, C═C) MS (ESI-, m/z) 185.25 [M−H$^+$].

Example 29

(Trimethylsilyl)cyclohexane-4-ene-1,2,diol

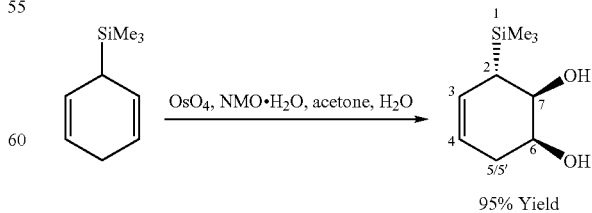

95% Yield

The allylsilane of Example 25 (0.74 g, 4.9 mmol, 1 eq.) was added to a stirring solution of NMO.H$_2$O (2 g, 14.8 mmol, 3 eq.) and OsO$_4$ (100 μL, 0.25 mmol, 0.05 eq.) in acetone (200 mL) and water (50 mL). The reaction was stirred at room temperature overnight before Na$_2$SO$_3$ (0.25 g) was added and the acetone removed in vacuo. The aqueous layer was extracted with EtOAc (3×100 mL) and the combined organic layers were washed with brine, dried over MgSO$_4$ and the solvent removed in vacuo. Column chromatography (cyclohexane:EtOAc, 60:40, R$_F$=0.25) furnished the product as a colourless oil (0.87 g, 4.7 mmol, 95% yield); $^1$H NMR (400 MHz, CDCl$_3$) 5.56 (1H, m, H-3), 5.50 (1H, m, H-4), 3.94 (1H, m, H-7), 3.81 (1H, m, H-6), 2.35 (1H, m, H-5), 1.86 (1H, m, H-5'), 1.86 (1H, m, H-2), 0.07 (9H, s, H-1); $^{13}$C NMR (100 MHz, CDCl$_3$) δ 125.19 (C-4), 120.82 (C-3), 70.39 (C-6), 68.30 (C-7), 35.73 (C-2), 30.16 (C-5), −2.42 (C-1); IR (neat, cm$^{-1}$) 3423 (b, OH) 1640 (b, C=C) MS (ESI-, m/z) 185.25 [M−H$^+$].

Example 30

(Trimethylsilyl)cyclohexane-4-ene-1,2,diol

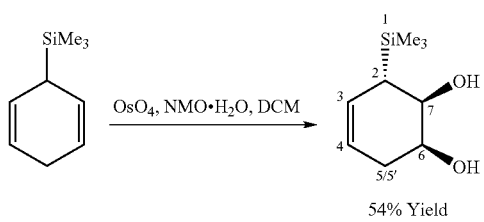

54% Yield

The allylsilane of Example 25 (0.15 g, 1 mmol, 1 eq.) was added to a stirring solution of NMO.H$_2$O (0.4 g, 3 mmol, 3 eq.) and OsO$_4$ (20 μL, 0.05 mmol, 0.05 eq.) in DCM (50 mL) and the reaction stirred overnight at room temperature. Na$_2$SO$_3$ (0.1 g) was added and the organic layer was washed with H$_2$O (50 mL) and brine (50 mL), dried over MgSO$_4$ and the solvent removed in vacuo. Column chromatography (cyclohexane:EtOAc, 60:40, R$_F$=0.25) furnished the product as a colourless oil (0.1 g, 0.54 mmol, 54% yield); $^1$H NMR (400 MHz, CDCl$_3$) 5.56 (1H, m, H-3), 5.50 (1H, m, H-4), 3.94 (1H, m, H-7), 3.81 (1H, m, H-6), 2.35 (1H, m, H-5), 1.86 (1H, m, H-5'), 1.86 (1H, m, H-2), 0.07 (9H, s, H-1); $^{13}$C NMR (100 MHz, CDCl$_3$) δ 125.19 (C-4), 120.82 (C-3), 70.39 (C-6), 68.30 (C-7), 35.73 (C-2), 30.16 (C-5), −2.42 (C-1); IR (neat, cm$^{-1}$) 3423 (b, OH) 1640 (b, C=C) MS (ESI-, m/z) 185.25 [M−H$^+$].

Example 31

1S, 2S, 3S-3-[tert-butyl(dimethyl)silyl]cyclohex-4-ene-1,2-diol

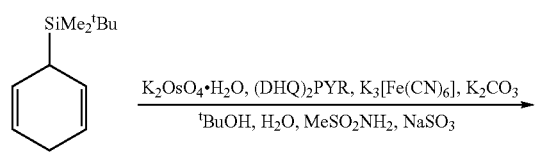

-continued

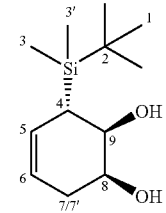

K$_3$[Fe(CN)$_6$] (2.94 g, 9 mmol, 3 eq), K$_2$CO$_3$ (1.24 g, 9 mmol, 3 eq), (DHQ)$_2$PYR (0.023 g, 0.03 mmol, 0.01 eq), K$_2$OsO$_4$.H$_2$O (0.01 mg, 0.03 mmol, 0.01 eq), H$_2$O, (15 mL) and $^t$BuOH, (15 mL) were added to a round bottomed flask and stirred until the solution went clear. Methansulfonamide (0.285 g, 3 mmol, 1 eq) was added, the mixture cooled to 0° C. and the diene of Example 26 (0.684 g, 3 mmol, 1 eq) was introduced with vigorous stirring. The mixture was then stirred at room temperature for 48 hours, before sodium sulfite (3 g) was added and stirred for 45 minutes. The reaction mixture was extracted with EtOAc (3×60 mL) and the combined extracts washed with 10% NaOH (60 mL) and brine (60 mL), then dried over MgSO$_4$ and the solvent removed in vacuo. Column chromatography (cyclohexane:EtOAc, 60:40, R$_F$=0.23) furnished the product (0.53 g, 2.3 mmol, 77% yield); MP 42-44° C.; [α]$_D^{298}$=+149.5° (c=0.19, CHCl$_3$); $^1$H NMR (400 MHz, CDCl$_3$) δ 5.58 (1H, m, H-5), 5.50 (1H, m, H-6), 4.01 (1H, m, H-9), 3.82 (1H, m, H-8), 2.40 (1H, m, H-7), 2.16 (1H, m, H-7'), 2.07 (1H, m, H-4), 0.96 (9H, s, H-1), 0.04 (3H, s, H-3), 0.02 (3H, s, H-3'); $^{13}$C NMR (100 MHz, CDCl$_3$) δ 126.1 (C-5), 120.5 (C-6), 70.9 (C-9), 68.2 (C-8), 33.1 (C-4), 29.3 (C-7), 27.0 (C-1), 17.4 (C-2), −6.2 (C-3), −6.6 (C-3'); IR (CDCl$_3$, cm$^{-1}$) 3423 (s, OH), 2930 (m, C—H), 1702 (w, C=C); MS (FI, m/z) 228.1548 [M].

Example 32

(3S, 4S, 7S)-2,2-dimethyl-3,4,7-tetrahydro-1,3-benzodioxol-4-yl(trimethyl)silane

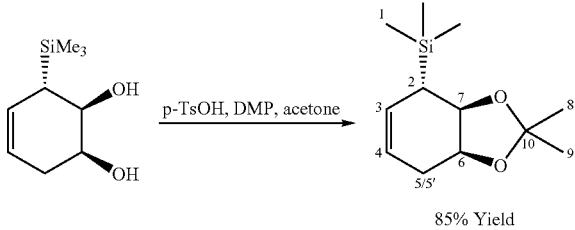

85% Yield

The diol produced in Example 27 (0.325 g, 1.75 mmol, 1 eq) was dissolved in acetone (5 mL), and DMP (4 mL). A catalytic amount of p-TsOH (0.011 g, 0.0525 mmol, 0.3 eq) was added and the reaction stirred at room temperature for 2 hours. The solvents were evaporated in vacuo and a saturated solution of NaCO$_3$ was added. The aqueous layer was extracted with Et$_2$O (3×30 mL) and the combined organic layers washed with brine, dried over MgSO$_4$ and the solvent removed in vacuo. Column chromatography (hexane:Et$_2$O, 75:25, R$_F$=0.5) furnished the product as a pale yellow oil (0.337 g, 1.49 mmol, 85% yield): [α]$_D^{298}$=+1.10° (C=0.15, CHCl$_3$); $^1$H NMR (400 MHz, CDCl$_3$) δ 5.73 (1H, dt, J$_{3-4}$=10, Hz, J$_{3-2}$=5.6 Hz, H-3), 5.62 (1H, dtd, J$_{4-3}$=10.0 Hz, J$_{4-5/5'}$=5.0

Hz, $J_{4-2}$=0.8 Hz, H-4), 4.35 (2H, m, H-7/H-6), 2.23 (2H, m, H-5/5'), 1.90 (1H, m, H-2), 1.44 (3H, s, H-8/9), 1.36 (3H, s, H-8/9), 0.06 (9H, s, H-1); $^{13}$C NMR (100 MHz, CDCl$_3$), δ 126.2 (C-3), 120.8 (C-4), 107.6 (C-10), 73.8 (C-7/6), 72.5 (C-7/6), 31.6 (C-2), 28.3 (C-5), 27.5 (C-8/9), 25.5 (C-8/9), −2.52 (C-1); IR (neat, cm$^{-1}$) 3031 (s, C—H) 1684 (s, C=C); HRMS (CI, m/z) with M: $C_{12}H_{22}O_2Si$ calc. 226.1389, found, 226.1387 [M].

Example 33

2,2-dimethyl-3,4,7-tetrahydro-1,3-benzodioxol-4-yl (trimethyl)silane

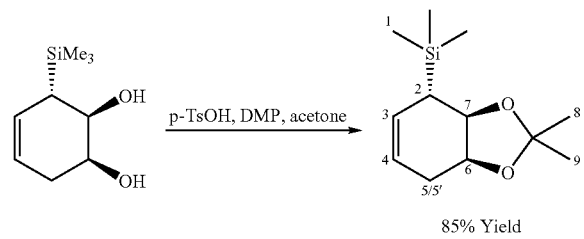

85% Yield

The diol of Example 30 (0.325 g, 1.75 mmol, 1 eq) was dissolved in acetone (5 mL), and DMP (4 mL). A catalytic amount of p-TsOH (0.011 g, 0.0525 mmol, 0.3 eq) was added and the reaction stirred at room temperature for 2 hours. The solvents were evaporated in vacuo and a saturated solution of NaCO$_3$ was added. The aqueous layer was extracted with Et$_2$O (3×30 mL) and the combined organic layers washed with brine, dried over MgSO$_4$ and the solvent removed in vacuo. Column chromatography (hexane:Et$_2$O, 75:25, R$_F$=0.5) furnished the product as a pale yellow oil (0.337 g, 1.49 mmol, 85% yield): $^1$H NMR (400 MHz, CDCl$_3$) δ 5.73 (1H, dt, $J_{3-4}$=10. Hz, $J_{3-2}$=5.6 Hz, H-3), 5.62 (1H, dtd, $J_{4-3}$=10.0 Hz. $J_{4-5/5'}$=5.0 Hz, $J_{4-2}$=0.8 Hz; H-4), 4.35 (2H, m, H-7+H-6), 2.23 (2H, m, H-5/5'), 1.90 (1H, m, H-2), 1.44 (3H, s, H-8/9), 1.36 (3H, s, H-8/9), 0.06 (9H, s, H-1); $^{13}$C NMR (100 MHz, CDCl$_3$), δ 126.2 (C-3), 120.8 (C-4), 107.6 (C-10), 73.8 (C-7/6), 72.5 (C-7/6), 31.6 (C-2), 28.3 (C-5), 27.5 (C-8/9), 25.5 (C-8/9), −2.52 (C-1); IR (neat, cm$^{-1}$) 3031 (s, C—H) 1684 (s, C=C); HRMS (CI, m/z) with M: $C_{12}H_{22}O_2Si$ calc. 226.1389, found, 226.1387 [M].

Example 34 tert-Butyl(2,2-dimethyl-3,4,7,7-tetrahydro-1,3-benzodioxol-4-yl)dimethylsilane

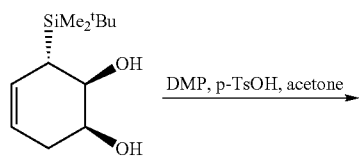

DMP, p-TsOH, acetone →

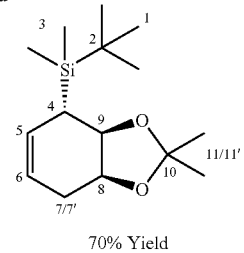

70% Yield

The diol of Example 31 (0.87 g, 4.7 mmol, 1 eq.) was dissolved in acetone (14 mL) and DMP (10 mL). A catalytic amount of p-TsOH (0.03 g, 0.14 mmol, 0.03 eq.) was added and the reaction stirred at room temperature for 2 hours. The solvents were removed in vacuo, saturated Na$_2$CO$_3$ (aq) was added and the aqueous layer extracted with Et$_2$O (3×50 mL). The combined organic layers were washed with brine, dried over MgSO$_4$ and the solvents removed in vacuo. Column chromatography (hexane:Et$_2$O, 95:5 R$_F$=0.27) furnished the product as a pale yellow oil (0.74 g, 3.3 mmol, 70% yield): $^1$H NMR (400 MHz, CDCl$_3$) δ 5.78 (1H, m, H-5), 5.62 (1H, m, H-6), 4.47 (1H, m, H-9), 4.37 (1H, m, H-8), 2.23 (2H, m, H-7/7'), 2.10 (1H, m, H-4), 1.44 (3H, s, H-1 1), 1.35 (3H, s, H-1I'), 0.95 (9H, s, H-1), 0.04 (3H, s, H-3), 0.02 (3H, s, H-3'); $^{13}$C NMR (100 MHz, CDCl$_3$) δ 127.3 (C-5), 120.7 (C-6), 107.4 (C-10), 74.5 (C-9), 72.7 (C-8), 30.9 (C-4), 28.6 (C-7), 27.3 (C-11), 26.9 (C-1), 25.4 (C-11), 17.3 (C-2), −5.9 (C-3), −6.3 (C-3'); IR (neat, cm$^{-1}$) 3034 (s, C—H), 1647 (m, C=C); MS (CI, m/z) 269.2025 [M+H$^+$].

Example 35 tert-Butyl(2,2-dimethyl-3S,4S,7S-tetrahydro-1,3-benzodioxol-4-yl)dimethylsilane

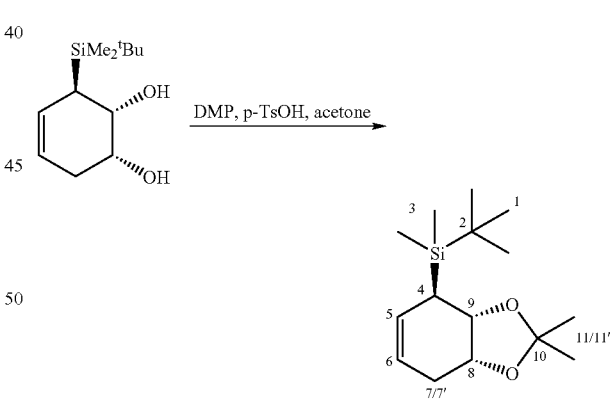

The diol depicted above (0.9 g 4 mmol, 1 eq.) was dissolved in acetone (11.5 mL) and DMP (9 mL). A catalytic amount of p-TsOH (0.025 g, 0.12 mmol, 0.03 eq.) was added and the reaction stirred at room temperature for 2 hours. The solvents were removed in vacuo, saturated Na$_2$CO$_3$ (aq) was added and the aqueous layer extracted with Et$_2$O (3×50 mL). The combined organic layers were washed with brine, dried over MgSO$_4$ and the solvents removed in vacuo. Column chromatography (hexane:Et$_2$O, 95:5 R$_F$=0.27) furnished the product as a pale yellow oil (0.75 g, 2.8 mmol, 70% yield): $[\alpha]_D^{298}$=+151° (c=0.255, CHCl$_3$); $^1$H NMR (400 MHz, CDCl$_3$) δ 5.78 (1H, m, H-5), 5.62 (1H, m, H-6), 4.47 (1H, m, H-9), 4.37 (1H, m, H-8), 2.23 (2H, m, H-7/7'), 2.10 (1H, m, H-4), 1.44 (3H, s, H-11), 1.35 (3H, s, H-11'), 0.95 (9H, s, H-1), 0.04 (3H, s, H-3), 0.02 (3H, s, H-3'); $^{13}$C NMR (100 MHz, CDCl$_3$) δ 127.3 (C-5), 120.7 (C-6), 107.4 (C-10), 74.5 (C-9), 72.7 (C-8), 30.9 (C-4), 28.6 (C-7), 27.3 (C-11'), 26.9 (C-1), 25.4 (C-11), 17.3 (C-2), −5.9 (C-3), −6.3 (C-3'); IR (neat, cm$^{−1}$) 3034 (s, C—H), 1647 (m, C=C); MS (CI, m/z) 269.2025 [M+H$^+$].

Example 36

Trimethyl(3,6,7,7-tetrahydrospiro[1,3-benzodioxole-2,1'-cyclohexan]-4-yl)silane

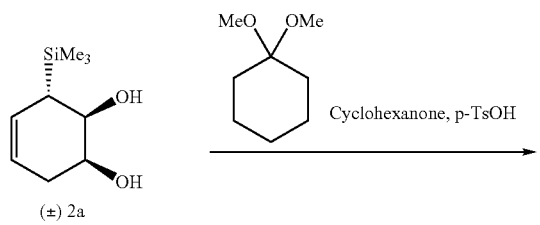

The diol of Example 28 (0.186 g, 1 mmol, 1 eq.) was dissolved in cyclohexanone (3 mL) and cyclohexanone, 1,2-dimethoxyketal (3 mL). A catalytic amount of p-TsOH (0.006 g, 0.03 mmol, 0.03 eq.) was added and the reaction stirred at room temperature for 2 hours. The solvents were removed in vacuo and sat. Na$_2$CO$_3$ (10 mL) was added. The aqueous layer was extracted with Et$_2$O (3×20 mL) and the combined organic layers were washed with brine, dried over MgSO$_4$ and the solvent removed in vacuo. Column chromatography (hexane:Et$_2$O, 90:10; R$_F$=0.3) furnished the product as a colourless oil (0.181 g, 0.8 mmol, 80% yield): $^1$H NMR (400 MHz, CDCl$_3$) δ 5.71 (1H, m, H-3), 5.60 (1H, dt, J$_{4-3}$=10 Hz, J$_{4-5/5'}$=4.4 Hz, H-4), 3.85 (1H, m, H-7), 4.32 (1H, , H-6), 2.23 (1H, m, H-6), 2.23-2.17 (2H, m, H-5/5'), 1.91 (1H, m, H-2), 1.67-1.55 (8H, m, H-9/9'/10/10'/12/12'/13/13'), 1.42-1.35 (2H, m, H-11/11'), 0.06 (9H, s, H-1); $^{13}$C NMR (100 MHz, CDCl$_3$) δ 126.1 (C-3), 121. (C-4), 108.2 (C-8), 73.4 (C-7), 72.0 (C-6), 37.3 (C-9), 35.0 (C-13), 31.5 (C-2), 28.8 (C-5), 25.3 (C-11), 24.1 and 23.8 (C-10 and 12), −2.5 (C-1); IR (neat, cm$^{−1}$) 2936 (s, C—H), 1675 (w, C=C) HRMS (CI, m/z) with M: C$_{15}$H$_{26}$O$_2$Si calc. 267.1780, found 267.1788 [M+H$^+$].

Example 37

5-Fluoro-2,2-dimethyl-3,4,5,7-tetrahydro-1,3-benzodioxoles

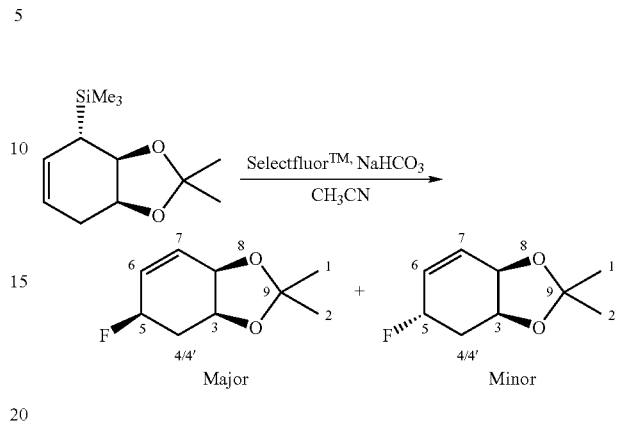

A solution of the allylsilane of Example 33 0.736 g, 3.25 mmol, 1 eq.) and NaHCO$_3$ (0.0.325 g, 3.8 mmol, 1.2 eq.) in anhydrous CH$_3$CN (40 mL) was treated with Selectfluor™ (1.3 g, 3.6 mmol, 1.1 eq.) and the mixture stirred at room temperature for 3 days. Water was added and the mixture extracted with Et$_2$O (3×50 mL). The combined organic layers were washed with brine (50 mL), dried over MgSO$_4$ and the solvent removed in vacuo. Column chromatography (hexane: Et$_2$O, 90:10) furnished the major and mino diastereomers depicted above with a total yield of 64%, in a ratio of 2.3:1. For the major, syn isomer (0.232 g, 1.35 mmol): R$_F$=0.25; $^1$H NMR (400 MHz, CDCl$_3$) δ 6.07 (1H, m, H-7), 6.00 (1H, m, H-5), 5.94 (H-1, m, H-6), 4.47 (1H, m, H-8), 4.32 (1H, m, H-3), 2.56 (1H, m, H-4), 2.09 (1H, m, H-4'), 1.50 (3H, s, H-1/2), 1.39 (3H, s, H-1/2); $^{13}$C NMR (125 MHz, CDCl$_3$) δ 130.3 (C-7), 127.6 (C-6), 85.6 (C-5), 84.2 (C-5), 74.0 (C-3), 63.9 (C-8), 32.0 (C-4), 28.1 (C-1), 26.2 (C-2); $^{19}$F {$^1$H} (376 MHz, CDCl$_3$) δ −176.49; IR (neat, cm$^{−1}$) 2987 (m, C—H), 1648 (w, C=C); HRMS (CI, m/z) with M: C$_9$H$_{13}$O$_2$F calc. 137.0978, found 173.0970 [M+H$^+$]. For the minor anti isomer: (0.124 g, 0.72 mmol) R$_F$=0.38; $^1$H NMR (400 MHz, CDCl$_3$) δ 6.02 (1H, tdd, J$_{2-1/F}$=11.6 Hz, J$_{2-3}$=2.4 Hz, J$_{2-6}$=1.2 Hz, H-2), 5.28-5.12 (1H, m, H-1), 5.28-5.12 (1H, m, J$_{3-F}$=49.2 Hz, H-3), 4.51 (2H, m, H-5/6), 2.60 (1H, m, H-4), 1.91 (1H, m, H-4'), 1.37 (6H, s, H-8/9); $^{13}$C NMR (100 MHz, CDCl$_3$) δ 129.7 (C-2), 128.8 (C-1), 108.8 (C-7), 84.9 (d, J$_{3-F}$=162 Hz, C-3), 71.2 and 71.1 (C-5 and 6), 32.3 (C-4), 26.2 (C-8/9); $^{19}$F {$^1$H} (376 MHz, CDCl$_3$) δ −179.46; IR (neat, cm$^{−1}$) 2987 (m, C—H), 1648 (w, C=C); HRMS (GCT, EI, m/z) with M: C$_9$H$_{13}$O$_2$F calc. 137.0978, found 173.0975 [M+H$^+$].

Example 38

5-Fluoro-2,2-dimethyl-3,4,5,7-tetrahydro-1,3-benzodioxoles

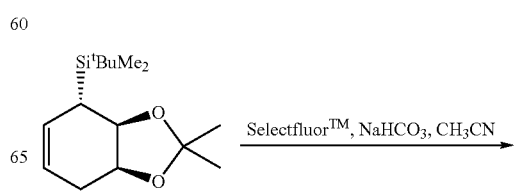

-continued

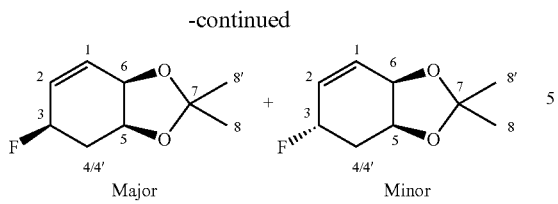

The allylsilane of Example 34 (0.723 g, 2.7 mmol, 1 eq.) and NaHCO$_3$ (0.27 g, 3.24 mmol, 1.2 eq.) in CH$_3$CN (33 mL) was treated with Selectfluor™ (1.0 g, 3 mmol, 1.1 eq.) and stirred at room temperature for 3 days. H$_2$O (30 mL) was added and the aqueous layer was extracted with Et$_2$O (3×50 mL). The combined organic layers were washed with brine, dried over MgSO$_4$ and the solvent removed in vacuo. Column chromatography (90:10 hexane:Et$_2$O) furnished the major and minor diastereomers depicted above in a ratio of 2.1:1. For the major syn isomer: (0.161 g, 0.94 mmol) $R_F$=0.25; $[\alpha]^{298}{}_D$=−24.8° (c=0.145, CHCl$_3$); $^1$H NMR (400 MHz, CDCl$_3$) δ 6.07 (1H, m, H-7), 6.00 (1H, m, H-5), 5.94 (H-1, m, H-6), 4.47 (1H, m, H-8), 4.32 (1H, m, H-3), 2.56 (1H, m, H-4), 2.09 (1H, m, H-4'), 1.50 (3H, s, H-1/2), 1.39 (3H, s, H-1/2); $^{13}$C NMR (100 MHz, CDCl$_3$) δ 130.3 (C-7), 127.6 (C-6), 85.6 (C-5), 84.2 (C-5), 74.0 (C-3), 63.9 (C-8), 32.0 (C-4), 28.1 (C-1), 26.2 (C-2); $^{19}$F {$^1$H} (376 MHz, CDCl$_3$) δ −176.49; IR (neat, cm$^{-1}$) 2987 (m, C—H), 1648 (w, C═C); HRMS (CI, m/z) with M: C$_9$H$_{13}$O$_2$F calc. 137.0978, found 173.0970 [M+H$^+$]; For the minor anti isomer (0.06 g, 0.35 mmol): $R_F$=0.38; $[\alpha]^{298}{}_D$=−42.4 (c=0.125, CHCl$_3$); $^1$H NMR (400 MHz, CDCl$_3$) δ 6.02 (1H, tdd, J$_{2-1/F}$=11.6 Hz, J$_{2-3}$=2.4 Hz, J$_{2-6}$=1.2 Hz, H-2), 5.28-5.12 (1H, m, H-1), 5.28-5.12 (1H, m, J$_{3-F}$=49.2 Hz, H-3), 4.51 (2H, m, H-5 and 6), 2.60 (1H, m, H-4), 1.91 (1H,m, H-4'), 1.37 (6H, s, H-8 and 9); $^{13}$C NMR (100 MHz, CDCl$_3$) δ 129.7 (C-2), 128.8 (C-1), 108.8 (C-7), 84.9 (d, J$_{3-F}$=162 Hz, C-3), 71.2 and 71.1 (C-5 and 6), 32.3 (C-4), 26.2 (C-8 and 9); $^{19}$F NMR (376 MHz, CDCl$_3$) δ −179.46; (neat, cm$^{-1}$) 2987 (m, C—H), 1648 (w, C═C); HRMS (CI, m/z) with M: C$_9$H$_{13}$O$_2$F calc. 137.0978, found 173.0975 [M+H$^+$].

Example 39

(3,5,7)-5-Fluoro-3,4,5,7-tetrahydrospriro[1,3-benzodiozole-2,1'-cyclohexane]

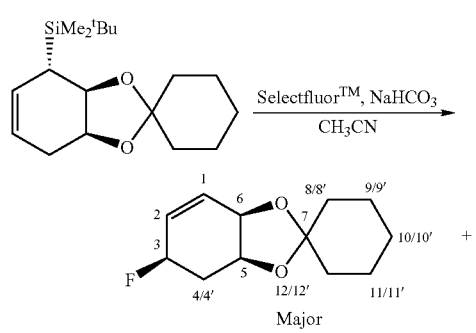

The allylsilane produced in Example 36 (0.149 g, 0.66 mmol, 1 eq.) and NaHCO$_3$ (0.066 g, 0.8 mmol, 1.2 eq.) in CH$_3$CN (8 mL) was treated with Selectfluor™ (0.26 g, 0.7 mmol, 1.1 eq.) and the reaction mixture stirred at room temperature for 3 days. Water (10 mL) was added, and the aqueous layer was extracted with Et$_2$O (3×10 mL). The combined organic layers were washed with brine, dried over MgSO$_4$ and the solvent removed in vacuo. Column chromatography (hexane:Et$_2$O, 95:5) furnished the major and minor diastereomers in a ratio of 1.3:1, with an overall yield of 60%. For the major, syn isomer (0.036 g, 0.17 mmol): $R_F$=0.24; $^1$H NMR (400 MHz, CDCl$_3$) δ 6.06 (1H, m, H-2), 5.96 (1H, m, H-1), 5.02 (1H, m, J$_{3-F}$=48 Hz, H-3), 4.46 (1H, m, H-6), 4.31 (1H, m, H-5), 2.27 (1H, dddd, J$_{4-F}$=14.4 Hz, J$_{4-4'}$=13.2 Hz, J$_{4-5}$=5.2 Hz, J$_{4-3}$=4.8 Hz, H-4), 2.04 (1H, ddt, J$_{4'-4}$=13.2 Hz, J$_{4'-5}$=8.4 Hz, J$_{4'-3}$=8.0 Hz, H-4'), 1.64 (8H, m, H-8/8'/9/9'/11/11'/12/12'), 1.40 (2H, m, 10/10'); $^{13}$C NMR (100 MHz, CDCl$_3$) δ 130.7 (C-2), 127.5 (C-1), 110.8 (C-7), 85.2 (d, J$_{C-F}$=133 Hz, C-3), 70.7 (C-6), 70 2 (C-5), 37.9 (C-8), 35.6 (C-12), 32.3 (C-4), 25.0 (C-9/11), 24.0 (C-9/11); $^{19}$F {$^1$H} NMR (376 MHz, CDCl$_3$) δ −177.12; IR (neat, cm$^{-1}$), 2936 (s, C—H), 1654 (w, C═C); HRMS (CI, m/z) with M: C$_{12}$H$_{17}$O$_2$F, calc. 213.1291, found, 213.1289 [M+H$^+$]. For the minor, anti isomer (0.047 g, 0.22 mmol): $R_F$=0.14; $^1$H NMR (400 MHz, CDCl$_3$) δ 5.99 (1H, m, H-2), 5.81 (1H, m, H-1), 5.28-5.12 (1H, m, J$_{3-F}$=49.6, H-3), 4.47 (2H, m, H-5 and H-6), 2.56 (1H, m, H-4), 1.90 (1H, dddd, J$_{4-F}$=24.0 Hz, J$_{4-4'}$=14.4 Hz, J$_{4-5}$=8.8 Hz, J$_{4-3}$=2.8 Hz, H-4), 1.58 (8H, m, H-8/8'/9/9'/11/11'/12/12'), (1.37, 2H, H-10/10'); $^{13}$C NMR (100 MHz, CDCl$_3$) δ 129.5 (d, J$_{1-F}$=21.5 Hz, C-2), 129.1 (d, J$_{2-F}$=9.5 Hz, C-1), 109.4 (C-7), 85.1 (d, J$_{3-F}$=161.6 Hz, C-3), 71.9 (C-6), 70.7 (C-5), 37.4 (C-8), 35.7 (C-12), 32.4 (C-4), 25.0 (C-10), 24.0 (C-9/11); $^{19}$F {$^1$H} NMR (376 MHz, IR (neat, cm$^{-1}$), 2934 (s, C—H), 1655 (w, C═C); HRMS (CI, m/z) with M:C$_{12}$H$_{17}$O$_2$F calc. 213.1291 found 213.1288 [M+H$^+$].

Example 40

3-(Trimethylsilyl)prop-2-yn-1-ol

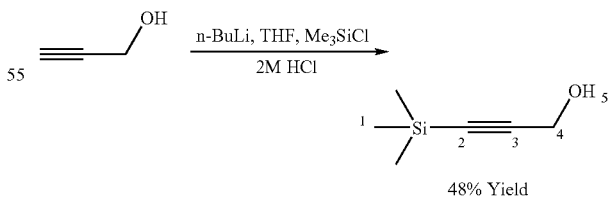

48% Yield n-BuLi (27.3 mL, 44 mmol, 2.2 eq.) was added dropwise to a stirred solution of 2-propyn-1-ol (1.16 mL, 20 mmol, 1 eq.) in THF (60 mL) at −78° C. under argon. After 20 minutes, trimethylsilyl chloride (52 mL, 60 mmol, 2 eq.) was added dropwise and the mixture allowed to warm to room temperature. 2M HCl (40 mL) was added at 0° C., and the reaction mixture was stirred at room temperature for 16 hours. The organic layer was separated and the aqueous layer extracted with Et$_2$O (3×60 mL), the combined organics were washed with brine, dried over MgSO$_4$ and the solvent removed in vacuo. Column chromatography (cyclohexane followed by Et$_2$O), distillation using Kugelrohr apparatus (95-100° C., 11 mbar) and further column chromatography (hexane:Et$_2$O 60:40) furnished the product (0.96 g, 7.5 mmol, 37% yield) as a colourless liquid. R$_f$=0.55 (cyclohexane:Et$_2$O 1:1); $^1$H NMR (400 MHz, CDCl$_3$) δ 4.28 (2H, s, H-4), 1.64 (1H, s, H-5), 0.18 (9H, s, H-1); $^{13}$C NMR (100 MHz, CDCl$_3$) δ 104.10 (C-3), 91.03 (C-2), 51.99 (C-4), 0.00 (C-1); IR (neat, cm$^{-1}$) 3426 (b, OH), 2253 (s, C≡C); MS (lit.- Bunce, R.; Hertzler, D., *J. Org. Chem* 1986, 51, 3451-3453: m/z 128.0695).

Example 41

(2E)-3-(Trimethylsilyl)prop-2-en-1-ol

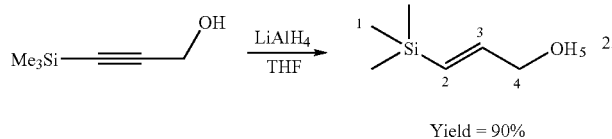

Yield = 90%

The alcohol produced in Example 40 (1.54 g, 12 mmol, 1 eq) in dry THF (12 mL) was added dropwise, with stirring, to a suspension of LiAlH$_4$ (0.7 g, 18 mmol, 1.5 eq) in THF (15 mL) at room temperature, under argon. The mixture was then refluxed for 4 hours and quenched with sat. NH$_4$.Cl. This was extracted with Et$_2$O (3×50 mL) and the combined organic layers were washed with brine, dried over MgSO$_4$ and the solvent removed in vacuo to furnish the product (1.39 g, 10.6 mmol, 89% yield) as a colourless liquid. $^1$H NMR (400 MHz, CDCl$_3$) δ 6.19 (1H, m, H-3), 5.93 (1H, dt, J$_{2-3}$=18.8 Hz, J$_{2-4}$=1.45 Hz, H-2), 4.18 (2H, dd, J$_{4-3}$=2.72, J$_{4-2}$=1.45, H-4), 1.56 (1H, s, H-5), 0.09 (9H, s, H-1); $^{13}$C NMR (100 MHz, CDCl$_3$) δ 144.8 (C-3), 129.5 (C-2), 65.5 (C-4), −1.37 (C-5); IR (neat, cm$^{-1}$) 3331 (b, OH) 1622 (s, C=C).

Example 42

(2E)-3-(Trimethysilyl)acrylaldehyde

Solid PCC (15.9 g, 73.6 mmol. 1.1 eq) was added to a stirring solution of the alcohol produced in Example 41 (8.7 g, 70 mmol, 1 eq.) in DCM (170 mL) and the mixture was stirred at room temperature for 6 hours. The solution was filtered through celite and the remaining precipitate rinsed with Et$_2$O. The combined filtrates were washed with sat. NaHCO$_3$ (4×100 mL) and brine (100 mL), dried over MgSO$_4$, and the solvent removed in vacuo to furnish the aldehyde product. (Due to complexation with chromium the product could not be isolated, hence the crude product was used directly in the subsequent stage of the synthesis.)

Example 43

(3E)-1,4,bis(trimethylsilyl)but-3-en-2-ol

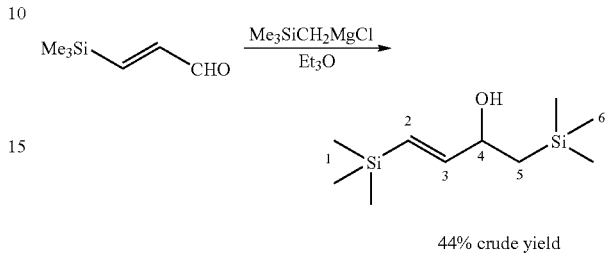

44% crude yield

Chloromethyltrimethylsilane (0.17 mL, 1.2 mmol, 1.2 eq.) in dry Et$_2$O (0.5 mL) was added to magnesium turnings (0.030 g, 1.2 mmol, 1.2 eq.) in dry Et$_2$O (1 mL) and the mixture was refluxed for 1 hour. The aldehyde produced in Example 42 (0.128 g, 1 mmol, 1 eq.) in dry Et$_2$O (1 mL) was added dropwise at 0° C. and the mixture refluxed for 4 hours. After cooling, sat. NH$_4$Cl was added and the mixture extracted with Et$_2$O, washed with brine, dried over MgSO$_4$ and the solvent removed in vacuo to furnish the product (0.096 g, 0.4 mmol, 44% crude yield.) (Due to complexation with chromium the product could not be isolated, hence the crude product was used directly in the subsequent stage of the synthesis.)

Example 44

(1E)-buta-1,3-diene-1-yl(trimethyl)silane

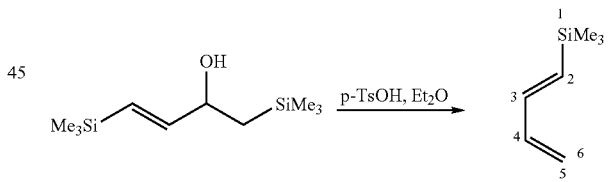

The alcohol produced in Example 43 (15 g, 69 mmol, 1 eq.) was stirred in dry Et$_2$O (70 mL) with a catalytic amount of p-TsOH for 0.5 hours at room temperature. The organic layer was washed with H$_2$O and brine, dried over MgSO$_4$ and the solvent removed in vacuo. Column chromatography (30-40° C. petrol) R$_f$=0.9 furnished the product (1.761 g, 14 mmol) as a colourless oil, 18% yield from the compound produced in Example 40 over 4 steps. $^1$H NMR (400 MHz, CDCl$_3$) δ 6.53 (1H, dd, J$_{3-2}$=18.4 Hz, J$_{3-4}$=10 Hz, H-3), 6.36 (1H, ddd, J$_{4-6}$=16.8 Hz, J$_{4-5}$=10 Hz, J$_{4-3}$=10 Hz, H-4), 5.90 (1H, d, J$_{2-3}$=18.4 Hz, H-2), 5.24 (1H, dd, J$_{6-4}$=16.8 Hz, J$_{6-5}$=1.2 Hz, H-6), 5.12 (1H, dd, J$_{5-4}$=10 Hz, J$_{5-6}$=1.2 Hz, H-5), 0.10 (9H, s, H-1); $^{13}$C NMR (100 MHz, CDCl$_3$) δ 144.6 (C-3), 139.8 (C-4), 134.8 (C-2), 117.6 (C-5), −1.4 (C-1); IR (CDCl$_3$, cm$^{-1}$) 1,570 (m, C=C), 835 (m, trans-HC=CH) MS (lit.-

Vogel, P.; Roversi, E.; Monnat, F., *Helvetica Chimica Acta* 2002, 85, 733-760: 126 [M+]).

Example 45

(Trimethylsilyl)-3,4,7,7-tetrahydro-2-benzofuran-1,3-dione

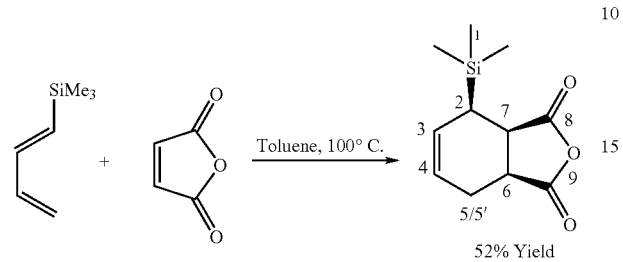

52% Yield

Maleic anhydride (0.098 g, 1 mmol, 1 eq.) was added to a stirring solution of the diene (0.14 g, 1.1 mmol, 1.1 eq.) in dry toluene (5 mL) under argon and the mixture refluxed for 24 hours then the solvent was removed in vacuo. Recrystalisation from cyclohexane furnished the cycloadduct product (0.117 g, 0.52 mmol, 52% yield) as a white solid. MP 116-118° C.; $^1$H NMR (400 MHz, CDCl$_3$) δ 6.1 (1H, m, H-3), 6.0 (1H, m, H-4), 3.4 (2H, m, H-6 and 7) 2.6 (1H, m, H-5), 2.3 (1H, m, H-5'), 1.6 (1H, m, H-2), 0.1 (9H, s, H-1); $^{13}$C NMR (125 MHz, CDCl$_3$) δ 172.6 (C-8 or 9), 170.0 (C-8 or 9), 123.0 (C-3), 128.3 (C-4), 41.1 (C-6), 37.4 (C-7), 25.0 (C-2), 24.8 (C-5), −0.12 (C-1); IR (CDCl$_3$, cm$^{-1}$) 1643 (s, C═O); MS (CI, m/z) 224.0868 [M+H+].

Example 46 tert-butyl-(4R)-2,2-dimethyl-4-vinyl-1,3-oxazolidine-3-carboxylate

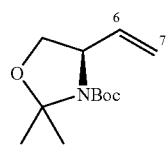

Methyltriphenylphosphonium bromide (3.000 g, 8.6 mmol) was suspended in THF (30 ml) under N$_2$ at room temperature, and nBuLi (2.5M in hexanes) (3 ml, 1.8 eq.) was added. The resulting yellow suspension was heated to 60° C. and stirred for 1 hour. After an hour the mixture was cooled to −78° C. and a cold (−78° C.) solution of Garner's aldehyde (0.962 g, 4.2 mmol) in anhydrous THF (7.3 ml) was added dropwise. The solution was then allowed to stir for 12 hours and monitored by t.l.c. (diethyl ether:hexane, 1:4), before quenching with methanol (10 ml). The resulting mixture was poured into a solution of saturated potassium sodium tartrate and water (1:1, 120 ml), and then concentrated under reduced pressure to remove the TIF and methanol, before extracting with ether. The organic phase was then dried over MgSO$_4$ and concentrated under reduced pressure. Purification by flash chromatography (diethyl ether:hexane, 1:4) afforded the olefin product (0.766 g, 81%). MS(CI)+ m/z: calculated mass for C$_{12}$H$_{21}$NO$_3$ is 227.30, found 227.1917 ([M+]); IR (film) ν$_{max}$ (cm$^{-1}$) 1700, 1385; $^1$H NMR (CDCl$_3$, 400 Mhz), δ=5.82 (m, 1H, H$_6$), 5.17 (m, 2H, H$_{7,7'}$), 4.35 (m, 1H, H$_4$), 4.04 (dd, J=8.8, 6.1 Hz, 1H, H$_5$), 3.74 (ddd, J=8.8, 6.6, 2.3 Hz, 1H, H$_{5'}$), 1.60 and 1.51 (2s, 6H, —OC(CH$_3$)$_2$N—), 1.44 (s, 9H, COOC(CH$_3$)$_3$); $^{13}$C-NMR (CDCl$_3$, 100.6 MHz) δ=152.0 (—N<u>C</u>OO—), 137.4 (CH, C$_6$), 115.7 (CH$_2$, C$_7$), 94.0 (—O<u>C</u>(CH$_3$)$_2$N—), 79.6 (O<u>C</u>(CH$_3$)$_3$), 68.1 (CH$_2$, C$_5$), 60.0 (CH, C$_4$), 28.4 (CH$_3$, OC(<u>C</u>H$_3$)$_3$), 26.5 and 23.7 (CH$_3$, —OC(CH$_3$)$_2$N—); [α]$^D$=+14.5° (lit.- T. Moriwake, S.-I. Hamano, S. Saito, S. Torii, *Chem. Lett.*, 1987, 2085. +15°)

Example 47 tert-butyl-(4R)-2,2-dimethyl-4-(3-trimethylsilanyl-propenyl)-1,3-oxazolidine-3-carboxylate

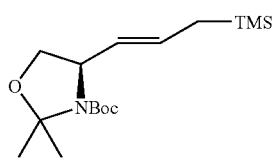

To a solution of the olefin product of Example 46 (0.227 g, 1 mmol) in CH$_2$Cl$_2$ (3 ml) was added titanium isopropoxide (0.09 ml, 30 mol %), the reaction mixture was then refluxed at 45° C. under an atmosphere of argon. After 1 hour, the reaction was cooled to room temperature and allyl trimethyl silane (0.47 ml, 3 mmol) was added. The reaction was then heated to reflux (45° C.), and Grubbs second generation catalyst (0.0849 g, 10 mol %) was then added as a solid (in four portions over 48 hours), the reaction was left to reflux for 48 hours and was monitored by t.l.c. The mixture was then concentrated under reduced pressure. Purification by flash chromatography (diethyl ether:hexane, 1:4) afforded the product (0.202 g, 65%). E:Z=6:1 after purification. (FI)+ m/z: HRMS required for C$_{16}$H$_{31}$NO$_3$Si, calculated mass is 313.2073, found 313.2079 ([M+]); IR (film) ν$_{max}$ (cm$^{-1}$) 1700, 1385; $^1$H NMR (CDCl$_3$, 400 Mhz), δ=5.80 (m, 1H, H$_6$), 5.28 (m, 1H, H$_7$), 4.25 (m, 1H, H$_4$), 4.01 (dd, J=8.7, 6.0 Hz, 1H, H$_5$), 3.70 (dd, J=8.6, 1.9 Hz, 1H, H$_{5'}$), 1.52 (m, 17H, OC(CH$_3$)$_2$N, OC(CH$_3$)$_3$ and H$_{8,8'}$), 0.07 and 0.01 (2s, 9H, Si(CH$_3$)$_3$); $^{13}$C-NMR (CDCl$_3$, 100.6 MHz) δ=152.0 (—N<u>C</u>OO—), 131.0, 129.5, 128.0, 124.3 (4CH, C$_{6cis,trans}$ and C$_{7cis,trans}$), 93.6 (O<u>C</u>(CH$_3$)$_2$N), 79.6 (O<u>C</u>(CH$_3$)$_3$), 68.1 (CH$_2$, C$_5$), 59.3 (CH, C$_4$), 28.6 (CH$_3$, OC(<u>C</u>H$_3$)$_3$), 26.5 and 23.8 (CH$_3$, —OC(CH$_3$)$_2$N—), 22.6 (CH$_2$, C$_8$), −1.3 and −2.0 (CH$_3$, Si(CH$_3$)$_3$); [α]$^D$=−27.7°.

Example 48 tert-Butyl-(4S)-4-(1-fluoroprop-2-en-1-yl)-2,2-dimethyl-1,3-oxazolidine-3-carboxylate

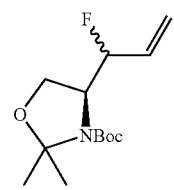

To a solution of the compound produced in Example 47 (0.196 g, 0.63 mmol) in acetonitrile (6 ml), was added Selectfluor™ (0.33 g, 1.5 eq.) and NaHCO$_3$ (0.105 g, 2 eq.). The reaction mixture was stirred under an atmosphere of nitrogen for 20 hours before concentrating under reduced pressure. Purification by flash chromatography (diethyl ether:hexane 1:19) afforded the product (0.116 g, 72%). de=33%.

m/z: HRMS required for C$_{13}$H$_{22}$NO$_3$F, calculated mass is 259.1584 and found 259.1573 ([M$^+$]); IR (film) ν$_{max}$ (cm$^{-1}$) 1703, 1387, 1174; $^1$H NMR (CDCl$_3$, 400 Mhz), δ=5.84 (m, 1H, H$_7$), 5.33 (m, 2H, H$_{8,8'}$), 5.05 (m, 1H, H$_6$), 4.00 (m, 3H, H$_{5,5',4}$), 1.48 (m, 15H, NCOOC(CH$_3$)$_3$ and —OC(CH$_3$)$_2$N—); $^{13}$C-NMR (CDCl$_3$, 100.6 MHz) δ=152.4 (—N<u>C</u>OO—), 133.4 (CH, C$_7$), 118.1 (CH$_2$, C$_8$), 94.0 (O<u>C</u>(CH$_3$)$_2$N), 90.6 (CH, C$_6$), 80.6 (O<u>C</u>(CH$_3$)$_3$), 62.8 and 59.6 (2C, C$_5$, C$_4$), 28.4 (CH$_3$, OC(<u>C</u>H$_3$)$_3$), 26.8 and 24.6 (CH$_3$, —OC(<u>C</u>H$_3$)$_2$N—); $^{19}$F-NMR (CDCl$_3$, 400 MHz) δ=−190.4, −194.7.

Example 49 tert-Butyl-(4S)-4-(1-fluorohexadec-2-enyl)-2,2-dimethyl-1,3-oxazolidine-3-carboxylate

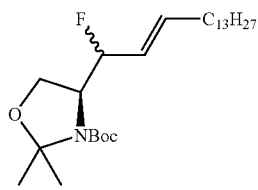

tert-Butyl-(4S)-4-(1-fluoroprop-2-en-1-yl)-2,2-dimethyl-1,3-oxazolidine-3-carboxylate (0.036 g, 0.14 mmol) and 1-pentadecene (0.2 ml, 5 eq) were solubilised in anhydrous CH$_2$Cl$_2$ (2.5 ml) under an atmosphere of nitrogen, in a sealed tube. Grubbs 2$^{nd}$ Generation catalyst (0.006 g, 2 mol %) was added as a solid, and the reaction mixture was allowed to stir for 36 hours at 100° C., with the reaction monitored by t.l.c. (ether:hexane, 1:19). The reaction mixture was then cooled to room temperature and concentrated under reduced pressure. Purification by flash chromatography (ether:hexane, 1:19) afforded the product (0.062 g, quantitative yield) and a mixture of compounds of varying alkyl chain length. Tentative analysis of this compound describes a mixture of products.

m/z: HRMS required for C$_{26}$H$_{48}$FNO$_3$ mass is 441.3600, found 441.3618 as major compound, also found 413.3164, 427.3433, 455.3875 and 469.3886 as minor products; IR (film) ν$_{max}$ (cm$^{-1}$) 2926, 1704, 1386; $^1$H NMR (CDCl$_3$, 400 Mhz) δ=5.81 (m, 1H, H$_8$), 5.51 (m, 1H, H$_7$), 5.10 and 4.94 (2 m, H$_{6 erythreo, threo}$), 4.08 (m, 1H, H$_4$), 3.94 (m, 2H, H$_{5,5'}$), 2.04 (m, 2H, H$_{9,9'}$), 1.48 (m, 15H, NCOOC(CH$_3$)$_3$ and —OC(CH$_3$)$_2$N—), 1.25 (br s, 22H, (CH$_2$)$_{11}$), 0.88 (t, J=7.0, 3H, CH$_3$, H$_{21}$); $^{13}$C-NMR (CDCl$_3$, 100.6 MHz) δ=152.4 (—N<u>C</u>OO—), 136.9 (CH, C$_8$), 125.2 (CH, C$_7$), 94.4 (CH, C$_6$), 93.9 (O<u>C</u>(CH$_3$)$_2$N), 80.4 (OC(CH$_3$)$_3$), 63.4 (CH, C$_4$), 60.4 (CH$_2$, C$_5$), 31.6, 31.9, 29.7, 22.7, 21.0 (12C, CH$_2$, (CH$_2$)$_{12}$), 28.4 (CH$_3$, OC(<u>C</u>H$_3$)$_3$), 26.9 and 24.7 (CH$_3$, —OC(CH$_3$)$_2$N—), 14.1 (CH$_3$, (CH$_2$)$_{12}$<u>C</u>H$_3$)); $^{19}$F-NMR (CDCl$_3$, 400 MHz) δ=major compounds −183.0, −186.0, minor compounds −175.6, −177.7, −192.6, −194.6;

Example 50

Preparation of Compounds wherein R$^6$ and R$^7$ Form a 6-Membered Carbocyclic Group

| Entry | Diene | Dienophile$^a$ | Reaction condition$^b$ | Product(s) | endo exo | Yield |
|---|---|---|---|---|---|---|
| | | | Non-catalysed cycloadditions | | | |
| 1 | SiMe$_3$ diene (1$^{[1]}$) | maleic anhydride | Et$_2$O, rt, 23 h | product 4 | only endo | 50% |
| 2 | | dimethyl acetylenedicarboxylate (CO$_2$Me, CO$_2$Me) | CH$_2$Cl$_2$, reflux, 38 h | product 5 | N/A | 78% |

-continued

| Entry | Diene | Dienophile[a] | Reaction condition[b] | Product(s) | endo exo | Yield |
|---|---|---|---|---|---|---|
| | | | Catalysed cycloadditions | | | |
| 3 | | (MVK) | 0.2 equiv Me$_2$AlCl, CH$_2$Cl$_2$, rt, 20 h | 6 | only endo | 53%[c] |
| 4 | | (methyl acrylate) | 0.2 equiv Me$_2$AlCl, CH$_2$Cl$_2$, reflux, 20 h | Major endo-7, Minor exo-7 | 2.5:1[d] | 88%[c,e] |

[a] 0.8 equiv with respect to 1.
[b] 0.1 mol dm$^{-3}$ solution of 1.
[c] Only para adduct(s) observed.
[d] By integration of the ester methyl protons in the NMR of the crude reaction mixture.
[e] syn (endo) and anti (exo) isomers were not completely separable by column chromatography; nonetheless, small samples of pure endo and exo isomers were obtained. By integration of the ester methyl protons in the NMR of the isomer mixture obtained after column chromatography, the ratio of the two isomers in the mixture was found to be endo:exo = 5:1.

Example 51

Further Examples of Compounds Prepared via this Method Are as Follows:

Table 51A

Diels-Alder reactions of Me$_3$SiCH$_2$C(=CH$_2$)CH=CH-Ph with maleic anhydride, DMAD, MVK and methyl acrylate ([5]=H. Sakurai, A. Hosorni, M. Saito, K. Sasaki, H. Iguchi, J. I. Sasaki and Y. Araki, *Tetrahedron* 1983, 39, 883-894 and [6]=M. G. Organ, D. D. Winkle and J. Huffmann, *J. Org. Chem.* 1997, 62, 5254-5266.):

| Entry | Diene | Dienophile | Reaction condition | Product(s) | Yield |
|---|---|---|---|---|---|
| | | | Non-catalysed cycloadditions | | |
| 1[5] | 3 | maleic anhydride | Et$_2$O, rt, 20 h | | 100% |
| 2[5] | | MeO$_2$C—≡—CO$_2$Me | CH$_2$Cl$_2$, reflux, 16.5 h | | 96% |

-continued

| Entry | Diene | Dienophile | Reaction condition | Product(s) | Yield |
|---|---|---|---|---|---|
| 3[5] | | methyl vinyl ketone (CH₂=CH-C(O)CH₃) | $C_6H_6$, 80° C., 36 h | 4-(CH₂SiMe₃)-cyclohex-3-enyl methyl ketone (para) and 3-(CH₂SiMe₃)-cyclohex-3-enyl methyl ketone (meta); para:meta = 83:17 | 83% |
| 4[5] | | methyl acrylate (CH₂=CH-C(O)OMe) | $C_6H_6$, 80° C., 46 h | methyl 4-(CH₂SiMe₃)-cyclohex-3-ene-1-carboxylate (para) and methyl 3-(CH₂SiMe₃)-cyclohex-3-ene-1-carboxylate (meta); para:meta = 84:16 | 58% |

Catalysed cycloadditions

| Entry | Diene | Dienophile | Reaction condition | Product(s) | Yield |
|---|---|---|---|---|---|
| 5[5] | 2-(trimethylsilylmethyl)-1,3-butadiene (3) | methyl vinyl ketone | $C_6H_6$, 0.08–0.1 equiv $AlCl_3$, 15–20° C., 3.5 h | 4-(CH₂SiMe₃)-cyclohex-3-enyl methyl ketone | 64% |
| 6[5] | | methyl acrylate | $C_6H_6$, 0.08–0.1 equiv $AlCl_3$, 50–60° C., 2 h | methyl 4-(CH₂SiMe₃)-cyclohex-3-ene-1-carboxylate (para) and methyl 3-(CH₂SiMe₃)-cyclohex-3-ene-1-carboxylate (meta); para:meta = 99.5:0.5 | 75% |
| 7[6] | | methyl acrylate | $CH_2Cl_2$, 0.2 equiv $Me_2AlCl$, 40° C., 3 h | methyl 4-(CH₂SiMe₃)-cyclohex-3-ene-1-carboxylate | 88% |

In all cycloadditions 0.8 equivalent of dienophile with respect to 1 was used so as to facilitate product isolation. Cycloadduct 4 was purified by recrystallisation, and maleic anhydride might also be crystallised if used in excess. Chromatographic purification of 5-7 was more easily done if the dienophiles were completely consumed, since the $R_f$ values of the dienophiles are closer to those of 5-7 than to the starting diene 1. The yields reported here are not optimised.

Structural Assignment of 4 in Table 51A

In principle, the relative stereochemistry of 4 between the phenyl group and the anhydride moiety could be established by measuring the coupling constant between H-4 and H-3a. However, the resonance of the 2 key H atoms which substitute the 6-membered (non-phenyl) carbocyclic group (those to which the —C(O)—O—C(O)— is attached) overlap as they are chemically similar. Thus, the required information in coupling constants could not be obtained, although one might expect an endo adduct as is usually observed in cycloadditions of maleic anhydride with alkadienes. This was established unambiguously by X-ray crystallography.

The syn relative stereochemistry of 4 follows straightforwardly from the usual boat-like transition state in the cycloaddition in which the anhydride-carbonyl groups are oriented such that bonding interactions are maintained between them and the developing $\pi$ bond at the back of the diene (secondary orbital interactions):

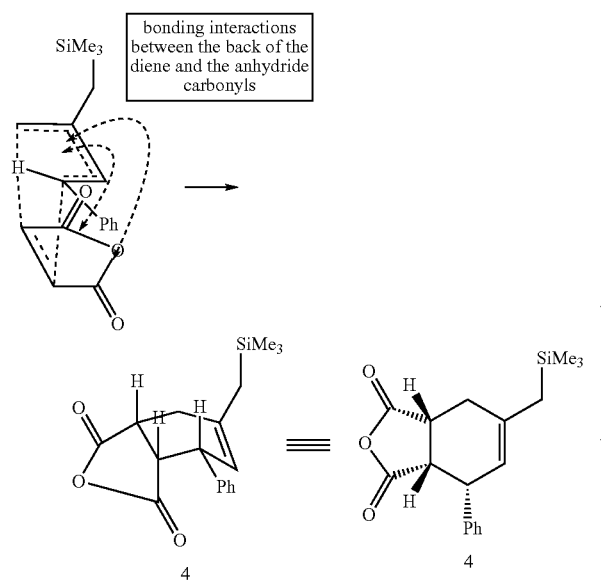

The boat-like transition state in the Diels-Alder reaction gives rise to the endo stereochemistry of 4.

As seen with Dreiding models, two major conformers can be conceived for bicyclic anhydrides such as 4: the "folded" form and the "extended" form resulting from a boat-to-boat inversion of the folded conformer. In general, the former conformer would suffer from allylic 1,2-strain ($A^{[1,2]}$ strain) between an equatorial allylic substituent and a substituent (if any) on the adjacent vinylic carbon, whereas the latter form would be disfavoured by syn-1,4-diaxial (flagpole) interactions with the substituent. The preferential conformation of some bicyclic anhydrides in solution have been studied and seemed to depend on a subtle balance between these two unfavourable steric factors and, thus, on the steric requirements of the ring substituents.

The X-ray structure of 4 clearly showed the folded conformer in the solid state. Due to the overlapping of proton resonances, the solution conformation of 4 was not amenable to study by NMR. However, structures related to 4 have been shown to exist preferentially in the folded conformation in solution:

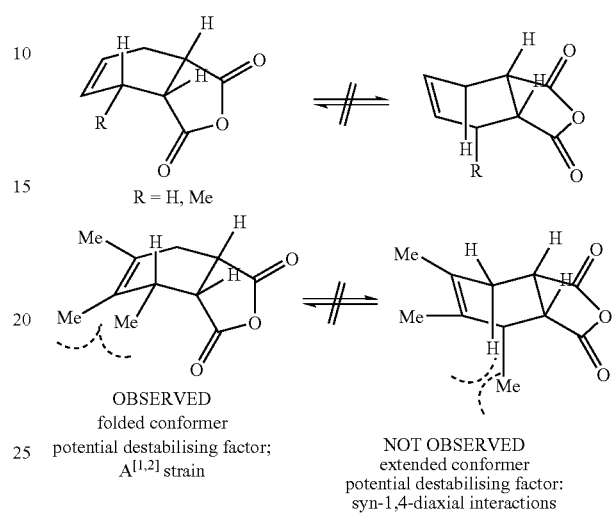

OBSERVED
folded conformer
potential destabilising factor;
$A^{[1,2]}$ strain

NOT OBSERVED
extended conformer
potential destabilising factor:
syn-1,4-diaxial interactions Examples of bicyclic anhydrides adopting the folded conformation in solution. Also shown are the conceivable extended conformers, with the potential destabilising steric interactions in each conformer shown in dashed curves.

It is assumed that this will hold true for 4 as well.

Structural Assignment of 5 in Table 51A

For the cycloadduct with DMAD (Entry 2), the unusually strong homoallylic, 5-bond scalar coupling between the benzylic proton and both of the ring methylene protons was confirmed by COSY($^5J_{HH}$=7.7 Hz). Its large value has been attributed to the two "parallel" $\pi$ bonds which mediate effectively the homoallylic coupling of the two proton spins:

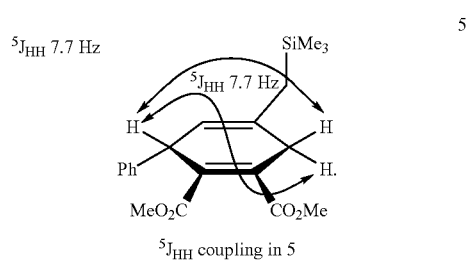

$^5J_{HH}$ coupling in 5

The conformational analysis of cyclohexa-1,4-diene and its derivatives has been a subject of considerable controversy. After intensive investigations it can now be concluded that (unsubstituted) cyclohexa-1,4-diene is planar. For substituted cyclohexa-1,4-dienes, substantial efforts have been made in an attempt to determine their geometric preferences by measurements of NMR coupling constants. To this end model systems of different conformational rigidity have been investigated. (Table 5 1B) The ratio $^5J_H1_{H(cis)}/^5J_H1_{H(trans)}$ in a planar ring has been calculated to be about 1.12. On the other hand, studies on rigidified systems showed that as the ring is increasingly puckered into a boat, the cis-diaxial coupling constant is increased while the trans-axial-equatorial coupling constant is decreased. (Entries (d) & (e), Table 51B) On the basis of this analysis, 1,4-dihydrobenzyl alcohol ((a), Table 51B) and the 3-fluoro-1,4-dihydrobenzyl alcohol ((b), Table 51B) were assigned a planar structure.

For 1-t-butyl-1,4-dihydrobenzene ((c), Table 51B), a very shallow boat structure, with the t-butyl group in the (slightly) pseudo-axial position, was assigned due to a slight deviation of the measured $^5J_H1_{H(cis)}/^5J_H1_{H(trans)}$ from its theoretical value. The planarity of this compound was ruled out on grounds of inequality of the vicinal couplings ($^3J_H1_H2 \neq {}^3J_H3_H4$) and of the allylic couplings ($^4J_H1_H3 \neq {}^4J_H2_H4$), which should be equal in planar systems. As shown in table 51B, 5 could be assigned a very shallow boat structure, although a planar structure could not be completely ruled out as 5 is substituted at C-3 such that $^3J_H3_H4$ and $^4J_H1_H3$ do not exist as in the case of 1-t-butyl-1,4-dihydrobenzene. At any rate, however, the coupling constant values of 5 compare much more favourably to the planar state than full boat (rigid) geometries.

TABLE 51B

Coupling constants pertinent to the conformational analysis of 5 and related systems (The numbering of atoms pertains to the sections "Structural assignment of 5 in table 51A" only.)

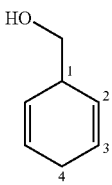

(a)

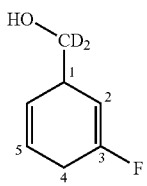

(b)

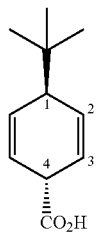

(c)

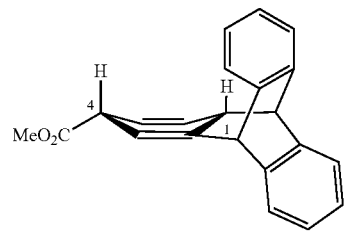

(c)

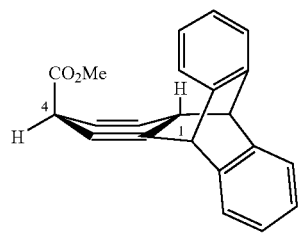

(e)

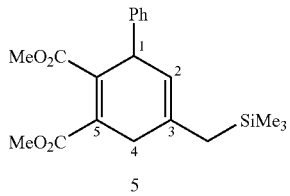

| | Assigned geometry | $^5J_{H^1H^4(cis)}$ | $^5J_{H^1H^4(trans)}$ | $^5J_{H^1H^4(cis)}/$ $^5J_{H^1H^4(trans)}$ | $^3J_{H^1H^2}$ | $^3J_{H^3H^2}$ | $^4J_{H^1H^3}$ | $^4J_{h^2H^4}$ |
|---|---|---|---|---|---|---|---|---|
| (a)[15] | Planar | 8.6 | 7.4 | 1.16 | 3.1 | 3.0 | 1.5 | 1.5 |
| (b)[15] | Planar | 8.3 | 7.5 | 1.11 | 3.4 | 3.5[a] | — | — |
| (c)[17] | Unrestricted shallow boat | — | 7.6 | — | 2.6 | 3.7 | 2.3 | —[b] |
| (d)[15] | Rigid, full boat | 12.0 | — | — | 2.5 | — | 3.0 | 3.0 |
| (e)[15] | Rigid, full boat | — | 4.7 | — | 2.5 | 5.8 | 3.0 | ≧1.0 |
| 5 | Unrestricted shallow boat or planar (see text) | 7.7 | 7.7 | 1 | 3.7 | — | — | — |

— = not applicable or not measured unless otherwise stated.
[a] $^3J_{H^5H^4}$ is given since C-3 iss substituted.
[b] The numerical value of this coupling constant was not given in the original paper, but was reported to be unequal to $^4J_{H^1H^3}$.
[15] = P. W. Rabideau, J. W. Paschal and L. E. Patterson, J. Am. Chem. Soc. 1975, 97, 5700-5704.
[17] = P. W. Rabideau, L. M. Day, C. A. Husted, J. L. Mooney and D. M. Wetzel, J. Org. Chem. 1986, 51, 1681-1686.

Structural Assignment of 6 and 7 in Table 51A

The para-identity (as opposed to the meta-identity) and the relative stereochemistry of the cycloadducts 6 and 7 were readily established by proton and carbon NMR spectroscopy. Small amounts of pure samples of endo- and exo-7 were obtained by column chromatography. The pertinent proton resonances and their assignments (on the grounds of chemical shift) in the para-isomer of 7 were as follows:

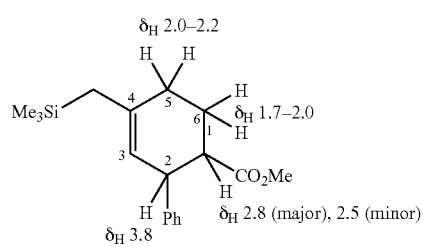

(a)

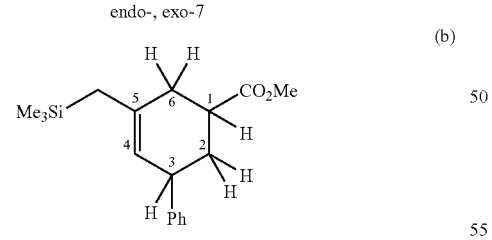

(b)

Structure of endo- and exo-7 and assignments of the $^1H$ resonances (No stereochemistry implied). (b) The alternative meta-isomer of 7.

A COSY spectrum of the major isomer of 7 showed the presence of a simultaneous strong coupling of the methine proton (H-1) to the benzylic proton (H-2) and to the homoallylic ring protons (H-6). It also showed the absence of coupling between this methine proton to the allylic ring protons (H-5). These confirmed the para-identity of the cycloadducts, in which H-1 could exhibit a three-bond coupling with both H-6 and H-2. In the alternative meta-structure ((b) above), this methine proton (H-1) would be expected to couple with the allylic ring protons (H-6) and the homoallylic ring protons (H-2) but not with the benzylic proton, which would be separated from H-1 by four bonds.

That the two cycloadducts 7 are related as endo/exo diastereomers is supported by the fact that they have very similar chemical shifts for most of the carbon resonances. ($\Delta\delta_c$=0-1.6 ppm for 12 of the 14 signals, $\Delta\delta_c$=3.6 ppm for C-1).

The relative stereochemistry of the cycloadducts is established by a combination of coupling constant arguments and NOESY on both cycloadducts 6 and 7. The signal due to the methine proton (H-1) in 6, endo-7 and exo-7 was observed as a doublet of doublets of doublets (ddd). The relevant coupling constants of this signal were as follows:

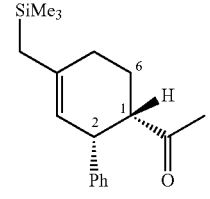

6

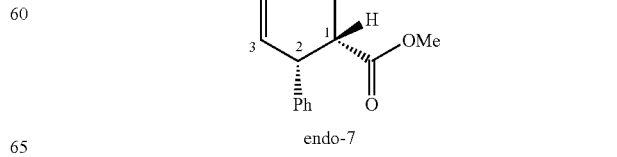

endo-7

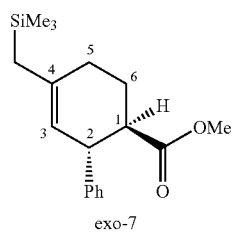

exo-7

|  | 6 | endo-7 | exo-7 |
|---|---|---|---|
| $^3J_{H}1_{H}6/Hz$ | 12.6 | 12.3 | 12.4 |
| $^3J_{H}1_{H}2/Hz$ | 6.0 | 6.1 | 9.3 |
| $^3J_{H}1_{H}6/Hz$ | 2.9 | 3.3 | 3.2 |

Vicinal H—H coupling constants pertinent to the stereochemical assignment of 6 and 7. The sets of coupling constants in 6 and endo-7 are virtually the same, indicating that their relative stereochemistry is the same, and their conformation should be similar. The syn (endo) stereochemistry of 6 was confirmed by NOESY. The spectrum of 6 shows the presence of crosspeaks between H-1 and the benzylic proton (H-2), indicating that they are spatially close to each other, implying that they occupy the same side of the ring. In addition, no crosspeaks were observed between H-1 and the protons on the phenyl ring. This implies that H-1 and the phenyl ring occupy opposite sides of the ring. The stereochemistry of 6 was thus assigned as syn.

The large value of J=12 Hz indicates a diaxial coupling, which implies that H-1 must be axial. The smaller coupling constants (J=6 Hz, 3 Hz) were consistent with axial-pseudoequatorial and axial-equatorial couplings respectively. The conformation of 6 and the structurally similar endo-7 is thus as follows:

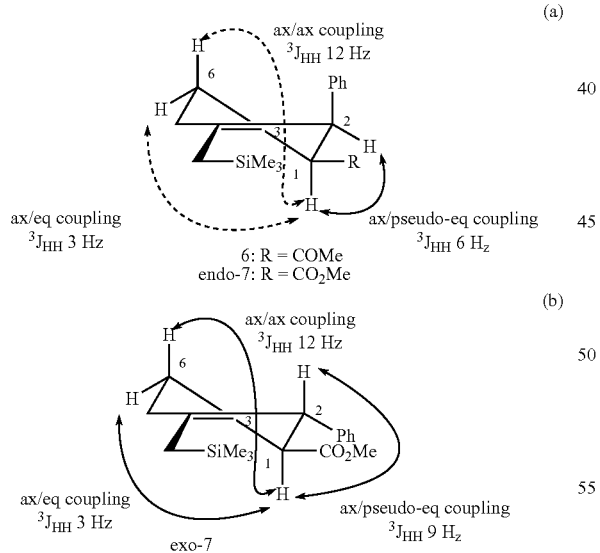

Coupling Assignments of (a) 6 and endo-7, (b) exo-7.

The coupling constants observed in exo-7 can be readily explained by one diaxial coupling (J=12 Hz), one axial-pseudoaxial coupling (J=9 Hz) and one axial-equatorial coupling (J=3 Hz).

The observation that the phenyl group in 6 and endo-7 occupies a pseudoaxial site in spite of its steric bulk may appear counter-intuitive. However, the factor disfavouring an axial bulky group, namely 1,3-diaxial interactions, in a chair is not as severe as in a half-chair, since in a cyclohexene ring there exists only one axial substituent meta from the bulky group in question, rather than two in a cyclohexane. Moreover, the bulky group in a half-chair is not truly axial, thus relieving the 1,3-diaxial strain. In addition, bulky allylic substituents are known to prefer pseudoaxial sites over pseudoequatorial positions, where they experience significant non-bonding repulsive interactions with substituents at the proximal vinylic carbon (allylic 1,2-strain). It is speculated that this is responsible for the disfavouring of the pseudoequatorial position for the phenyl group in 6 and endo-7

Example 52

(Trimethylsilyl)methylmagnesium chloride

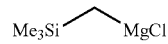

To a well-stirred mixture of magnesium turnings (3.75 g, 154.04 mmol) in 120 mL of THF was added (chloromethyl)trimethylsilane (9.44 g, 77.02 mmol) in 37 mL of THF. The mixture was stirred for 3 h at room temperature to ensure complete generation of the organomagnesium species and was then used fresh.

Example 53

Trimethyl[(3E)-2-methylene-4-phenylbut-3-en-1-yl]silane

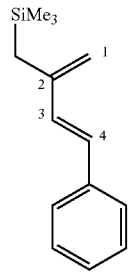

CeCl$_3$.7H$_2$O (28.697 g, 77.02 mmol) was quickly ground with mortar and pestle and dried at 150° C. at 0.1 Torr for 3 hours. The flask was cooled to room temperature and vented to an argon atmosphere. THF (140 mL) was added, and the suspension was stirred at ambient temperature under argon for 2-3 h. The slurry was then cooled to −78° C. (Trimethylsilyl)methylmagnesium chloride in THF (77.02 mmol, freshly prepared as specified above) was run in via syringe. The cream-coloured suspension was stirred at −78° C. for 1 h, at which time ethyl trans-cinnamate (2.71 g, 15.40 mmol) was added over 10 minutes. Stirring is continued for 2 hours at −78° C. Then the reaction was allowed to warm to room temperature overnight. After quenching with NH$_4$Cl (80 mL), the crude bis(silylmethyl)carbinol was isolated by extraction with ether, drying over magnesium sulfate, and removal of solvent under vacuum. Dehydroxysilylation was accomplished by stirring the product with silica gel, which was made by adding 15.4 g silica ("flash" chromatography grade) into 150 mL CH$_2$Cl$_2$, for 3 hours. Filtration, followed by flash chromatography (hexane/ethyl acetate, 10:1), afforded the product (3.166 g, 95%) as a colourless oil. $^1$H NMR (400 MHz) δ: 0.06 (s, 9H, Si(CH$_3$)$_3$), 1.86 (s, 2H, CH$_2$SiMe$_3$), 4.88 (s, 1H, H-1), 5.05 (s, 1H, H-1), 6.48 (d, 1H, $^3J_{HH}$ 16.2, H-4), 6.82 (d, 1H, $^3J_{HH}$ 16.2, H-3), 7.24-7.43 (m, 5H). $^{13}$C NMR (100 MHz) δ: −1.2 (Si(CH$_3$)$_3$), 22.2 (CH$_2$SiMe$_3$), 114.8 (C-1), 126.4 (ortho-Ar—C), 127.3 (para-Ar—C), 128.6, 128.7 (meta-Ar—C, C-4) 132.0 (C-3), 137.5 (C-2), 143.5 (4° Ar—C). IR: 2954, 1598, 1249, 960, 854, 753, 692. HRMS: calcd for C$_{14}$H$_{21}$Si ([M+H]$^+$): 217.1413, found 217.1402.

Example 54 rac-(3aR,4R,7aS)-4-Phenyl-6-[(trimethylsilyl)methyl]-3a,4,7,7a-tetrahydro-2-benzofuran-1,3-dione

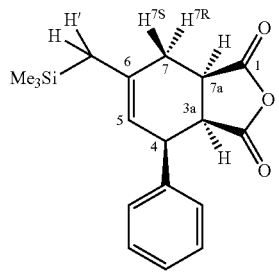

Silylated diene of Example 53 (407 mg, 1.70 mmol) and maleic anhydride (134 mg, 1.37 mmol) were dissolved in 17 mL of diethyl ether. The solution was stirred at room temperature for 20 hours. Evaporation of volatile materials followed by recrystallisation from hexane afforded the cycloadduct product as colourless crystals (278 mg, 50%). $^1$H NMR (400 MHz) δ: 0.06 (s, 9H, Si(CH$_3$)$_3$), 1.65 (d, 1H, $^2J_{HH}$ 13.4, CHH'SiMe$_3$), 1.76 (d, 1H, $^2J_{HH}$ 13.4, CHH'SiMe$_3$), 2.39 (dm, 1H, $^2J_{HH}$ 16.5, H$^{7R}$), 2.74 (d, 1H, $^2J_{HH}$ 16.5, H$^{7S}$), 3.49-3.51 (m, 2H, H-3a, H-7a), 3.76 (broad s, 1H, H-4), 5.73 (broad s, 1H, H-5), 7.23-7.39 (m, 5H, Ph). $^{13}$C NMR (100 MHz) δ: −1.3 (Si(CH$_3$)$_3$), 28.9, 29.1 (CH$_2$Si(CH$_3$)$_3$, C-7), 40.4 (C-7a), 41.4 (C-4), 46.2 (C-3a), 120.6 (C-5), 127.6, 128.5, 128.7 (ortho-, meta-, para-Ar—C), 138.5, 139.2 (4° Ar—C, C-6). 170.6 (C=O), 173.8 (C=O). IR: 1634, 1251, 988, 948. HRMS: calcd for C$_{18}$H$_{26}$NO$_3$Si ([M+NH$_4$]$^+$) 332.1682, found 332.1670. m.p.: 126° C.

Example 55

Dimethyl 3-phenyl-5-[(trimethylsilyl)methyl]cyclohexa-1,4-diene-1,2-dicarboxylate

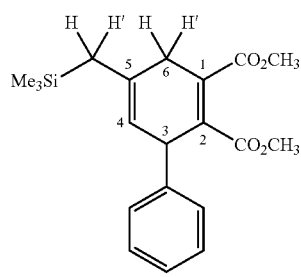

To a stirred solution of silylated diene of Example 53 (300 mg, 1.26 mmol) in 13 mL of CH$_2$Cl$_2$ was added via a microliter syringe dimethyl acetylenedicarboxylate (149 mg, 1.05 mmol). The resulting mixture was heated to reflux for 38 h. The reaction was followed by TLC (hexane/diethyl ether, 4:1). After the complete consumption of the starting dienophile component, the solution was cooled to room temperature and the solvent was removed. The crude reaction mixture was purified by column chromatography (hexane/diethyl ether, 4:1) to afford the product as a thick, colourless oil (350 mg, 78%). R$_f$(hexane/diethyl ether, 2:1): 0.30. $^1$H NMR (500 MHz) δ: 0.08 (s, 9H, Si(CH$_3$)$_3$), 1.56 (d, 1H, $^2J_{HH}$ 13.7, CHH'SiMe$_3$), 1.61 (d, 1H, $^2J_{HH}$ 13.7, CHH'SiMe$_3$), 2.91 (dd, 1H, $^2J_{HH}$ 22.8, $^5J_{HH}$ 7.3, H-6), 3.19 (dd, 1H, $^2J_{HH}$ 22.9, $^5J_{HH}$ 7.6, H'-6), 3.57 (s, 3H, CO$_2$CH$_3$), 3.82 (s, 3H, CO$_2$CH$_3$), 4.39 (td, 1H, $^5J_{HH}$ 7.4, $^3J_{HH}$ 3.7, CHPh), 5.32 (broad s, 1H, C=CH), 7.20-7.34 (m, 5H, Ph). $^{13}$C NMR (125 MHz) δ: −1.1 (Si(CH$_3$)$_3$), 26.7 (CHH'SiMe$_3$), 32.6 (C-6), 45.6 (CHPh), 52.0, 52.3, (CO$_2$CH$_3$), 119.7 (C-5), 127.0 (para-Ar—C), 128.4, 128.6 (ortho-, meta-Ar—C), 130.4, 130.6, (C-1, C-2), 137.7 (C-5), 142.2 (4° Ar—C), 167.9 (CO$_2$CH$_3$), 168.6 (CO$_2$CH$_3$). IR: 3028, 2952, 1728, 1681, 1435, 1262. HRMS: calcd for C$_{20}$H$_{27}$O$_4$Si ([M+H]$^+$): 359.1679, found: 359.1688.

Example 56 rac-1-{(1R,2S)-2-Phenyl-4-[(trimethylsilyl)methyl]cyclohex-3-en-1-yl}ethanone

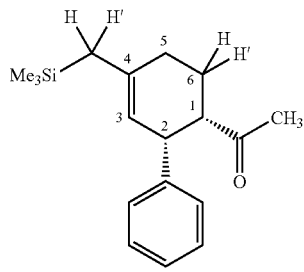

To a stirred solution of silylated diene of Example 53 (500 mg, 2.31 mmol) in 23 mL of CH$_2$Cl$_2$ was added methyl vinyl ketone (154 mg, 2.20 mmol), followed by dropwise addition of dimethylaluminium chloride (0.46 mL of a 1 M solution in hexanes, 0.46 mmol). The mixture was allowed to react at room temperature for 2 h and quenched with a saturated aqueous solution of sodium hydrogencarbonate (15 mL). The layers were separated, and the aqueous layer was extracted twice with diethyl ether. The pooled organic fraction was dried over anhydrous magnesium sulfate. Following solvent removal in vacuo, the crude product was purified by column chromatography (5% ether in hexane) to afford the product as a colourless oil (480 mg, 75%). R$_f$ (hexane/diethyl ether, 14:1): 0.17.$^1$H NMR (400 MHz) δ: 0.09 (s, 9H, Si(CH$_3$)$_3$), 1.52-1.61 (m, 2H, CHH'SiMe$_3$), 1.73-1.78 (m, 1H, H-6), 1.79 (s, 3H, CH$_3$CO), 1.89-1.98 (m, 1H, H'-6), 2.07-2.20 (m, 2H, H-5), 2.87 (ddd, 1H, $^3J_{HH}$ 12.6, $^3J_{HH}$ 6.0, $^3J_{HH}$ 2.9, CHCOMe), 3.88 (t, 1H, $^3J_{HH}$ 5.1, CHPh), 5.33 (dm, 1H, $^3J_{HH}$ 4.9, C=CH), 7.17-7.30 (m, 5H, Ph). $^{13}$C NMR (125 MHz) δ: −1.1 (Si(CH$_3$)$_3$), 20.0 (C-6), 27.7 (C-5), 28.9 (CH$_2$SiMe$_3$), 30.5 (CH$_3$CO), 43.6 (CHPh), 52.7 (CHCOMe), 120.6 (C-4), 126.8 (para-Ar—C), 128.1, 129.3 (ortho-, meta-Ar—C), 136.7 (C-3), 141.2 (4° Ar—C), 211.5 (COMe). IR: 3029, 2951, 1711. HRMS: calcd for $C_{18}H_{27}OSi$ ([M+H]$^+$) 287.1831, found 287.1837.

Example 57

Methyl rac-(1R,2S)-2-Phenyl-4-[(trimethylsilyl)methyl]cyclohex-3-ene-1-carboxylate (endo-7) and Methyl rac-(1R,2R)-2-phenyl-4-[(trimethylsilyl)methyl]cyclohex-3-ene-1-carboxylate (exo-7)

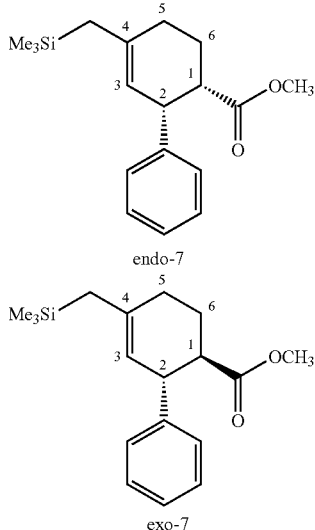

endo-7 exo-7

To a stirred solution of silylated diene of Example 53 (314 mg, 1.26 mmol) in 13 mL of $CH_2Cl_2$ was added methyl acrylate (90.8 mg, 1.05 mmol), followed by dropwise addition of dimethylaluminium chloride (0.25 mL of a 1 M solution in hexanes, 0.25 mmol). The mixture was heated to reflux for 20 h, cooled to room temperature, and quenched with a saturated aqueous solution of sodium hydrogencarbonate (10 mL). The mixture was worked up as for Example 56, followed by solvent removal in vacuo. The crude product was purified by column chromatography (hexane/ethyl acetate, 20:1) to afford a mixture of endo- and exo-7 as a colourless oil (284 mg, 88%). Small amounts of pure endo- and of exo-7 could be separated for NMR characterisation. Major isomer (endo): $R_f$ (hexane/ethyl acetate, 20:1): 0.17. $^1$H NMR (400 MHz) δ: 0.08 (s, 9H, Si(CH$_3$)$_3$), 1.54-1.57 (m, 2H, CH$_2$SiMe$_3$), 1.72-1.90 (m, 2H, H-6), 2.08-2.14 (m, 2H, H-5), 2.88 (ddd, 1H, $^3J_{HH}$ 12.3, $^3J_{HH}$ 6.1, $^3J_{HH}$ 3.3, CHCO$_2$Me), 3.47 (s, 3H, CH$_3$OCO), 3.86 (t, 1H, $^3J_{HH}$ 5.3, CHPh), 5.28-5.34 (dm, 1H, $^3J_{HH}$ 4.9, H-3), 7.16-7.28 (m, 5H, Ph). $^{13}$C NMR (100 MHz) δ: −1.1 (Si(CH$_3$)$_3$), 19.6 (C-6), 27.7 (C-5), 30.4 (CH$_2$SiMe$_3$), 43.2 (CHPh), 45.0 (CHCO$_2$Me), 51.0 (CH$_3$OCO), 120.2 (C-4), 126.8 (para-Ar—C), 127.8, 129.3 (ortho-, meta-Ar—C), 136.9 (C-3), 141.3 (4° Ar—C), 174.4 (CO$_2$CH$_3$). Minor isomer (exo): $R_f$(hexane/ethyl acetate, 20:1): 0.21. $^1$H NMR (400 MHz) δ: 0.06 (s, 9H, Si(CH$_3$)$_3$), 1.52 (s, 2H, CH$_2$SiMe$_3$), 1.83-1.99 (m, 2H, H-6), 2.04-2.23 (m, 2H, H-5), 2.51 (ddd, 1H, $^3J_{HH}$ 12.4, $^3J_{HH}$ 9.3, $^3J_{HH}$ 3.2, CHCO$_2$Me), 3.56 (s, 3H, CH$_3$OCO), 3.74-3.76 (dm, 1H, $^3J_{HH}$ 9.4, CHPh), 5.19 (broad s, 1H, H-3), 7.16-7.33 (m, 5H, Ph). $^{13}$C NMR (100 MHz) δ: −1.1 (Si(CH$_3$)$_3$), 26.0 (C-6), 27.8 (C-5), 30.1 (CH$_2$SiMe$_3$), 44.8 (CHPh), 48.6 (CHCO$_2$Me), 51.4 (CH$_3$OCO), 121.5 (C-4), 126.4 (para-Ar—C), 128.0, 128.3 (ortho-, meta-Ar—C), 135.9 (C-3), 145.0 (4° Ar—C), 175.8 (CO$_2$CH$_3$). IR (mixture of endo/exo isomers): 3029, 2951, 1738, 1435, 1248. HRMS: calcd for $C_{18}H_{27}O_2Si$ ([M+H]$^+$) 303.1780, found 303.1795.

Example 58 rac-(3aR,4R,5R,7aR)-5-Fluoro-6-methylene-4-phenylhexahydro-2-benzofuran-1,3-dione

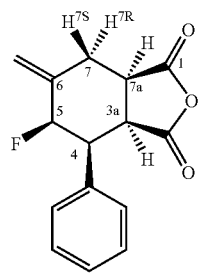

To a stirred solution of silylated cycloadduct of Example 54 (267 mg, 0.85 mmol) in 8.5 mL of CH$_3$CN was added Selectfluor (331 mg, 0.94 mmol). The mixture was allowed to react at room temperature for 1 h. The solvent was removed in vacuo, and chloroform (20 mL) was added to the reaction flask. The suspension was then stirred for 15 minutes to dissolve the organic products. The residues were removed by filtration and washed with chloroform (3×10 mL). The solvent was evaporated in vacuo, yielding a solid diastereomeric mixture with 45% yield. The product was purified by recrystallisation from hot ether, affording the product as colourless needle-shaped crystals (55 mg, 23%). $^1$H NMR (500 MHz) δ: 2.77-2.85 (mn, 1H, H$^{7R}$), 3.15 (d, 1H, $^3J_{trans-H^{7S}H^{7a}}$ 17.1, H$^{7S}$), 3.41 (dd, 1H, 3$J_{HF}$ 38.2, $^3J_{HH}$ 6.7, CHPh), 3.52-3.64 (m, 2H, H-3a, H-7a), 5.46 (s, 1H, C=CH$_2$), 5.47 (s, 1H, C=CH$_2$), 5.52 (d, 1H, $^2J_{HF}$ 58.4, CHF), 7.38-7.50 (m, 5H, Ph). $^{13}$C NMR (125 MHz) δ: 25.8 (s, C-7), 39.7 (s, C-7a), 42.0 (d, $^3J_{FC}$ 5.0, C-3a), 45.2 (d, $^2J_{FC}$ 20.4, CHPh), 93.2 (d, $^1J_{FC}$ 170, CHF), 120.1 (d, $^3J_{FC}$ 10.2, CH$_2$=C), 128.0 (s, para-Ar—C), 128.5 (d, $^4J_{FC}$ 3.1, ortho-Ar—C), 128.8 (s, meta-Ar—C), 136.5 (d, $^3J_{FC}$ 2.3, 4° Ar—C), 137.9 (d, $^2J_{FC}$ 14.6, C-6), 169.9 (s, C=O), 172.5 (s, C=O). $^{19}$F NMR (377 MHz) δ: −165.6 (ddq, $^2J_{HF}$ 57.2, $^3J_{HF}$ 37.2, $^3J_{HF}$ 6.0). IR: 2940, 1854, 1781, 1108, 1268. HRMS: calcd for $C_{15}H_{17}NO_3F$ ([M+NH$_4$]$^+$) 278.1192, found 278.1192. m.p.: decomposition before melting.

Example 59

Dimethyl rac-(3R,4S)-4-fluoro-5-methylene-3-phenylcyclohex-1-ene-1,2-dicarboxylate

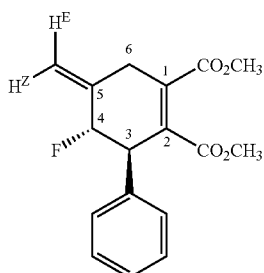

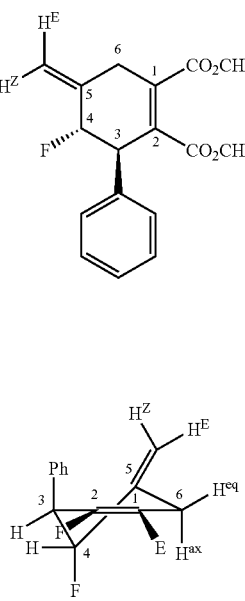

E = CO$_2$Me

To a stirred solution of silylated cycloadduct of Example 55 (150 mg, 0.39 mmol) in 4 mL of CH$_3$CN was added Selectfluor (152 mg, 0.43 mmol). The mixture was allowed to react at room temperature for 3 h. Following solvent removal in vacuo, the crude product was purified by column chromatography (hexane/ethyl acetate, 3:1) to afford the product as a colourless oil (74 mg, 58%). R$_f$ (hexane/ethyl acetate, 3:1): 0.31. $^1$H NMR (400 MHz) δ: 3.32-3.39 (m, 2H, H-6), 3.60 (s, 3H, CH$_3$OCO), 3.84 (s, 3H, CH$_3$OCO), 4.38 (dm, 1H, $^3$J$_{HF}$ 14.7, CHPh), 4.87-4.91 (m, 1H, C=CH$^Z$H$^E$), 4.96. (dd, 1H, $^2$J$_{HF}$ 48.5, $^3$J$_{HH}$ 2.9, CHF), 5.15-5.17 (m, 1H, C=CH$^Z$H$^E$), 7.11-7.32 (m, 5H, Ph). $^{13}$C NMR (100 MHz) δ: 31.1 (s, C-6), 49.6 (d, $^2$J$_{FC}$ 25.4, CHPh), 52.3 (s, CH$_3$OCO), 52.5 (s, CH$_3$OCO), 94.1 (d, $^1$J$_{FC}$ 175.0, CHF), 116.8 (d, $^3$J$_{FC}$ 9.7, CH$_2$=C), 127.6 (s, meta-Ar—C), 128.6 (d, $^3$J$_{FC}$ 6.9, ortho-Ar—C), 131.9 (s, para-Ar—C), 135.2 (d, $^2$J$_{FC}$ 17.6, C-5), 136.5, 136.6, 136.7 (s, 4° Ar—C, C-1, C-2), 166.9, 168.1 (s, CO$_2$Me). $^{19}$F NMR (377 MHz) δ: −167.6 (ddt, $^2$J$_{HF}$ 48.5, $^3$J$_{HF}$ 14.7, $^3$J$_{HF}$ 4.0). IR: 2953, 1726, 1650, 1435, 1270. HRMS: calcd for C$_{17}$H$_{21}$NO$_4$F ([M+NH$_4$]$^+$) 322.1455, found 322.1457. An NOE difference experiment was performed on this compound in deuterated benzene. An assigned proton NMR spectrum is included here for reference. $^1$H NMR (400 MHz, C$_6$D$_6$) δ: 3.14 (s, 3H, CH$_3$OCO), 3.14 (d, 1H, 2J$_{HH}$ 20.8, C$^6$H$^{ax}$H$^{eq}$), 3.27 (dm, 1H, $^2$J$_{HH}$ 20.9, C$^6$H$^{ax}$H$^{eq}$), 3.44 (s, 3H, CH$_3$OCO), 4.43-4.45 (m, 1H, C=CH$^Z$H$^E$), 4.63 (1H, dm, $^3$JHF 14.5, CHPh), 4.55 (app t, 1H, J 1.0, C=CH$^Z$H$^E$), 4.77 (dd, 1H, $^2$J$_{HF}$ 48.6, $^3$J$_{HH}$ 2.9, CHF), 6.95-6.99 (m, 5H, Ph).

Example 60 rac-1-[(1R,2S,3S)-3-Fluoro-4-methylene-2-phenylcyclohexyl]ethanone

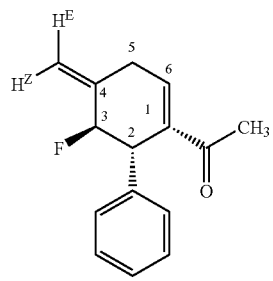

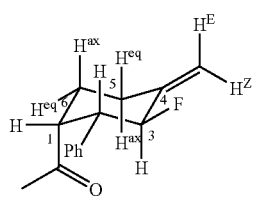

To a stirred solution of silylated cycloadduct of Example 56 (114 mg, 0.40 mmol) in 4 mL of CH$_3$CN was added Selectfluor (155 mg, 0.47 mmol). The mixture was allowed to react at room temperature for 4 h. Following solvent removal in vacuo, the crude product was purified by column chromatography (hexane/ethyl acetate, 4:1) to afford the product as a colourless oil (56 mg, 60%). Rf (hexane/ethyl acetate, 4:1): 0.25. $^1$H NMR (400 MHz) δ: 1.80-2.05 (m, 2H, H-6), 1.90 (s, 3H, CH$_3$CO), 2.39-2.57 (m, 2H, H-5), 3.31-3.43 (m, 2H, CHPh, CHAc), 5.04 (broad s, 1H, C=CH$_2$), 5.07 (s, 1H, C=CH$_2$), 5.64 (dd, 1H, $^2$J$_{HF}$ 49.5, $^3$J$_{HH}$ 7.4, CHF), 7.20-7.50 (m, 5H, Ph). $^{13}$C NMR (125 MHz) δ: 26.1 (s, C-6), 29.4 (d, $^3$J$_{FC}$ 2.2, C-5), 30.3 (s, CH$_3$CO), 50.5 (d, $^2$J$_{FC}$ 21.9, CHPh), 52.3 (d, $^3$J$_{FC}$ 4.1, CHAc), 92.1 (d, $^1$J$_{FC}$ 176.5, CHF), 110.9 (d, $^3$J$_{FC}$ 11.8, C=CH$_2$), 127.2 (s, para-Ar—C), 128.5, 128.6 (s, ortho-, meta-Ar—C), 138.0 (d, $^3$J$_{FC}$ 5.4, 4° Ar—C), 144.2 (d, $^2$J$_{FC}$ 15.1, C-4), 210.3 (s, CH$_3$CO). $^{19}$F NMR (377 MHz) δ: −194.4 (ddm, $^2$J$_{HF}$ 48.7, $^3$J$_{HF}$ 15.5). IR: 2947, 1705, 1232. HRMS: calcd for C$_{15}$H$_{17}$O ([M+H−HF]$^+$) 213.1279, found 213.1271. An NOE difference experiment was performed on this compound in deuterated benzene. An assigned proton NMR spectrum is included here for reference. $^1$H NMR (500 MHz, C$_6$D$_6$) δ: 1.37 (s, 3H, CH$_3$CO), 1.39-1.46 (m, 1H, C$^6$H$^{ax}$H$^{eq}$), 1.50-1.59 (m, 1H, C$^6$H$^{ax}$H$^{eq}$), 2.11-2.18 (m, 1H, C$^5$H$^{ax}$H$^{eq}$), 2.29-2.36 (m, 1H, C$^5$H$^{ax}$H$^{eq}$) 2.78-2.85 (m, 1H, CHAc), 3.16 (ddd, 1H, $^3$J$_{HF}$ 12.7, $^3$J$_{HH}$ 8.2, $^3$J$_{HH}$ 5.1, CHPh), 4.86 (s, 1H, C=CH$^Z$H$^E$), 5.14 (s, 1H, C=CH$^Z$H$^E$), 5.84 (dd, 1H, $^2$J$_{HH}$ 49.7, $^3$J$_{HH}$ 8.2, CHF), 6.97-7.20 (m, 5H, Ph).

Example 61

Methyl rac-(1R,2S,3S)-3-fluoro-4-methylene-2-phenylcyclohexanecarboxylate

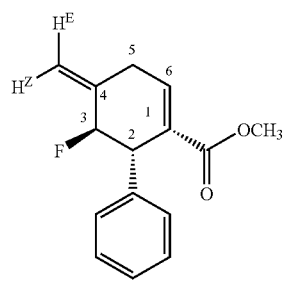

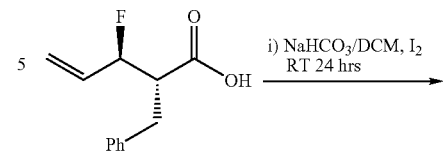

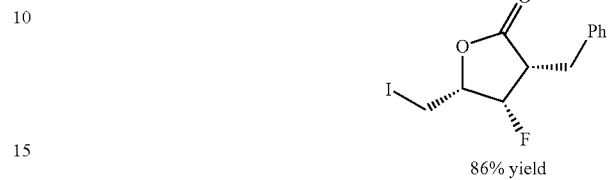

86% yield
de>95%

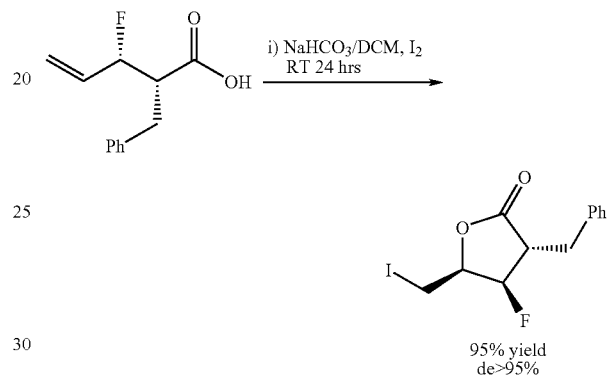

95% yield
de>95%

To a stirred solution of silylated cycloadduct of Example 57 (278 mg, 0.86 mmol) in 9 mL of $CH_3CN$ was added Selectfluor (364 mg, 1.03 mmol). The mixture was allowed to react at room temperature for 4 h. Following solvent removal in vacuo, the crude product was purified by column chromatography (hexane/diethyl ether, 8:1) to afford the product as a colourless oil (151 mg, 71%). $R_f$ (hexane/ethyl acetate, 4:1): 0.16. $^1H$ NMR (500 MHz) δ: 1.86-1.93 (m, 1H, $C^6H^{ax}H^{eq}$), 1.99-2.07 (m, 1H, $C^6H^{ax}H^{eq}$), 2.46-2.53 (m, 1H, $C^5H^{ax}H^{eq}$), 2.56-2.63 (m, 1H, $C^5H^{ax}H^{eq}$), 3.21-3.25 (m, 1H, $CHCO_2Me$), 3.43 (ddd, 1H, $^3J_{HF}$ 12.8, $^3J_{HH}$ 7.2, $^3J_{HH}$ 5.5, CHPh), 3.52 (s, 3H, $CH_3OCO$), 5.10 (broad s, 1H, $C=CH^ZH^E$), 5.13 (s, 1H, $C=CH^ZH^E$), 5.59 (dd, 1H, $^2J_{HF}$ 48.9, $^3J_{HH}$ 7.2, CHF), 7.24-7.33 (m, 5H, Ph). $^{13}C$ NMR (125 MHz) δ: 26.3 (s, C-6), 29.6 (d, $^3J_{FC}$ 1.6, C-5), 45.4 (d, $^3J_{FC}$ 4.4, $CHCO_2Me$), 50.2 (d, $^2J_{FC}$ 22.5, CHPh), 51.4 (s, $CH_3OCO$), 92.1 (d, $^1J_{FC}$ 175.8, CHF), 111.4 (d, $^3J_{FC}$ 12.0, $C=CH_2$), 127.2 (s, para-Ar—C), 128.3, 128.6 (s, ortho-, meta-Ar—C), 138.0 (d, $3J_{FC}$ 5.9, 4° Ar—C), 144.2 (d, $2J_{FC}$ 15.0, $C=CH_2$), 210.3 (s, $CO_2Me$). $^{19}F$ NMR (377 MHz) δ: −183.7 (dm, $^2J_{HF}$ 49.0). IR: 2950, 1732, 1657, 1238. HRMS: calcd for $C_{15}H_{17}O_2$ ([M+H−HF]$^+$) 229.1229, found 229.1224.

Example 62

Iodolactonization

Iodolactonization of β-fluorinated acids was carried out in DCM/NaHCO$_{3(aq)}$ and 1.1 eq of $I_2$ to give the beta-fluorinated lactones in good yields and excellent diastereoselectivity, crude de>95%. The stereochemistry of the products was determined from NOE experiments.

The sense of diastereocontrol is opposite for the two diastereomeric fluorinated carboxylic acids (syn and anti) and the level of diastereocontrol is very high.

Example 63

Synthesis of Enantiopure Fluorinated Carbocycles by Combining Diels Alder Reactions and Electrophilic Fluorodesilylation Asymmetric Dies-Alder Reaction Using a Chiral Auxiliary.

The major compound is shown by NMR spectroscopy to be formed by an endo transition state. The Absolute configuration has been assigned by analogy.

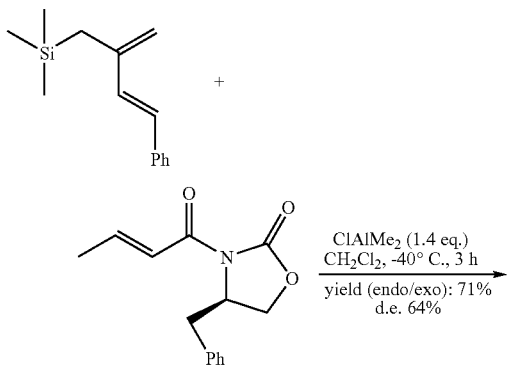

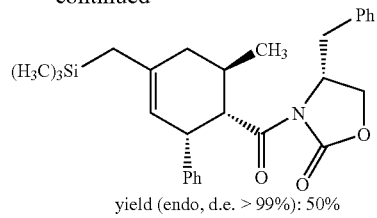

yield (endo, d.e. > 99%): 50%

After electrophilic fluorodesilylation with Selectfluor only one diastereoisomer could be detected by NMR spectroscopy. The latter analysis is consistent with an anti relationship between the phenyl and the fluorine.

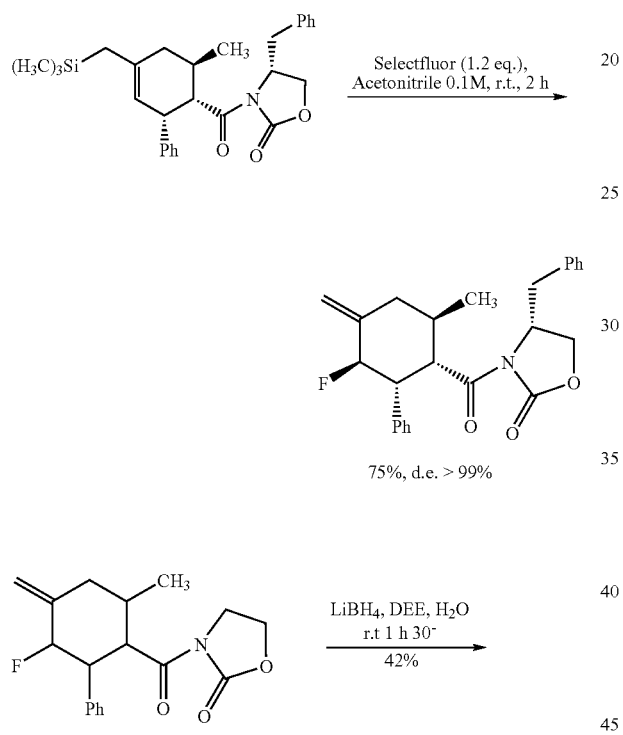

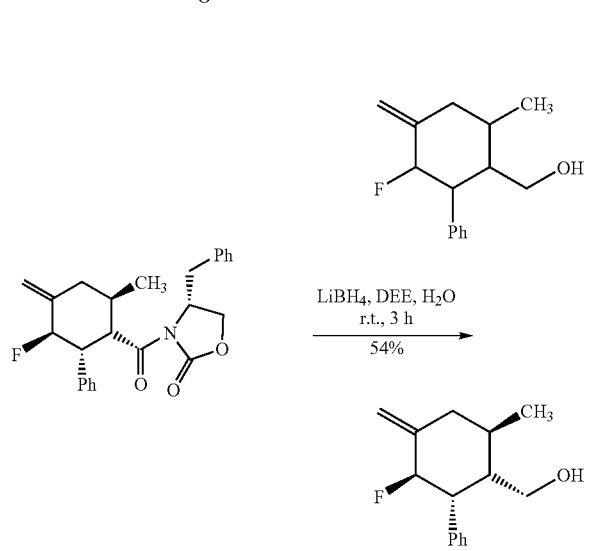

The invention claimed is:

1. A process for producing a compound of formula (IIIa)

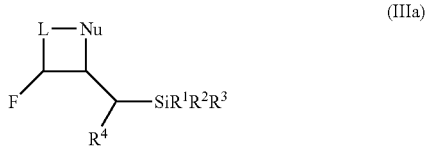

wherein $R^4$ is selected from hydrogen, -alk-H, aryl, -alk-aryl, —O—aryl, —O-alk-aryl-, -alk-O-aryl, -alk-O-alk-aryl, —O—alk-H, -alk-O-alk-H, —C(O)-aryl, —C(O)-alk-aryl, -alk-C(O)-aryl, -alk-C(O)-alk-aryl, —C(O)-alk-H, -alk-C(O)-alk-H, —C(O)N(-alk-H)C(O)O-alk-H, -alk-C(O)N(-alk-H)C(O)O-alk-H, wherein when $R^4$ is an unsubstituted or substituted hydrocarbon group with two or more carbon atoms it is saturated between C1 and C2;

$R^{10}$ is selected from $C_{1-6}$alkyl, $C_{2-6}$alkenyl, $C_{2-6}$alkynyl and phenyl;

$R^{11}$ and $R^{12}$, together with the nitrogen atom to which they are attached, represent an N-oxazolidinyl group which is substituted by $R^{10}$ or -alk-$R^{10}$;

-alk- is a straight or branched $C_{1-6}$alkylene, $C_{2-6}$alkenylene or $C_{2-6}$alkynylene group which is unsubstituted or substituted by halogen;

$R^1$, $R^2$ and $R^3$ are independently selected from $C_{1-6}$alkyl and phenyl, wherein at least one of $R^1$, $R^2$ and $R^3$ is not methyl;

L is a $C_{1-3}$alkylene group which is unsubstituted or substituted by one or more groups independently selected from $R^{10}$, aryl, -alk-aryl, —C(O)O-alk-H and —C(O)—NR$^{11}$R$^{12}$; and Nu is —C(O)O—; or L is a $C_{2-4}$alkylene group which is unsubstituted or substituted by one or more groups independently selected from $R^{10}$, aryl, -alk-aryl, —C(O)O-alk-H and —C(O)—NR$^{11}$R$^{12}$; and Nu is —O—;

by attaching a fluoro group gamma to a silane group, which process comprises contacting a source of electrophilic fluorine with a compound of formula (I):

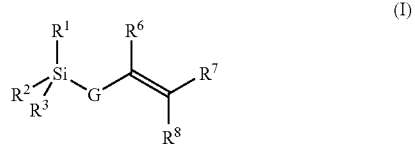

wherein $R^1$, $R^2$ and $R^3$ are independently selected from $C_{1-6}$alkyl and phenyl and at least one of $R^1$, $R^2$ and $R^3$ is not methyl; G is —C($R^4$)($R^5$)—, $R^4$ is as defined above, $R^5$, $R^6$ and $R^8$ are hydrogen; $R^7$ is -L-NuH; L and Nu are as defined above; and the compound produced is of formula (IIIa) as defined above.

2. A process according to claim 1 wherein, the source of electrophilic fluorine is [1-(chloromethyl)-4-fluoro-1,4-diazoniabicyclo[2.2.2]octane bis(tetrafluoroborate)].

3. A process according to claim 1 wherein L is a $C_1$alkylene or $C_2$alkylene group and Nu is —C(O)O—, or L is a $C_2$alkylene or $C_3$alkylene group and Nu is —O—.

4. A process according to claim 1 wherein L is unsubstituted.

5. A process according to claim 1 wherein $R^4$ is H or -alk-H and (i) L is an ethylene group which is unsubstituted or substituted by one or more of $R^{10}$, aryl and -alk-aryl and Nu is —O—; or (ii) L is a methylene group which is unsubstituted or substituted by one or more of $R^{10}$, aryl and -alk-aryl and Nu is —C(O)O—.

6. A process according to claim 5 wherein $R^4$ is H.

7. A process according to claim 5 wherein either (i) L is an ethylene group substituted by a phenylethyl group alpha to Nu and Nu is —O—, or (ii) L is an unsubstituted methylene or ethylene group and Nu is —C(O)O—.

8. A process according to claim 7 wherein $SiR^1R^2R^3$ is an $Si^iPr_3$ group.

9. A process according to claim 1 wherein said aryl groups contain from 6 to 10 carbon atoms and are unsubstituted or substituted with one or two substituents, which substituents are selected from the group consisting of nitro, halo, $C_{1-6}$alkyl and $C_{1-6}$alkoxy.

10. A process according to claim 1 wherein $R^1$, $R^2$ and $R^3$ are each selected from methyl, ethyl, t-butyl, i-propyl and phenyl.

11. A process according to claim 1 wherein $SiR^1R^2R^3$ is $SiMe_2{}^tBu$, $Si^iPr_3$, $SiPh^iPr_2$, $Si^tBuPh_2$ or $SiPh_3$.

12. A process according to claim 1 wherein $R^4$ is selected from hydrogen and $C_{1-6}$alkyl.

\* \* \* \* \*